United States Patent [19]
Schuelke et al.

[11] Patent Number: 6,112,119
[45] Date of Patent: Aug. 29, 2000

[54] METHOD FOR AUTOMATICALLY ADJUSTING THE SENSITIVITY OF CARDIAC SENSE AMPLIFIERS

[75] Inventors: Robert J. Schuelke, Lakeville; James W. Busacker, St. Anthony; James D. Reinke; Kevin L. Bright, both of Maple Grove; Russell E. Anderson, Marine on St. Croix; Virginia De La Riva, Minneapolis; David W. Hoffman, Inver Grove Heights; Ren Zhou, New Brighton, all of Minn.

[73] Assignee: Medtronic, Inc., Minneapolis, Minn.

[21] Appl. No.: 08/957,908

[22] Filed: Oct. 27, 1997

[51] Int. Cl.$^7$ ..................................................... A61N 1/362
[52] U.S. Cl. .................................................................. 607/9
[58] Field of Search ..................................................... 607/9

[56] References Cited

U.S. PATENT DOCUMENTS

| | | |
|---|---|---|
| 3,927,677 | 12/1975 | Gobeli et al. . |
| 4,000,461 | 12/1976 | Barber et al. . |
| 4,240,442 | 12/1980 | Andresen et al. . |
| 4,325,384 | 4/1982 | Blaser et al. . |
| 4,374,382 | 2/1983 | Markowitz . |
| 4,379,459 | 4/1983 | Stein . |
| 4,708,144 | 11/1987 | Hamilton et al. . |
| 4,766,902 | 8/1988 | Schroeppel ................................. 607/9 |
| 4,768,511 | 9/1988 | DeCote, Jr. . |
| 4,880,004 | 11/1989 | Baker et al. . |
| 5,103,819 | 4/1992 | Baker et al. . |
| 5,312,455 | 5/1994 | Zadeh . |
| 5,331,966 | 7/1994 | Bennett et al. . |
| 5,395,393 | 3/1995 | Wickham . |
| 5,702,425 | 12/1997 | Wickham ..................................... 607/9 |

Primary Examiner—William E. Kamm
Assistant Examiner—George R. Evanisko
Attorney, Agent, or Firm—Harold R. Patton; Reed A. Duthler

[57] ABSTRACT

Two mechanisms work together to adjust two variables independently so that the gain of an input amplifier used to find physiologic signals in an implantable medical device can be automatically adjusted to enhance the signal to noise ratio of the electrical input to said amplifier. The first determines whether there has been too long a time between senses found in the body's electrical input to the amplifier and if true, and no other conditions override that consideration, it adjusts the value of a long term average parameter which is used as a referent parameter to adjust the actual parameter that is used as the referent for making either a threshold level adjustment or gain change, depending on the structure of the particular design's circuitry and/or software. One set of adjustments to the gain referent parameter depends on the relative size of the long term average parameter and the gain referent parameter. The mechanisms preferably employ counting registers, the one which adjusts the gain referent having a process to weight input signals such that those of different types get different weights, and the other mechanism only accepting certain of the input signals. Input signals to the two mechanisms can be either physiologically based or from stimulation pulses issued from an implanted device, such as, for example a pacemaker.

21 Claims, 22 Drawing Sheets

OPERATION OF RPA

OPERATION OF SMIACC

SENSING ASSURANCE SMIACC WEIGHTS

| PRESENT SMIACC VALUE | NON-PVC NON-REFRACTORY SENSE | | PVC[a] NON-REFR SENSE | INVALID SENSE | PACE |
|---|---|---|---|---|---|
| | LOW | ADEQUATE | HIGH | | | |
| ≥80 | -8 | -8 | +5 | -1 | -8 | -1 |
| <80 | -5 | +8 | +8 | +1 | +8 | +1 |

OPERATION OF PEA

METHOD FOR AUTOMATICALLY ADJUSTING THE SENSITIVITY OF CARDIAC SENSE AMPLIFIERS

FIELD OF THE INVENTION

The present invention relates to sense amplifiers for sensing cardiac events, and particularly to an "AutoSensing" algorithm incorporated into an implantable monitor and/or stimulator for adjusting the sensitivity of such sense amplifiers to provide an optimal sensing margin.

BACKGROUND OF THE INVENTION

As described in detail in U.S. Pat. No. 5,312,455, modern, multi-programmable, multi-mode implantable pacemakers, and by extension other implantable cardiac stimulators, monitors or the like, are equipped with sense amplifiers that are designed to detect depolarizations of myocardial tissue constituting features of the electrogram (EGM) as a "sense event" and record data related to the sense event and/or affect the operation of such devices. The time varying and oscillating EGM amplitude reflects the depolarizations of atrial and ventricular chamber heart tissue in a normal activation sequence, wherein the oscillations of the signal are characterized by convention as a "PQRST" complex. The PQRST complex is described below in reference to the illustration thereof in FIG. 5 in reference to sensing electrodes located in atrial and ventricular locations. The sense electrode(s) location affects the shape of the PQRST complex and polarity of the successive oscillations, but usually the individual transitions are evident.

In practice, regardless of its shape, the PQRST complex is conventionally simplified by reference to the same polarity oscillations which constitute the relatively low amplitude "P-wave", followed by a higher amplitude "R-wave" (separated by an "A-V" interval) and then concluded by a low amplitude "T-wave". The intrinsic "escape interval" between successive P-waves or R-waves defines the heart rate (in beats per minute). The P-wave has a pulsatile wave shape manifesting the electrical depolarization wave of the atria, and the R-wave and T-wave shapes manifest the rapid depolarization and slow re-polarization waves of the ventricles, respectively.

In some applications, related to monitoring of the patient's heart activity, it is desirable to sense and record the full PQRST EGM or to providing responsive device-delivered therapy sensing and recording other electrical noise and interference. However, it is also desirable to detect the P-wave and/or the R-wave and so that the A-V and intrinsic escape intervals can be timed in both monitors and therapeutic cardiac stimulators and so that certain operations may be initiated on detection of the P-wave or R-wave. In this process, it is undesirable to detect and mistake the T-wave for the P-wave or for a succeeding R-wave, for example, or to miss a P or T-wave in the noise. The simplest thing to do is to establish blanking periods as described in U.S. Pat. No. 4,379,459 to Stein which retains information about noise through the blanking period.

Naturally, the amplitude, and to some extent the rate of change or slope, of the P-wave and R-wave signal may be used to distinguish one from the other and from the T-wave. With respect to amplitude distinction, the sense amplifiers of modern monitors and/or stimulators are configured to have a bandpass response and a "sensitivity" to the signal amplitude that may be varied in order to trigger a "sense event" when the proper P-wave or R-wave is present. The greater the sensitivity, the lower the signal amplitude necessary to trigger the sense event. The sensitivity is typically a function of the gain of the sense amplifier or a function of a "sensing threshold" against which the amplified signal is compared. In the latter case, the sensitivity is therefore inversely related to the sensing threshold.

In practice, the detection of P-waves and R-waves is complicated by a number of factors or abnormal conditions which mask, elevate or diminish the signal amplitudes, so that the signals, even if present may not be sensed (referred to as "undersensing") or too many sense events may be triggered (referred to as "oversensing"). Tissue overgrowth of implantable electrode surfaces, referred to as "aging", can chronically alter the signal amplitude. Short term electromagnetic interference (EMI) conducted through the body from external sources and muscle artifacts or myopotentials originating within the body may mask the EGM. The EMI sources can either be intentionally introduced by such events as programmer downlink, cautery, defibrillation, and fluoroscopy, or unintentionally introduced by any number of radiating electronic devices, such as cell phones and anti-theft detection devices. Exercise levels, heavy breathing, medications and temperature changes may also constitute an abnormal condition that influences the EGM signal level. (In some cases, the changing impedance of the heart can drown out the impedance signals used to find minute ventilation as in U.S. Pat. No. 5,271,395 (Whalstrand et al.), requiring some kind of low pass filtering to find the breath signal. Impedance measurement may use the same sense amp (amplifier) that finds the EGM.)

When oversensing occurs in a demand pacemaker, the pacing function may be erroneously continuously inhibited, leading to loss of cardiac output and injury to the patient. An early way of countering oversensing due the continuous presence of EMI, was to sense the noise and "revert" to asynchronous pacing, i.e., go into "reversion". This kind of reversion is also called "noise reversion pacing."

However at least since the Gobeli & Adams patent (U.S. Pat. No. 3,927,677) and many which follow it, reversion in response to EMI has been supported with schemes to cancel the EMI noise as in for example Meltzer, U.S. Pat. No. 5,647,379. Nevertheless such circuits and their operation in the presence of continuous EMI are still referred to as "reversion" circuits or operations, even though demand pacing is assured.

For many years, it has also been possible to remotely program the sensitivities of such sense amplifiers in implanted pacemakers, cardioverter/defibrillators, other stimulators, or monitors within a range in order to compensate for other, more long term, changes in signal amplitude. In practice, in one approach, a range of programmable sensing threshold values is provided for selection by a physician at implantation and which can be periodically re-programmed during patient follow-up visits to ensure that the proper P-wave or R-wave is being detected.

In addition, automatic sensitivity adjusting systems have been proposed and implemented in both external and implantable embodiments of such stimulators or monitors. A first approach, similar to the reversion approach described above, adjusts the threshold to the average signal level over a certain time span, as shown, for example, in U.S. Pat. No. 4,240,442. In a somewhat related fashion, threshold levels to comparator inputs are adjusted to as shown in U.S. Pat. Nos. 4,768,511; 5,312,455; and 5,395,393. In these approaches, constant gain sense amplifier stages first amplify the filtered EGM and then compare the amplified signal to the adjustable threshold level and generate a sense event if the threshold is exceeded.

In further approaches, adjustable gain sense amplifier stages are employed, and automatic sense amplifier gain adjustment is employed as proposed in U.S. Pat. Nos. 4,000,461; 4,325,384; 4,708,144 and 4,880,004. Generally, comparators are employed in AGC feedback networks to make the gain adjustment in relation to a target voltage.

In certain of these approaches, e.g. the above-referenced '384, '004, and '461 patents, one or two additional comparators and further peak thresholds are employed to provide a peak target or range in which to bracket the peak of the sensed signal. The sensing threshold and the peak thresholds are adjusted in tandem to ensure that the peak amplitude either approaches and "dithers" about a single peak threshold or falls between a pair of peak thresholds.

An enhancement to these was shown in Baker et al., U.S. Pat. No. 5,103,819, which, after a fashion, adjusted the sense amp gain up in the presence of senses below a low threshold level and up in the presence of senses above a high threshold. Many patients who have implanted cardiac pacemakers, cardioverter/defibrillators or arrhythmia (or other) monitors are susceptible to a variety of arrhythmias. For example, many such patients have irregular heart rhythms marked by the occurrence of ectopic origin or circus rhythm conducted P-waves and ectopic origin R-waves. Typically, these premature atrial contractions (PACs) or premature ventricular contractions (PVCs) manifest excessive amplitudes and widths which can skew the adaptive threshold values. Runs of such PVCs and PACs may be processed in the above-described systems to reduce sensitivity, resulting in loss of sensing of succeeding normal conducted depolarizations.

These and other patients may be also be susceptible to episodes of atrial or ventricular tachyarrythmias with widened signal wave shapes and decreased amplitude. Such tachyarrythmia episodes of diminished peak amplitude may be processed in the above-described systems to increase sensitivity, resulting in oversensing of succeeding normal conducted depolarizations and any other signals.

In addition, abnormal noise and myopotential episodes occur from time to time as described above, which, if not accounted for can cause the sensing threshold to be unduly elevated when the noise abates, resulting in undersensing.

Finally, in actual experience with cardiac pacemakers, there may be long periods of little intrinsic cardiac activity to sense because the underlying heart rate is lower than either a fixed lower pacing rate or the pacing rate is being adjusted to the need for cardiac output as indicated by a physiologic or patient activity sensor of a rate responsive pacemaker. Such episodes may be entirely normal but constitute an abnormal condition to the sensitivity adjusting algorithm resulting in the sensitivity being increased to a level resulting in oversensing of noise within the sensing intervals.

Therefore, a need continues to exist for automatic sensitivity adjustment of a cardiac sense amplifier that takes into account short term variations in cardiac signal amplitude due to respiration, posture changes, exercise, drug therapies, etc., avoids responding to noise and myopotentials, premature beats or other arrhythmias, and compensates for periods of little sensing which thereby minimizes instances of oversensing and undersensing resulting from inappropriately adjusted sensing thresholds. Each patent referred to in this section is hereby by this reference incorporated into this application in their respective entireties so as to include all their disclosure without the need for reiteration.

SUMMARY OF THE INVENTION

It is therefore an object of the present invention to automatically adjust sensing thresholds to be used for each sensing period of such a sense amplifier which may monitor physiologic events such as heart depolarizations occurring in a chamber of a heart in a highly selective manner that avoids increasing or decreasing the threshold in response to abnormal conditions that would result in undersensing or oversensing on resumption of sensing of normal cardiac signals under normal conditions. The range of adjustment can be bounded if desired.

These and other objects of the invention are realized in a set of circuit elements for an implantable medical device capable of adjusting the gain of a sense amp monitoring cardiac signals or other electrical signals in the body.

The features described include:
- adjusting sensing threshold based on the peak amplitude of the cardiac waveform,
- adjusting the sensing threshold in response to background noise signal amplitudes,
- windowing the measurements of the peak amplitude to a specific period of time relative to the cardiac event to reduce susceptibility to noise in the received signals
- rejecting the noise in the received signals by testing the duration of the cardiac signal. If the duration is longer than would be reasonable for a cardiac event the amplitude measurements can be not considered in the sensing threshold adjustment process.

This features also includes maintaining a baseline sensing threshold as an operating point to return to during long periods of little sensing. This baseline can either be a fixed threshold or can be maintained as a long term average that reflects the operating history of the device.

Further features include;
- identifying periods of little sensing by maintaining a running weighted counter of sensed and paced events
- identifying periods of reversion pacing by maintaining a running weighted counter of sense events, reversion paces, and non-reversion paces. Reversion pacing occurs when the device paces asynchronously while the sense amplifiers are reverted (i.e., when the sense amplifiers are "blinded" by excessive levels of background noise). Still further features include; using reversion pacing status and current sensing threshold setting relative to the baseline sensitivity to make intelligent decisions on sensing threshold adjustments during periods of little sensing, treating sense events identified as high amplitude PVC's as a special case in order to avoid potentially tracking noise signals as cardiac events. To also prevent improper adjustment of sensitivity in patients who present only PVC's, and screening the data used by discarding events when they exceed reasonable signal amplitudes or duration's for a cardiac event or if the background continuous noise level exceeds a specific fraction of the current sensing threshold.

Generally, these features are implemented preferably in a combination of hardware and software using an interrupt signal for indicating the occurrence of a sensed event exceeds a time window setting, with registers for counting the number of appropriate versus inappropriate senses for a given gain setting, flagging whether an event is a paced or intrinsic sense, and if a paced event, whether it is reversionary, these last two registers determining whether there has been too long a time between intrinsic senses to rely on a current gain setting. It has been discovered that the functionality described can be maintained without the timing window at a satisfactory level of performance.

The operation of the invention employs at least two indicator trackers, preferably three, which interoperate to adjust a threshold or gain value and a long term average threshold or gain value as each indicator tracker becomes ready to do so, each one independently determining its readiness based employing its own criteria to historical data each independently compiles concerning either the number of senses or the sense event's different types or sizes, these characteristics determined based on each output of sense amplifier signals. A separate set of these indicator trackers and gain or threshold values and long term average values should be used for each sense amplifier being gain controlled in n accord with this invention.

The first indicator would be of long time with few senses (except in the special case of an Atrial sense amp in a pacemaker in VDD mode), which preferably tracks both pacing and noise reversion status. This indicator can adjust the gain, but only in the direction of the long term average (LTA).

The second indicator would track the long term average gain value (or threshold value) based on any sensor signals considered acceptable in accord with its criteria. It also preferably maintains a counter so that adjustments to the long term average can only occur when the counter is full, thus slowing down the adjustment of the LTA value.

The third would be a sense margin indicator, which tracks each sense, and also each pace, and gives different weightings to different types of senses and paces, and when it reaches either an upper value or a lower value, produces an output indicating that it thinks the gain should be adjusted either up or down depending on whether the upper or lower value was reached.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The present invention may be implemented in a variety of external or implantable medical devices, including pacemakers for detecting and treating bradyarrhythmias, cardiac signal monitors, and cardioverter/defibrillators for detecting and treating tachyarrythmias including fibrillation. The invention may be implemented in both dual chamber and single chamber pacemakers operating in any of the known modes involving sensing of the EGM. While the following description of the invention is in the context of implantable, multi-programmable, DDDR pacemakers of types widely known in the prior art, it will be understood that any of these devices and others may benefit from the invention. A number of patent references will be described in this section and they are incorporated into this disclosure in their respective entireties by this reference.

The present invention involves the adjustment of sensing threshold(s) $I_{TH}$ (expressed as an electrical current level) of a sense amplifier in the manner summarized above and described in detail below, from a preceding sensing threshold value which, at the outset, may be a programmed-in, physician determined setting (PDS) or a pre-set nominal sensing threshold value. The AutoSensing algorithm summarized above is invoked in this process.

The device using this invention may have factory built-in or programmable limits to the gain setting if desired, which would override any other adjustment feature described herein. It should also be noted that the adjustment to the gain is made at most one time between senses, and generally will not occur after every paced or sensed event, but will rather adjust over a period the length of which will depend on the functioning of the indicator mechanisms over the course of a multiplicity of heartbeats (i.e., physiologic indicator cycles).

Before describing the various aspects of the present invention in detail, the following description of a hardware and software implemented dual chamber pacemaker of FIGS. 1–7 is set forth in the disclosure of a preferred mode of implementing the invention.

Dual Chamber Pacemaker Block Diagram

Figure 1:
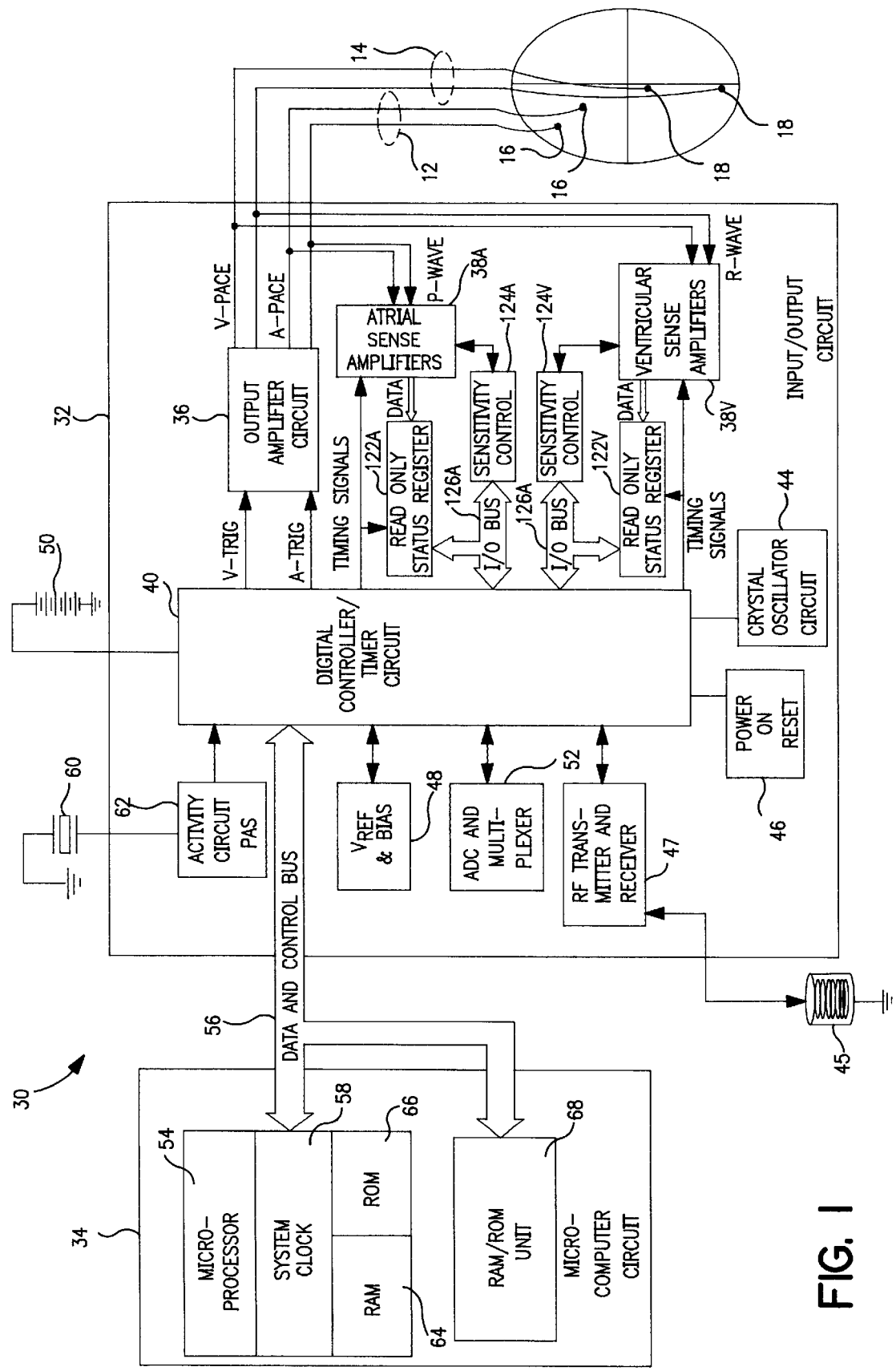
FIG. 1 is a system block diagram of the architecture of a DDDR pacemaker in which the present invention may be practiced.

FIG. 1 is block level diagram of such a pacemaker implantable pulse generator or IPG circuit 30 and lead set 12 and 14 which sets forth the structures required to incorporate the invention into a DDDR pacemaker. In the drawing, the patient's heart 10 has an atrial pacing lead 12 passed into the right atrium and a ventricular lead 14 passed into the right ventricle. The atrial lead 12 has an atrial electrode array 16 which couples the IPG circuit 30 to the atrium. The ventricular lead 14 has a ventricular electrode array 18 for coupling the IPG circuit 30 to the ventricle of the patient's heart 10. Atrial and ventricular leads 12 and 14 are depicted as bipolar leads coupled to a bipolar IPG circuit 30, although unipolar leads could be employed with a suitable IPG.

The IPG circuit 30 of FIG. 1 is divided generally into a pacing circuit 32 coupled to a battery (or other source of) power supply 50, an activity sensor 60 of the type described below, a telemetry coil 45 and a microcomputer 34. The pacing circuit 32 includes the atrial and ventricular output amplifier circuit 36 and the atrial and ventricular sense amplifiers 38A and 38V that are coupled to the atrial and ventricular leads 12 and 14, respectively, the digital controller/timer circuit 40 and other associated components described below.

The output circuit 36 may contain atrial and ventricular pulse generators and sense amplifiers corresponding to any of those presently employed in commercially marketed dual chamber cardiac pacemakers. In order to trigger generation of a ventricular pacing or V-PACE pulse, digital controller/timer circuit 40 generates and provides a V-TRIG signal to the ventricular pulse generator. Similarly, in order to trigger an atrial pacing or A-PACE pulse, digital controller/timer circuit 40 generates and a provides an A-TRIG pulse to the atrial pulse generator. Digital controller/timer circuit 40 also controls the pulse widths and amplitudes of the A-PACE and V-PACE pacing pulses.

The atrial pacing and sensing functions are carried out by the interaction of the digital timer/controller circuit 40 with the atrial sense amplifier 38V and output amplifier circuit 36 and other described components collectively referred to herein as the "atrial channel". Similarly, the ventricular pacing and sensing functions are carried out by the interaction of the digital timer/controller circuit 40 with the ventricular sense amplifier 38v and output amplifier circuit 36 and other described components collectively referred to herein as the "ventricular channel".

Crystal oscillator circuit 44 provides the basic clock frequency for the circuit 30 from which various timing clocks are developed. Voltage reference and bias circuit 48 generates stable voltage reference and current levels for the analog circuits within the IPG circuit 30 from the battery voltage and current provided by battery 50. Power-on-reset (POR) circuit 46 responds to initial connection of the IPG circuit 30 to the battery 50 for defining an initial operating condition and also resets the operating condition in response to detection of a low battery energy condition.

Analog to digital converter (ADC) and multiplexer circuit 52 digitizes certain analog signals and voltage levels for uplink transmission via RF transmitter and receiver circuit 47. Voltage reference and bias circuit 48, ADC and multiplexer 52, POR circuit 46 and crystal oscillator circuit 44 may correspond to any of those presently used in current marketed implantable cardiac pacemakers.

Data transmission is preferably to and from an external programmer (not shown) is accomplished by means of the telemetry antenna 45 and the associated RF transmitter and receiver 47, which serves both to demodulate received downlink telemetry and to encode and transmit uplink telemetry in a manner well known in the art. Uplink telemetry capabilities will typically include the ability to transmit stored digital information as well as digitized real time or stored EGMs of atrial and/or ventricular electrical activity, as well as transmission of Marker Channel pulses indicating the occurrence of sensed and paced depolarization's in the atrium and ventricle (U.S. Pat. No. 4,374,382 to Markowitz describes "Marker Channels"). Historical data related to the current sensing thresholds $I_{TH}$ and other related data described in detail below for the atrial and ventricular sense amplifiers 38A and 38V may be retained in memory and telemetered out using uplink telemetry on an interrogation command received from an external programmer.

Turning to atrial and ventricular sensing functions, FIG. 1 depicts I/O buses 126A and 126V extending between digital controller/timer circuit 40 and sensitivity control registers 124A and 124V and read only status registers 122A and 122V, respectively. A number of signals provided by the atrial and ventricular sense amplifiers 38A and 38V are latched in atrial and ventricular read only status registers 122A and 122V in a manner described below with reference to FIG. 3. In particular, atrial sense amplifier 38A responds to atrial depolarization's or P-waves in the atrial EGM from atrial electrodes 16 that exceed an atrial current sensing threshold $I_{TH}$ to cause an atrial ISENSE (AISENSE) event to be latched in a bit stage of status register 122A. Similarly, ventricular sense amplifier 38V responds to ventricular depolarization's or R-waves in the ventricular EGM from ventricular electrodes 18 that exceed a ventricular atrial sensing threshold $I_{TH}$ to cause a ventricular ISENSE (VISENSE) event to be latched in a bit stage of status register 122V. As disclosed below, read only registers 122A and 122V compile data bits in stages thereof reflecting the AISENSE and VISENSE intrinsic events as well as a number of other conditions and events.

The AISENSE and VISENSE intrinsic sense events are applied through digital timer/controller 40 and on the data and control bus 56 as interrupts to the microcomputer 34. The status of the other data bits stored in read only registers 122A and 122V read out and similarly applied to the microcomputer 34 as described below to control the sensitivity of the sense amplifiers 38A and 38V and other operating conditions.

It should be noted that for application to implantable devices, P, R and T wave sensing may be accomplished through various mechanisms. Thus, this invention can be used in unipolar devices, and for devices without leads that may have an electrode array, for example on their surfaces to read EGM's. For an example of how this could be done see U.S. Pat. No. 5,331,966, issued to Bennett et al.

The sensitivity control registers 124A and 124V adjust the sensitivities (and other functions as described below) of the sense amplifier 38A and 38V, respectively, in response to data and control signals provided to and from digital controller/timer 40 on I/O buses 126A and 126V, respectively. For example, the atrial and ventricular current sensing threshold $I_{TH}$ is calculated in microcomputer 34 and transmitted to the sensitivity control registers 124A and 124V, respectively. Blanking, disabling, recharge limiting, POR, timing clocks and test signals are provided from digital controller/timer circuit 40 to the atrial and ventricular sense amplifiers 38A and 38V on the atrial and ventricular TIMING SIGNALS lines, respectively. Power is also supplied to sense amplifiers 38A, 38V and other blocks of the IPG circuit 30 from voltage reference and bias 48.

Control of timing and other functions within the pacing circuit 30 is provided by digital controller/timer circuit 40 which includes a set of timers and associated logic circuits connected with the microcomputer 34.

Microcomputer 34 controls the operational functions of digital controller/timer 40, specifying which timing intervals are employed, and controlling the duration of the various timing intervals, via data and control bus 56. Microcomputer 34 contains a microprocessor 54, associated system clock 58, and may haul RAM and ROM circuits 64 and 66, respectively. In addition, microcomputer circuit 34 may include a separate RAM/ROM chip 68 to provide additional memory capacity. Microprocessor 54 is preferably interrupt driven, operating in a reduced power consumption mode normally, and awakened in response to defined interrupt events, which may include the A-TRIG and V-TRIG (atrial and Ventricular escape interval time-outs, respectively) signals, the AISENSE and VISENSE that is a signal representing the finding of an Atrial and Ventricular sensed events respectively signals and related signals. The specific values of the intervals defined are controlled by the microcomputer circuit 54 by means of data and control bus 56 from programmed-in parameter values and operating modes.

If the IPG circuit 30 is programmed to a rate responsive mode, a patient's activity level is monitored periodically, and a sensor derived pacing escape interval is adjusted proportionally. A timed interrupt, e.g., every two seconds, may be provided in order to allow the microprocessor 54 to analyze the output of the activity circuit (PAS) 62 and update the basic V-A (from Atrial event to next Ventricular event) escape interval employed in the pacing cycle. In the DDDR mode, the V-A escape interval may be selected as the variable pacing rate establishing interval, but the A-V interval and the atrial and ventricular refractory periods may also vary with the V-A escape interval established in response to patient activity.

Preferably, two separate lower rate V-A interval timer functions are provided. The first is set by the physician as a base or lower pacing rate. This DDD V-A time interval starts from the occurrence of a V-TRIG or a VISENSE event, and an A-TRIG signal is generated at the expiration of the V-A time interval unless an AISENSE or a VISENSE signal is detected by the sense amplifiers 38A or 38V during the V-A time interval. The duration of the second lower rate time interval is a function of the measured patient activity acquired by the activity sensor 21. Typically, this DDDR, V-A time interval begins with a VISENSE or V-TRIG and has a time duration reflecting patient activity. In this art, such structures are well known, and a variety of techniques can be used to implement the required timer functions.

Digital controller/timer circuit 40 starts and times out these and other intervals employed over a pacing cycle comprising a successive A-V and V-A interval in a manner well known in the art. Typically, digital controller/timer circuit 40 defines atrial blanking intervals commencing when an A-TRIG pulse is delivered, during which atrial sensing is disabled, as well as ventricular blanking intervals commencing when either A-TRIG or a V-TRIG pulse is delivered, during which ventricular sensing is disabled. Digital controller/timer circuit 40 also defines the Atrial Refractory Period (ARP) during which an AISENSE interrupt is ignored for the purpose of resetting the V-A escape interval. The ARP extends from the beginning of the A-V interval following either an AISENSE or A-TRIG interrupt and until a predetermined time following sensing of a ventricular depolarization or triggering the delivery of a V-PACE (Ventricular Pace) pulse. A Post-Ventricular Atrial Refractory Period (PVARP) is also defined commencing on triggering a V-PACE pulse. The duration's of the ARP, PVARP and VRP (Ventricular Refractory Period) may also be selected as a programmable parameters stored in the microcomputer 34.

Digital controller timer/logic circuit 40 also times out an upper rate limit interval (URL) set by a value programmed into memory in microcomputer circuit 34. This timer is initiated by the occurrence of a V-PACE or a VISENSE event, and limits the upper rate at which V-PACE pulses are delivered to the heart. The lower pacing rate is established by a programmed-in V-A or A-A interval value stored in memory in microcomputer circuit 34.

The illustrated IPG (Implantable Pulse Generator) circuit 30 of FIG. 1 is simplified and merely exemplary, and corresponds to the general functional organization of most multi-programmable microprocessor controlled DDDR cardiac pacemakers presently commercially available. It is believed that the present invention is most readily practiced in the context of such a device, and that the present invention can therefore readily be practiced using the basic hardware of existing microprocessor controlled, typically hermetically sealed, single or dual chamber pacemakers, as generally with the invention implemented primarily by means of modifications to the software stored in the ROM 66 of the microcomputer circuit. Numerous additional features may also be available presently that are not described because they are not related to this invention. Also this invention maybe used in any implanted IPG with or without pacemaker functions, for example nerve stimulators, drug pumps and Cardioverter Defibrillators if they monitor cardiac function.

Also, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacemaker having an architecture as illustrated in FIG. 1. Implantable devices which merely monitor heart function would also benefit from this invention.

Figure 2:
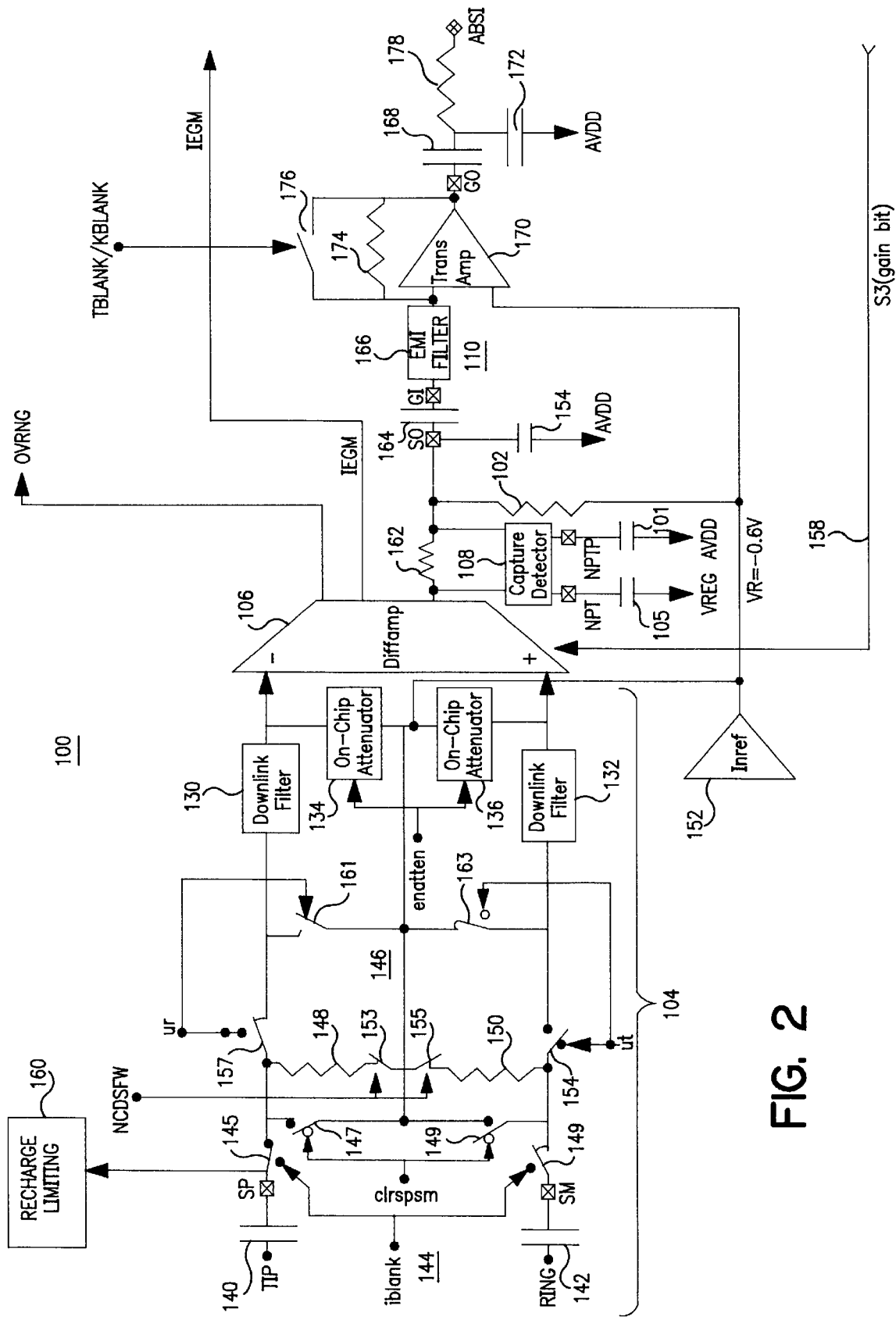
FIGS. 2 and 3 are schematic diagrams of the atrial and ventricular sense amplifiers and associated sensitivity control circuits of FIG. 1.
Figure 3:
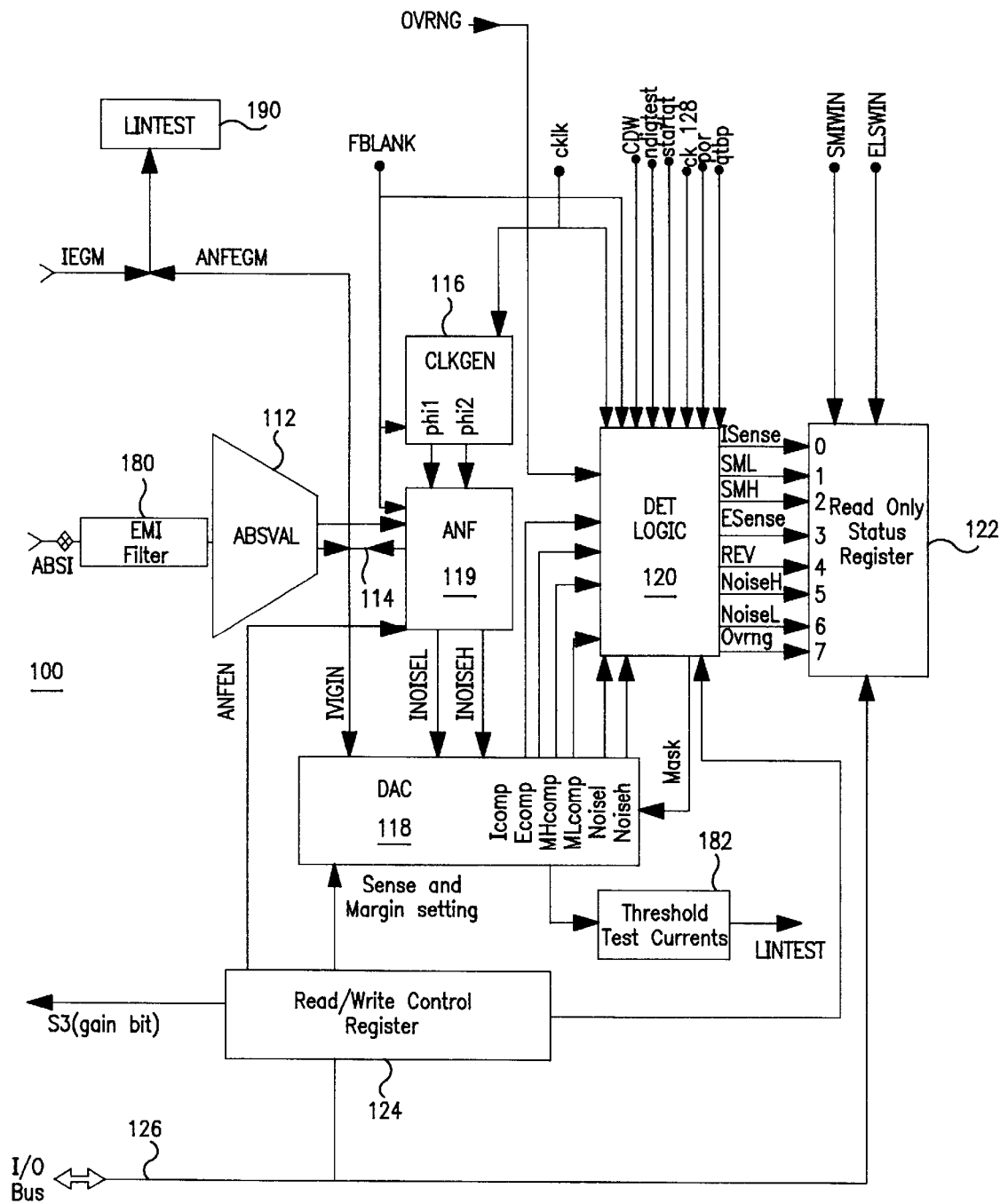

FIGS. 2 and 3, depict a preferred embodiment of a sense amplifier circuit 100, incorporating a read/write sensitivity control register 124 (FIG. 3.) and read only status register 122, that may be used (in the diagram of FIG. 1) for the atrial or ventricular sense amplifiers 38A and 38V and the associated sensitivity control circuits 124A and 124V and read only status registers 122A and 122V, respectively. A main circuit distinction between the atrial and ventricular sense amplifiers 38A and 38V is the value of resistor 102. The ventricular sense amplifier resistor 102 value is preferably one-half the atrial sense amplifier resistor 102 value in order to provide an atrial channel gain range twice the ventricular channel gain range though other values can be chosen to extend or lower the gain range. Other differences in comparator values, for example, are programmed into the microcomputer 34 and are used in the read/write control register 124 for each IPG circuit 30 as described above.

The sense amplifier circuit 100 (for the atrial and ventricular sense amplifiers 38A and 38V) depicted in FIGS. 2 and 3 include a front end circuit as illustrated in the area of bracket 104, a differential amplifier (DIFFAMP) 106, a capture (evoked response) detection circuit (CDHW) 108, a bandpass filter transimpedance amplifier (TRANSAMP) stage 110 for rejecting unwanted signals, a rectifying circuit (ABSVAL) 112 for converting the differential signal to a single ended one, an Analog Noise Filter (ANF) 114 to reject continuous wave noise, a clock generator (CLKGEN) 116, a series of digital amplitude comparators (DAC) 118, and detection logic (DETLOGIC) 120. The read/write control register 124 and read only status register 122 are also shown in FIG. 3 to illustrate the data and control interconnections of the sense amplifier circuit 100 with the digital controller/timer 40.

The read only status register 122 shown in FIG. 3 stores the identified sense amplifier DETLOGIC 120 output signals as bits in the atrial or ventricular sense amplifier context. The bits relative to intrinsic sensing associated with a particular address are the intrinsic sense (ISENSE, which may be an AISENSE or VISENSE) depending on whether this is a Atrial or Ventricular implementation, the sense margin low (SML) and sense margin high (SMH) bits, the noise floor exceeded low (NOISEL) bit, the noise floor exceeded high (NOISEH) bit, the common-mode over-range bit (OVRNG) bit, and the reversion (REV) bit. An evoked response sense (ESENSE) bit is also stored in a specific register stage address.

The SML and SMH bits characterize the magnitude of the peak amplitude of the non-refractory intrinsic sense (ISENSE) event relative to the current sensing threshold $I_{TH}$ setting. The measurement of sensing margins is accomplished during a Sense Margin Indicator (SMI) window timed out in digital controller/timer circuit 40 and shown in FIGS. 10–12 in a manner described below in detail. The SMH and SML bits are latched in bit stages of read only status register 122 at the end of the SMI window.

An Excessively Long Sense (ELS) timing window maybe used in one embodiment the ELS is timed out in the digital controller/timer circuit 40 as a means of preventing the AutoSensing algorithm from adjusting the sensitivity in response to ISENSE signals that are not likely to be physiologic in origin. When a non-refractory ISENSE is detected, the duration of the signal is effectively compared against the ELS window to insure that the duration does not exceed a value that would be expected to be reasonable for an intrinsic cardiac signal.

At the end of the ELS window, the reversion status indicated by the REV bit is latched in a REV bit stage of the read only status register 122. If the current sense event is non-physiologic (i.e., excessively long in duration), the REV bit will remain high at the end of the ELS window, and the current ISENSE event will be treated as invalid in the AutoSensing algorithm.

Additionally, a means to determine if a subsequent sense event falls within the ELS window is provided to terminate the ELS (Excessively Long Sense) window as described below with respect to FIGS. 10–12. A signal ELSEVNT indicating an Excessively Long Sense Window Event) is accessible through a readable register located preferably in the controller circuit 40 (FIG. 1). We call it a Sensing Assurance Control Register (SACR) and use it to hold an indicating signal "JA" when a sensed event occurred outside the SMI (Sense Margin Interval) but inside an ELS window. (Obviously if the particular embodiment doesn't use an ELS window, it won't use an SACR either.) The status in the SACR reflects the most recent non-refractory event and is cleared upon reading the SACR register as described below in reference to FIGS. 11 and 12.

Control of the sense amplifier circuit 100 functions is achieved through data stored in the read/write control register 124. Read/write control register 124 is accessible over the I/O bus 126 which communicates with the data and control bus 56 of FIG. 1 through digital controller/timer circuit 40.

A number of other timing and control signals affecting the operation of various parts of the sense amplifier circuit 100 are typically generated from or passed through the digital controller/timer circuit 40 on the TIMING lines of FIG. 1 and are described in the following more detailed description of the components and functions of each sense amplifier circuit 100.

Front End Circuit 104

The front end circuit 104 in FIG. 2 connects to the pace/sense lead TIP and RING terminals and the − and + inputs of DIFFAMP 106 respectively. (Other electrodes could be used in alternate embodiments). A reference voltage (VR) generated by the INREF (Input Reference Voltage) circuit 152 at approximately 600 mV below the analog ground (AVDD) which is also applied to the front end circuit 104 and, in unipolar sense modes, is coupled to the + input of DIFFAMP 106 as described below. IPG case is also connected to the reference voltage "VR."

The front end circuit 104 responds to a number of timing and control signals or intervals, namely the UR, (Unipolar Ring) UT, (Unipolar Tip) IBLANK, (Current blanking) and CLRSPSM (clear the "SP" and "SM" inputs) signals or intervals, and the attenuation ENATTEN (Enable Attenuator) signals provided to the on-chip attenuators 134 and 136, respectively. These attenuators may be independently gain controlled as well to reduce the input signals to amplifier 106 as a calibration mechanism. The opportunity for inhibition from downlink telemetry bursts is reduced by the downlink filters 130 and 132 which preferably each comprise a cascade of two low-pass filters formed from on-chip resistors and capacitors.

The TIP and RING terminals are coupled to the downlink filters 130 and 132 via series capacitors 140 and 142, respectively on SP and SM bond pads, respectively, and through a BLANKING switch network 144 and a unipolar/bipolar configuration switching network 146. Two on-chip shunt resistors 148, 150 provide a DC bias point in relation to voltage reference VR and form a high pass filter in conjunction with the series capacitors 140 and 142.

Normally closed switches 153 and 155 couple the shunt resistors 148 and 150, respectively, to VR. Switches 153 and 155 are opened by the NCDSFW (Non Capture Detect Slew Filter Window) signal from digital controller/timer circuit 40 in order to support capture detection. The NCDSFW signal is commenced when capture detection testing is desired. During Auto Sensing these switches are closed. These functions are usually exclusive in a well-functioning IPG (Implantable Pulse Generator).

Figure 4:
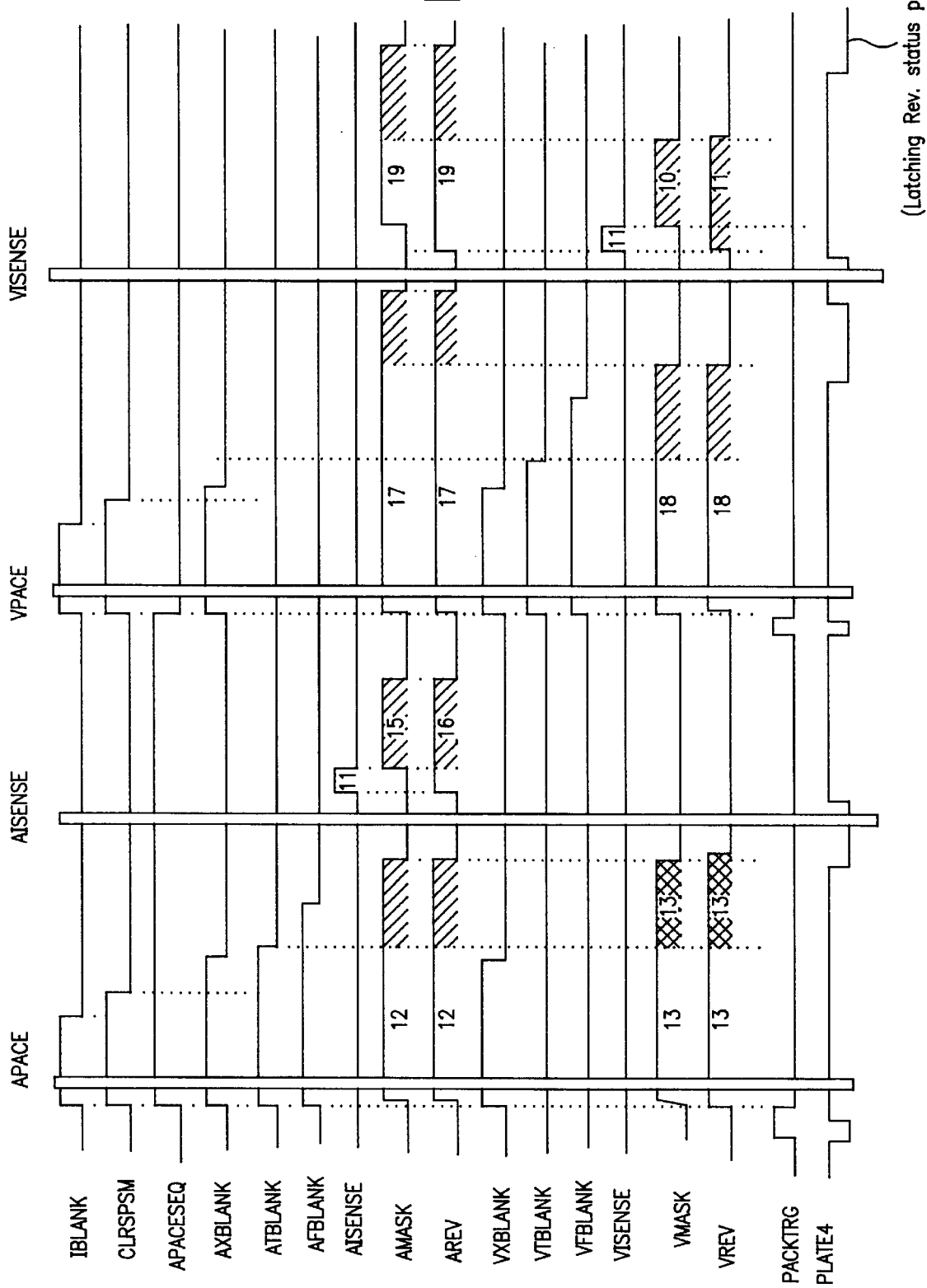
FIG. 4 is a timing diagram of blanking and reversion logic signals used in the sense amplifier of FIGS. 2 and 3 and associated with intrinsic sensed and paced events.

To prevent the sense amplifier circuit 100 from responding excessively to the delivery of an A-PACE or V-PACE pulse or becoming "blinded" by them a set of series and shunt p-channel switches form the BLANKING switch network 144 and are used to decouple the DIFFAMP 106 − and + inputs from the TIP and RING terminals and short the DIFFAMP 106 inputs to the voltage reference VR during the blanking interval of a pacing sequence. The IBLANK signal is generated by the digital controller/timer circuit 40 and applied synchronously with the respective A-TRIG or V-TRIG signal to open the series switches 145, 149 prior to the A-PACE or V-PACE pulse interval and to re-close them when the RECHARGE operation times out. The shunt p-channel switches 147, 149 are closed by the CLRSPSM signal to short the DIFFAMP 106 + and − inputs to the voltage reference bias VR during the IBLANK interval and for a short interval thereafter to thereby prevent any extraneous DIFFAMP output signal due to possible transients. The operation of the IBLANK and CLRSPSM controlled switches 147, and 149 is also coordinated in a fashion to re-establish the DC bias point on the coupling capacitors 140 and 142 after a RECHARGE operation by connecting capacitors 140, 142 directly to the voltage reference VR, thereby minimizing any re-coupling artifact. The CLRSPSM timing signal is also depicted in FIG. 4 in relation to the A-PACE and V-PACE pulses.

In pacemakers of this type, the lead and electrode configuration can be selected to either a unipolar configuration, wherein the RING terminal or clasp electrode is electrically connected to the reference voltage VR, or the bipolar configuration shown in FIG. 2. Each sense amplifier 38A and 38V is therefore independently capable of sensing in either unipolar (tip-to-case or ring-to-case) or bipolar (tip-to-ring) configurations and accepts both positive and negative polarity input signal pulses. The sensing configuration of the particular sense amplifier circuit 100 is determined by the unipolar/bipolar configuration switch network 146 in the sense amplifier front-end 104 that are controlled by the states of signals UR and UT. The IPG case is grounded at AVDD for all three configurations and is high impedance to AVDD only during bipolar A-PACE/V-PACE and RECHARGE operations.

When neither the UR or UT signals are present (UR, UT=not asserted), the series p-channel switches 157 and 159 are closed, and the shunt switches are open, resulting in the TIP to RING bipolar sensing configuration. When the UR signal is "asserted" and the UT signal is "not asserted", then the TIP input is effectively un-coupled from the downlink filter 130, and the downlink filter 130 is coupled to VR at the output of INREF 152 through closed switch 161, resulting in unipolar ring sensing. Similarly, when the UT signal is "asserted" and the UR signal is "not asserted", then the RING input is effectively uncoupled to the downlink filter 132, and the downlink filter 132 is coupled to VR at the output of INREF 152 through closed switch 163, resulting in unipolar tip sensing depicted in FIG. 2.

Each sense amplifier circuit 100, when used as atrial and ventricular sense amplifiers 38 and 39, is independently capable of being powered down. With three sensing configurations controlled by two states of two signals (UR and UT) the remaining logical combination (UR, UT=asserted) is used to set the sense amplifier POWER DOWN mode. In FIG. 2, this would result in the TIP and RING terminals being uncoupled from the − and + inputs of DIFFAMP 106 and their coupling instead to the VR potential.

The ability to test the most sensitive setting of the sense amplifier circuit 100 is enhanced by the on-chip attenuators 134 and 136 that permit larger than desired signals to be applied to the TIP and RING terminals and then attenuated right at the DIFFAMP 106 inputs to enhance the signal-to-noise ratio. The attenuators 134, 136 are formed by resistive voltage divider circuits created by the series downlink filter 130, 132 resistance and a further shunt resistance to the input voltage reference VR. The attenuators 134, 136 are enabled by the signal ENATTEN which turns on a p-channel switch in series between the shunt resistance and the DC voltage reference VR to provide an attenuation ratio of 20:1. This feature is only used during testing and is not related specifically to the present invention.

DIFFAMP 106

The DIFFAMP 106 performs a differential-to-single-ended conversion of the signals passed through the front end circuit 104 and applied to its + and − inputs. The DIFFAMP 106 is a transconductance amplifier having a transconductance that is inversely proportional to the value of the resistor 102. Resistor 102 is preferably a multimeg-or-kilohm resistor, so if on-chip we prefer a CrSi composition resistor. The transconductance has two different values: 5/R, where R=[lo_gain, hi_gain] and is selected along with sensing threshold ($I_{TH}$) of the DAC 118 by a gain bit value written into read/write control register 124. The gain bit value is transferred by read/write control register 124 to DIFFAMP 106 on a control line 158. This arrangement creates a two stage front end gain control scheme which allows for a limited size back-end ranges of sensitivity.

Over Range

The DIFFAMP 106 provides an analog output signal representative of the patient's EGM as picked up by the pace/sense electrodes coupled to the + and − inputs through the setting of the switch network 146 so long as the signal level does not exceed an "over range" level. As an indication of its operating status, each sense amplifier circuit 100 therefore provides an independent indication that the input to the amplifier TIP and RING terminals has exceeded its input range in either intrinsic or evoked response sensing. The OVRNG signal is a digital 1-bit signal provided by the DIFFAMP 106 when the signal levels at the inputs thereof exceed the common mode or differential mode over-range threshold, e.g. 400 mV, and is applied to the DETLOGIC (Detection Logic) 120. DETLOGIC 120 responds by setting the OVRNG
(over-range) bit in bit stage 7 of the read only status register 122.

The over range status for either sense amplifier is accessible to the digital controller/timer 40 by reading the OVRNG bit that is set in read only status register 122. The OVRNG bit status reflects whether or not an over range condition has occurred since the last time bit stage 7 was read and is cleared upon reading the register stage. While the over range situation exists, the sense amplifier circuit 100 does not output any indication of an ISENSE event. However, if the OVRNG state occurs during the Autosensing algorithm response to a preceding ISENSE event, it is taken into account.

The autosensing algorithm takes it into account only after an ISENSE is detected. This can be seen with reference to 16.

IEGM/ANFEGM Telemetry

Assuming that the over range condition is not present, the DIFFAMP 106 provides a current output signal (IEGM) tracking the amplitudes of the atrial or ventricular EGM (Electro-Gram) which is sent through a node 111 with the ANFEGM (Analog Filtered EGM) signal in a LINTEST (Line Test) operation of digital controller/timer 40. The LINTEST operation is effected by a linear test multiplexor buffer that allows observation of several analog signals, one at a time, at an external IC pad. The ANFEGM signal is a copy of current signal IVIGIN (the sum of IEGM and ANFEGM) provided to DAC 118 by ANF 114 and ABSVAL 112, as described below. A programmed-in command communicated through I/O bus 126 and read/write control register 124, initiates ANFEGM signal delivery to the digital controller/timer 40. Both the ANFEGM and the IEGM signals may be processed to match the input range of the delta-mod converter of ADC and multiplexer 52 for telemetry out. This allows the user to observe the actual post-ANF (Analog Filter) processed signal that is being employed in the comparator functions of the DAC 124 in relation to the IEGM.

DIFFAMP Output Signal

A separate sense signal output of the DIFFAMP 106 that is in range (and related to the IEGM signal by virtue of their shared input processing) is filtered (EMI filter 166) and applied to the input of TRANSAMP stage 110. The output of DIFFAMP 106 is loaded with a 400 Kohm CrSi resistor 102 for the ventricular sense amplifier 38 and with an 800 Kohm CrSi resistor 102 for the atrial sense amplifier 39. To set the voltage gain of the DIFFAMP 106, a filter capacitor 154 may be coupled across the resistor 102 that has a value of 3.3 nF for the atrial sense amplifier 38 and 6.83 nF for the ventricular sense amplifier 39, for example.

Evoked Response/Capture Detection

It is possible to configure the sense amplifier circuit 100 to detect the presence of the cardiac evoked response (i.e., the response of the atrial or ventricular cardiac tissue contracting in response to the delivery of a pacing pulse). Capture detection is the ability to determine whether or not the delivered A-PACE/V-PACE pulse caused the myocardium to contract. This detection is accomplished by the Capture Detect Hardware Circuit (CDHW) 108 across the series resistor 162 biased through capacitors 105 and 107 by the VREG and AVDD signals. Active recharge circuitry in the pacing output circuit 36 (FIG. 1) makes capture detection more viable by reducing the "after potential" at the electrode-tissue interface. The main challenge of capture detection has been to discriminate the evoked response from the after potential created by the tissue-electrode interface. The CDHW 108 peak tracks the current output of the DIFFAMP 106 through the resistor 162 and subtracts the peak tracked after-potential. The resulting current signal at the junction of capacitors 154 and 164 are signal deflections in the opposite direction of the peak tracking signal deflections. The evoked response signal deflections are processed and result in the generation of the ESENSE (Evoked Sense) output signal of the DETLOGIC (Detection Logic) 120 in the same manner that the ISENSE output signal of DETLOGIC 120 is generated. The capture detection operation and resulting ESENSE bits do not play a role in the AutoSensing algorithm of the present invention and are not described further in any detail.

Bandpass Filter (TRANSAMP) Network Description

The evoked response or intrinsic output of the DIFFAMP circuit 106 at the junction of capacitors 154 and 164 so is subsequently processed in TRANSAMP stage 170 through a two-pole bandpass filter network constructed around transconductance amplifier (TRANSAMP) 170. The high-pass filter poles are determined mainly by the input series capacitor 164 and the output series capacitor 168. The low-pass filter poles are determined mainly by the front-end differential capacitor 154 and the output shunt capacitor 172. The off-chip capacitors 168 and 172 have their corner frequencies predominantly determined by the resistor 102. The filters' structures are the same for both the atrial and ventricular sense amplifiers 38A and 38V. A further EMI filter 166 similar to downlink filters 130, 136 is placed in the input to the TRANSAMP 170.

The feedback resistor 174 across the TRANSAMP 170 is shunted by a p-channel switch 176 as part of the sense amplifier blanking scheme. This p-channel switch 176 is controlled by a TBLANK (Transamp Blanking) or an XBLANK (Blanking signal to the Transamp of the other chamber) timing signal shown in FIG. 4 and effectively attenuates the signal through the bandpass filter network associated with the TRANSAMP stage 110. The XBLANK and TBLANK intervals extend beyond the IBLANK and CLRSPSM intervals and are programmable in length or could be set automatically. The AXBLANK (Atrial cross Blanking) and VXBLANK (Ventricular cross Blanking) signals are provided to close both switches 176 in both the atrial and ventricular sense amplifiers 38A and 38V in response to an A-PACE or a V-PACE. The relatively longer ATBLANK or VTBLANK signals are only applied to the switch 176 of the atrial or ventricular sense amplifiers 38A or 38V, respectively, in response to the A-PACE or V-PACE pulses. All of these blanking intervals time out in a cascade as shown in FIG. 4 to prevent any re-connection artifacts from propagating through the sense amplifier circuit 100.

Rectifier (ABSVAL) Circuit Description

The output current signal of the TRANSAMP stage 110 is connected to the input of a low input impedance current rectifier, absolute value (ABSVAL) circuit 112 through the off-chip resistor 178 and a further EMI filter 180. One purpose of ABSVAL circuit 112 is to convert its input signal to a single ended signal and to thereby remove any sensitivity to the signal polarity.

Analog Noise Filter (ANF) 114

The ANF 114 is a current mode, peak tracking circuit responsive to the ABSVAL 112 output signal for providing a peak detected output signal filtered through a low-pass, switched-capacitance filter. The CLKGEN circuit 116 supplies 1 kHz non-overlapping clocks (PHI1 and PHI2) for the switched-capacitance filters. An ANF (enable) signal is provided by the read/write control register 124A or 124V to enable the ANF 114 of each respective sense amplifier 38A or 38V.

An AFBLANK (Atrial Filter Blanking) signal or a VFBLANK (Ventricular Filter Blanking) signal is generated response to an A-PACE pulse or a V-PACE pulse, respectfully, as depicted in FIG. 4, to blank out signals that would otherwise be received immediately after a pacing pulse.

All of the pulses in FIG. 4 are triggered by the PACETRIG (Pacing pulse trigger) signal unless it occurs during a reversion period that is unlatched by the PLATCH (Pace latching) signal.

The shaded pulses indicate the length of that interval is retriggerable at anytime during the shaded area by its input signal and will fall at a defined time (eg 30 m secs) after the input signal is quiet. The cross hatched pulses indicate a "quiet timer" which is only started if the quiet timer was active prior to the initiating a pace. In other words, if it had not yet timed out its 30 ms of quiet by the time the pace occurred, a new quiet timer period will be started following the post-pace blanking.

One object of the ANF 114 is to produce a DC current signal value having a magnitude that is proportional to the peak signal amplitude of any continuous incoming noise in the output signal of the ABSVAL 112 when the FBLANK signal is low or absent. This continuous noise floor signal is then subtracted from a second signal output of the ABSVAL circuit 112 with the intent of eliminating the portion of the signal that is due to the continuous noise signal. The result of this subtraction process is a current signal IVIGIN that is fed into the input of the threshold comparators in DAC 118. In this manner, only spontaneous events whose magnitude is greater than that of the noise source (i.e., hopefully cardiac events) will be passed along to the threshold comparator circuits in DAC 118.

In addition to its use in generating the IVIGIN signal, the continuous noise floor signal is compared to a noise floor high threshold and a noise floor low threshold to provide IVNOISEH and IVNOISEL signals to a comparator circuit in DAC 118.

Figure 5:
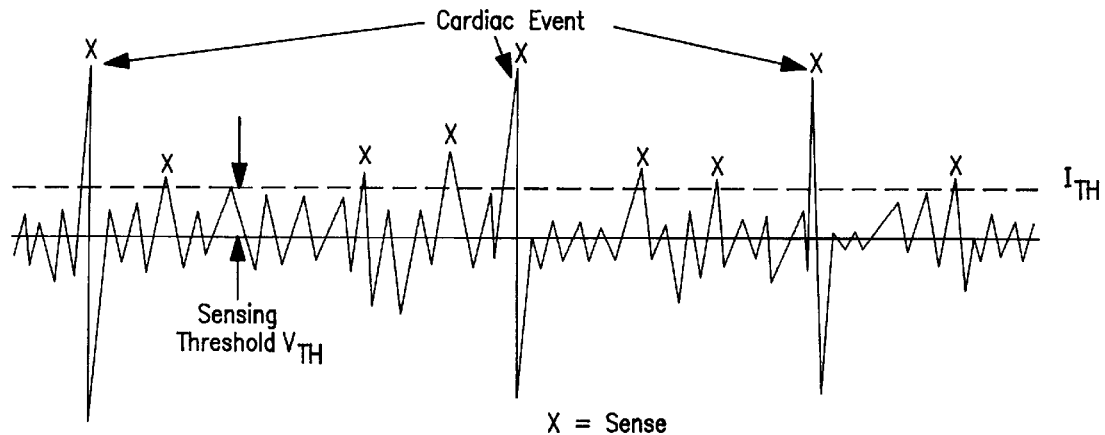
FIG. 5 is a diagram of oversensing of noise and cardiac event peaks occurring in the presence of continuous noise due to a fixed sensing threshold.
Figure 6:
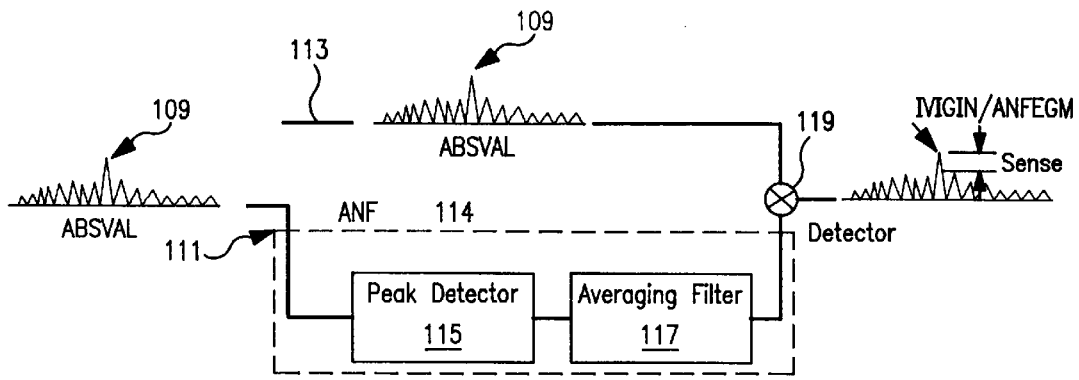
FIG. 6 is a schematic block diagram of the components and functions of an analog noise filter employed in FIG. 3.

To illustrate the purpose of the ANF 114, consider the situation depicted in FIG. 5 wherein both cardiac and myopotential signal peaks exceed a hypothetical time invariant sensing threshold $V_{TH}$ (dashed line). Each time that the noise peaks exceed sensing threshold $V_{TH}$, they are sensed, and ISENSE events recur at a rapid rate, resulting in oversensing and inhibition of the pulse generator. To counter this, the ANF 114 operates as a nonlinear adaptive filter to avoid sensing the noise signal peaks as long as they do not exceed the amplitudes of the intrinsic cardiac events. (In preferred embodiments these values are current values rather than voltage amplitudes after the TRANSAMP, but it is much more simply explained this way.) FIG. 6 depicts a simplified schematic block diagram of the ANF 114 functions for processing the output signal 109 of the ABSVAL 112. Two separate rectified signal copies of the ABSVAL signal are provided on signal lines 111 and 113 by the ABSVAL circuit 112 for subsequent processing. The first signal line 111 provides the ABSVAL signal to the ANF 114, and the second signal line applies the ABSVAL signal to a summing node 119 at the output of the ANF 114 also shown in FIG. 3. The output signal of the ANF 114 is also applied as a second signal to the summing node 119.

The ANF 114 includes a peak detector 115 and an averaging filter 117. The peak detected and averaged current signal is subtracted from the un-processed ABSVAL current signal at the node 119. The resulting IVIGIN current signal is applied to the DAC 118. (In addition, a copy of the IVIGIN signal, ANFEGM, is supplied to the LINTEST terminal as described above and can be selected for telemetry out by a "swap EGM" programmable command received through I/O bus 126 and lodged in a stage of read/write control register 124).

When the ABSVAL signal 109 includes continuous noise and intrinsic P-waves or R-waves as shown in FIGS. 4 and 5, it is the peak of the continuous signal detected in peak detector 115 that determines the overall signal average. Therefore, the relatively infrequently occurring cardiac event signals contribute very little to the average. In effect, the peak average signal establishes the noise floor of the incoming signal and is subtracted from the signal 109 to present only the peak signal in the IVIGIN signal to the DAC. The result is depicted in FIG. 7 where few if any of the noise signals are sensed as cardiac events.

Figure 7:
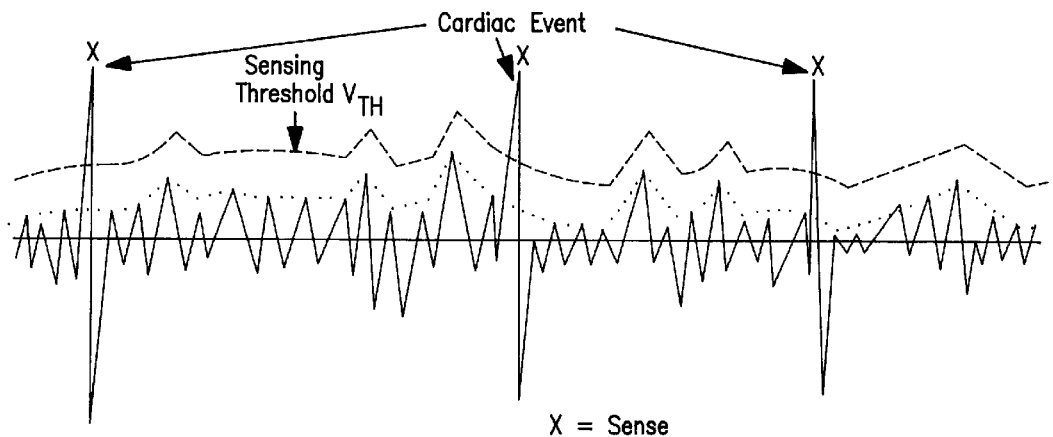
FIG. 7 is a diagram of normal sensing of cardiac event peaks occurring in the presence of continuous noise accounted for by a time varying sensing threshold effected by the analog noise filter of FIG. 6.

It should be apparent from FIG. 7 that as the ANF 114 responds to the peak of the continuous noise, there is a corresponding loss of sensing margin. The sensitivity adjusting algorithm of the present invention as described below would then retroactively decrease the sensing threshold (i.e., increase the sensitivity) in an attempt to maintain a more effective margin. However, it will only do so until the excessive noise floor situation is encountered (see discussion of excessive noise condition below). This will insure that the sensitivity does not follow the cardiac signals right down into the noise floor.

Even though the ANF 114 acts to track the amplitude of a continuous noise signal, thereby minimizing the detection of that signal, spiked or spurious events (e.g., spikes in myopotential signals) may occasionally still be sensed. This occurs because spurious events contribute little to the signal average (in just the same manner as the cardiac event itself does not) and their amplitudes may exceed the sensing threshold. Furthermore, the probability that a cardiac event will exceed the sensing threshold in the presence of continuous noise is dependent on the relative phase of the cardiac event and the continuous noise source. In other words, if the noise source signal and the cardiac signal interfere constructively, the amplitude of the composite signal will likely exceed the sensing threshold. On the other hand, if the noise signal and the cardiac signal interfere destructively, the amplitude of the composite signal may not necessarily surpass the sensing threshold. Thus, the ANF 114, although offering a significant improvement in noise rejection over time invariant designs, will not eliminate all incidences of noise sensing (particularly in unipolar sensing configurations) and may display incidences of pseudo-undersensing.

Other non-idealities of the ANF 114 include the ripple on the averaged signal (a characteristic typical of peak detect in output levels) and the finite response time of the averaging filter 117. Although the diagrams in FIGS. 5 and 7 depict the averaged peak signal as being fairly smooth, there is, in actuality, a small amount of ripple on the signal that results from the peak tracking nature of the filter 117. The long time constant of the averaging filter 117 helps to reduce this ripple, but it is, nonetheless, still present. As a result of the ripple, the averaged noise signal never really quite reaches the actual peak of the noise and always underestimates it. For this reason the gain of the signal through the ANF signal path between the peak detector 115 and the averaging filter 117 is set to a value greater than 1, preferably 1.2 in order to make up for the shortfall and prevent the systematic ripple from entering the threshold comparators of DAC 118.

Another aspect of the ANF 114 that is not apparent from FIGS. 5–7 is the time required for the ANF 114 to respond to peak changes in the incoming signal. A slow response time is required to prevent the ANF 114 from responding to short transient events like P-waves and R-waves. A long response time is also necessary to allow the ELS window check described below to have an opportunity to recognize that the incoming signal is not an intrinsic event. The delay from the start of a 60 Hz continuous noise signal until the averaged noise signal reaches 10% of the peak noise amplitude is about 125 mS. A total of 200 mS is required to reach the 20% level whereas 600 mS is required to reach the 95% level. Thus, sensing of and/or some loss of sensing at the onset of a continuous noise signal or due to noise bursts will occur. However, the ELS window check aids in keeping inappropriate margin measurements out of the sensitivity adjusting algorithm.

Finally, as a by-product of the Analog noise filter (ANF) processing, a measure of the peak noise signal amplitude is produced and compared to two multiples of the sensing threshold $I_{TH}$ (Noise L and Noise H) as a means of determining when an excessive noise condition exists. The two multiples are fed by ANF 114 to the DAC 118 for comparison to the outputs from register 124 (MH comp.& ML comp.)

The signals for comparison are sent to DETLOGIC 120 on lines INOISEH and INOISEL (for Input Noise Hi, and Low) that are used as part of the qualification process to determine whether or not a sensing margin measurement should be considered valid by the adjustment algorithm.

Comparator Circuit (DAC) Description

A set of bias current mirrors within DAC 118 scale the main sense amplifier bias current supplied by a power supply in digital controller/timer circuit 40 to supply bias currents for all the other circuit blocks within the sense amplifier circuit 100.

The DAC 118 also comprises five separate current comparators that compare the instantaneous current peak value of the IVIGIN intrinsic sense signal against five current values of thresholds used in the AutoSensing algorithm described below. The five current comparators generate one or more of the corresponding Icomp, MLcomp, MHcomp, "high" output signals when the intrinsic sense IVIGIN signal exceeds one or more of the thresholds and NOISEH or NOISEL when they exceed their predetermined thresholds. When the CDHW 108 is enabled or programmed "ON", the IVIGIN signal is compared in a further comparator to a capture detect threshold, resulting in the Ecomp signal, when the comparison results are positive or "high".

In this regard, the current sensing threshold $I_{TH}$ level for the intrinsic event comparator determines the sensitivity of the sense amplifier circuit 100. The baseline current sensing threshold $I_{THb}$ is programmable by the physician within a given range, stored in memory in microcomputer 34, and transferred through I/O bus 126 to stages in read/write control register 124. The current sensing threshold $I_{TH}$ is then updated in accordance with the AutoSensing algorithm described in detail below by the microcomputer 34 using "set" bits from certain stages of the read only status register 122 that are read out under certain conditions on I/O bus 126.

The sense margin high and sense margin low comparators compare the IVIGIN signal against margin high (MH) and margin low (ML) threshold levels that are multiples of the current sensing threshold $I_{TH}$ as described below with reference to FIG. 8. The multiplier values are also programmed into memory associated with microcomputer 34. The MH and ML threshold levels are calculated therefrom in microcomputer 34 and are forwarded to and stored in stages of read/write control register 124. The ML threshold is always greater than the current sensing threshold $I_{TH}$, but less than the MH threshold thereby defining an adequate sense (AS) as described in detail below with reference to FIG. 9.

The evoked response comparator in DAC 118 is used to detect an evoked response signal in the post-pace waveform during a Capture Detection Window (CDW) applied to DETLOGIC 120. The evoked response threshold level is also independently programmable within a given range, the programmed value stored in memory in microcomputer 34, and then calculated as a current value and stored in a stage of read/write control register 124. The resulting ESENSE signal is generated in DETLOGIC 120.

The INOISEH and INOISEL signals provided by ANF 114 are compared in NFLCOMP (Noise floor) comparators in DAC 118 against high and low noise floor thresholds, which are multiples of the current sensing threshold $I_{TH}$, as a means of determining when an excessively noisy signal or a tolerable noisy signal is present. The low noise floor threshold is fixed at $2 \times I_{TH}$, and the high noise floor threshold is fixed at $8 \times I_{TH}$. DETLOGIC 120 responds to positive comparison signals NOISEH and/or NOISEL by providing the respective NOISEH and/or NOISEL signals to respective bit stages 5 and 6 of read only status register 122.

Detection Logic (DETLOGIC) Description

The screening of the logical outputs from the DAC 124 is performed by the DETLOGIC 120 which is subdivided into two sections that deal with the evoked response comparator output (Ecomp) and the intrinsic event comparator outputs Icomp, MHcomp, MLcomp, NOISEL, NOISEH. Additional logic is provided to enhance testability of the circuits in DETLOGIC 120. NDIGTEST is a digital input signal that, when asserted by digital controller/timer circuit 40, indicates that the digital test mode of operation has been invoked. The initial logical state of the DETLOGIC 120 circuitry is determined by temporarily asserting the POR signal.

There is a 1 mS minimum signal duration and a minimum signal amplitude required for an input signal to DETLOGIC 120 to be considered a detected event (either intrinsic or evoked). The minimum signal amplitude is determined by the sense amplifier current sensing threshold $I_{TH}$ which varies as described below from a base sensing threshold $I_{TH}$ that is independently programmable as a PDS for either chamber and for intrinsic and evoked detection. The current sensing threshold $I_{TH}$ levels apply to either polarity input signal in any sensing configuration.

Therefore, the first operation the DETLOGIC 120 performs on the intrinsic response Icomp signal is to screen its high output state to determine that it persists for the minimum duration of 1 mS using the 1 kHz clock. The detection of an intrinsic event of sufficient duration is indicated by the rising edge of the logic high ISENSE output signal which remains high as long as the Icomp comparator level set by the current sensing threshold $I_{TH}$ is exceeded by the IVGIN current signal level. In the dual chamber pacemaker context, ISENSE is AISENSE in atrial sense amplifier 38A and VISENSE in ventricular sense amplifier 38V.

NOISE Response of DETLOGIC 120

The noise comparator outputs NOISEL and NOISEH from DAC 118 are also processed in DETLOGIC 120 and latched as NOISEL and NOISEH bits in bit stages 5 and 6 of the read only status register 122. The latching of the NOISEL and NOISEH bits occurs whenever the noise thresholds are exceeded. The NOISEL and NOISEH bits are read out following the SMI interrupt generated when the ELS window (ELSWIN) expires as described below with reference to FIGS. 10–12 if the particular Embodiment uses a ELS window. Otherwise it is read out when a predetermined time similar to what ELS time would be gets clocked into a timer. Further adjustment of the current sensing threshold $I_{TH}$ by the AutoSensing algorithm described below is suspended until the excessive noise situation subsides. In one embodiment we don't use the NOISEH signal instead NOISEL information is used to invalidate sensed events by preventing adjustment of $I_{TH}$ in the presence of suspected noise.

Reversion Logic

"Reversion" in the context of the present invention is the situation where the current sensing threshold $I_{TH}$ is constantly exceeded by the incoming IVIGIN signal (i.e., some extraneous noise source that may not necessarily exceed the NOISEL or NOISEH thresholds). Rather than inhibit the pulse generator by constantly resetting the pacing escape intervals, this condition is detected, and the reversion mode is initiated. In this reversion mode, the pulse generator lower rate or prevailing physiologic sensor determined escape interval is not reset, and A-PACE and/or V-PACE pulses are delivered at the ends of the escape intervals that are programmed into operation at the corresponding pacing atrial and/or ventricular pacing rate.

FIG. 4 depicts the normal timing and expiration of the reversion signal time periods under the four possible situations where the capture detector CDHW 108 is not enabled and in the absence of recurring VISENSE (Ventricular Intrinsic) or AISENSE (Atrial Intrinsic) signals. FIG. 4 also depicts the (A) and (V) IBLANK, TBLANK, XBLANK, FBLANK, CLRSPSM, signal time periods for the atrial (A) and ventricular (V) sense amplifiers 38 and 38V that are described above and are applied by the digital controller/timer circuit 40 to the sense amplifier circuit 100 just prior to the delivery of an A-PACE or a V-PACE. Referring back to FIG. 3, the digital controller/timer circuit 40 also provides the Start Quiet Time (STARTQT) signal to the reversion logic in DETLOGIC 120 of both atrial and ventricular sense amplifiers 38A and 38V. The initial portions of the AMASK and VMASK (Atrial and Ventricular Masking) intervals shown in FIG. 4 correspond to the ATBLANK or VTBLANK intervals and ensure that the bandpass filter network associated with TRANSAMP stage 110 has stabilized before its output signal (processed by the ABSVAL circuit 112) is sampled.

The REV bit is set "high" in bit stages 4 of read only status registers 122A and 122V for each affected sense amplifier circuit 100 of the atrial and/or ventricular sense amplifiers 38A and 38V. The REV bit remains present in bit stage 4 of the read only status register 122A or 122V for the duration of the "high" AREV or VREV (Atrial or Ventricular Reversion) signal and any extensions of the "high" AREV or VREV signals re-triggered by repeated AISENSE and/or VISENSE events. The REV signals go back low at the ends of the depicted REV intervals unless they are extended in this fashion. The high or low state of REV bit stage 4 is read out or sampled at the SMI interrupt at the end of further ELS window shown in FIGS. 10–12. The ELS window commences with an initial ISENSE event and exceeds the REV duration for that ISENSE event. Therefore, for a normal duration sense event, the REV bit would be low when the REV bit stage 4 is interrogated at the end of the ELS window.

As shown in FIG. 4, a V-PACE, A-PACE or VISENSE event triggers the time out of AREV and VREV intervals and associated AMASK and VMASK intervals, whereas the AISENSE event only triggers time-out of the AREV and AMASK intervals. With respect to a VISENSE event, for example, the digital timing and control circuit 40 responds to the VISENSE interrupt from I/O bus 126V by providing the STARTQT signal to DETLOGIC 120 of both sense amplifiers 38A and 38V. The reversion logic in DETLOGIC 120 is then enabled in both the atrial and ventricular sense amplifiers 38A and 38V during Quiet Time (QT) intervals corresponding to the AREV and VREV intervals shown in FIG. 4 depicted in relation to the VISENSE event. The AMASK and VMASK signals (also shown in FIG. 4) are simultaneously generated and applied to the atrial and ventricular sense amplifier DAC 118 in order to affect the sensitivity of the Icomp comparison(s) that take place during the SMI window as described below.

With respect to an AISENSE event, it is generated in DETLOGIC 120 whenever the Icomp comparator output signal of atrial sense amplifier 38A goes high, signifying that the processed atrial IVIGIN signal exceeds the current atrial sensing threshold $I_{TH}$ as an indication of the intrinsic P-wave detection. The AISENSE event is latched in the bit stage 1 of the read only status register 122A, and the AISENSE interrupt is received by digital controller/timer circuit 40. The STARTQT interval is only provided to the reversion logic in DETLOGIC 120 for the atrial sense amplifier 38A, resulting in the generation of the AREV and AMASK signals only, in this case.

Whenever the AREV or VREV signal generated by the reversion logic is "high" as shown in FIG. 4, the REV state is set "high" in bit stage 4 in the corresponding read only status register 122A or 122V. The REV state of bit stage 4 is cleared when the AREV or VREV signal goes low, but if the excessively long sense or the noise condition continues, it is set again and can remain set when the ELS window of FIGS. 10–12 times out. While the reversion situation exists, the DETLOGIC 120 does not output any subsequent ISENSE or ESENSE bit indication of a sensed intrinsic or evoked event. If the embodiment under consideration employs a reversion mode, then during the reversion mode, the NOISEH, NOISEL, SML (Sense Margin Hi) (Sense Margin Lo) and SMH bits are provided to the read only status register 122, although the SML and SMH bits are meaningless in the reversion situation.

The reversion logic in DETLOGIC 120 is also responsive to the occurrence of a common-mode over-range condition signified by the OVRNG signal from DIFFAMP 106. For the duration of the OVRNG signal, the reversion logic blocks the generation of any ISENSE signal to set the read only register 122 bit stage 1.

In both the atrial and ventricular sense amplifiers 38A and 38V, the QT (Quiet Timer) interval counter in DETLOGIC 120 is restarted and the ISENSE output is suppressed if a subsequent transition of the Icomp output signifying an intrinsic event occurs while the appropriate REV signal is high. When this occurs, the REV signal(s) is restarted and the ISENSE output signal of DETLOGIC 120 is not generated. The lower rate timer in digital timing and control circuit 40 times out, and the pacemaker operates in the reversion mode due to the absence of the ISENSE bit interrupts.

To increase the probability that the intrinsic event has truly ended before the QT counter (in DETLOGIC 120) times out, the Icomp comparator has a hysteresis function that is switched on by the MASK signal. This function temporarily decreases the current sensing threshold $I_{TH}$ level (i.e., increases the sensitivity) by 50% until the QT counter times out during the application of the MASK signal. This reduces the IVIGIN signal amplitude requirements to less than half of the current sensitivity setting for the duration of the QT or MASK interval. The hysteresis function can be enabled or disabled by external programming through a bit stored in the read/write control register 124 enabling or disabling, respectively, gate logic between the MASK input and the ICOMP comparator.

Sense amplifier reversion is frequently caused by EMI or myopotentials as shown in FIG. 5 that mask the intrinsic PQRST complex. The sense amplifier circuit 100 has several mechanisms described to this point to prevent the output of these bits in response to the presence of continuous EMI sources. The DETLOGIC 120 provides the NOISEH and NOISEL signals that set the bit stages 5 and 6, respectively, of read only status register 122 in response to the NOISEH and NOISEL outputs of the high and low NFLCOMP comparators, respectively. The noise floor status signified by these bits reflects whether or not the noise amplitude has exceeded the current sensitivity setting since the last time the read only status register 122 was read, and the bit stages 5 and 6 are cleared upon reading the stages after the end of the ELS window.

The NOISEL status of bit stage is used as part of the AutoSensing sensitivity adjustment algorithm to determine when it is appropriate or not appropriate to adjust the sensitivity. If the noise amplitude exceeds twice the current sensing threshold $I_{TH}$ setting, it would not be prudent to adjust the sensitivity, as it may be possible to adapt to the noise source rather than to the desired cardiac signal.

In FIG. 4, the above described timing intervals associated with the A-PACE, V-PACE, AISENSE and VISENSE events (dark vertical lines) are shown without regard to any particular sequence of occurrence of the events. The following notes explain the time intervals depicted in FIG. 4.

t1—AISENSE and VISENSE provided by DETLOGIC 120 are a minimum of 1 mS in duration. The timing of the start of these signals depends on the ISENSE line (occurrence of an intrinsic sense) to the left of signal shown.

t2—AMASK and AREV, associated with an A-PACE, extend 7.8 mS * (3.5 to 4.5) beyond the end of ATBLANK. The shading in the extended region indicates that the signals are re-triggerable by any immediately succeeding AISENSE.

t3—VMASK and VREV are coextensive with ATBLANK associated with an A-PACE but are extendible.

t4—VMASK and VREV are extended beyond the falling edge of ATBLANK by an interval of 7.8 mS * (3.5 to 4.5), if the ventricular sense amplifier is reverted just prior to an A-PACE. The cross-hatching indicates that the extended intervals are re-triggerable by any same chamber (i.e., ventricular) sense event (VISENSE) occurring while they are high.

t5—AMASK also commences at the trailing edge of the AISENSE and persists for 7.8 ms * (3.5 to 4.5). The shading indicates that the full interval is re-triggerable by any succeeding AISENSE.

t6—AREV also commences at the leading edge of the AISENSE and persists for a period of 7.8 ms * (3.5 to 4.5) after the falling edge of the AISENSE. The shading indicates that the full interval is re-triggerable by any succeeding AISENSE.

t7—AMASK and AREV also commence at the rising edge of the blanking signals associated with a V-PACE and extend 7.8 ms * (3.5 to 4.5) beyond the falling edge of VREV/VMASK following a V-PACE. The shaded region indicates that the extended interval is re-triggerable by any succeeding AISENSE.

t8—VMASK and VREV are coextensive with TBLANK+7.8 mS * (3.5 to 4.5) associated with a V-PACE. The shaded region indicates that the signal is re-triggerable by any succeeding VISENSE.

t9—AREV and AMASK also commence at the rising edge of a VISENSE and extend for a period of 7.8 mS * (3.5 to 4.5) after the falling edge thereof. The shading indicates that the extended interval is re-triggerable by succeeding AISENSE.

t10—VMASK also commences at the falling edge of VISENSE and extends for 7.8 ms * (3.5 to 4.5). The shading indicates that the full interval is re-triggerable by any succeeding VISENSE.

t11—VREV also commences at the rising edge of the VISENSE and extends for a period of 7.8 ms * (3.5 to 4.5) after the falling edge thereof.

t12—The shading indicates that the extended interval is re-triggerable by any succeeding VISENSE.

Evoked Response DETLOGIC 120 Description

As in ISENSE event detection, DETLOGIC 120 screens the ECOMP comparator output signal to ensure that it persists for at least 1 mS before declaring an evoked response event or ESENSE. Furthermore, the ECOMP output must appear during a Capture Detect Window (CDW) which is generated by the digital controller/timer 40 after the paced event provoking the evoked response. The declared AESENSE and VESENSE signals applied to a stage of read only status register 122 are also of 1 mS duration.

Read Only Status Registers 122

The read only status register 122 include stages for storing each of the ISENSE, ESENSE, SML, SMH, REV, NOISEH, NOISEL, and OVRNG signals in bit stages 0–7 and also contain additional latching logic to provide appropriate inputs on I/O bus 126 to the digital controller/timer circuit 40 and to the microcomputer 34 to perform a sensing assurance function of the AutoSensing algorithm.

In particular, additional logic in read only status register 122 responds to the SMI window (SMIWIN) and the ELS window (ELSWIN) signals to latch the SML, SMH and REV bits on the time-out of these time windows following a non-refractory ISENSE as described below in reference to FIGS. 10–12. The ISENSE and ESENSE bits are latched in bit stages 0 and 3 on their generation by DETLOGIC 120 and are transferred after clock cycle related time delays on I/O bus 126 to digital controller/timer circuit 40 as interrupts. The NOISEH, NOISEL, and OVRNG bits are latched in read only status register 122 when they are generated in DETLOGIC 120 and are read out on I/O bus 126 to microcomputer 34 at the SMI (Sense Margin Indicator) interrupt generated at the end of the ELS window or after an A-PACE or V-PACE. In other words the status register 122 is read because of their interrupt giving the reversion status after pace, from the atrium after an A pace and from Ventricular after a V pace.

When an ISENSE interrupt occurs, the appropriate refractory periods (not shown in FIG. 4) are started in refractory timers in digital controller/timer circuit 40. In addition, the SMIWIN and ELSWIN signals are started in SMI and ELS window timers in digital controller/timer circuit 40 and applied to latching logic in read only status register 122. If the ISENSE occurs during such a refractory period, the same signal processing takes place as explained above, but the digital controller/timer circuit 40 processes such refractory ISENSE events and the related bits of read only register stages 122 in a refractory sense mode and categorizes the events as refractory ISENSE events. In the Autosensing algorithm of the present invention, same channel refractory ISENSE events cannot start the SMI and ELS window timers.

The read only status register 122 may comprise binary flip-flop stages 0–7 in which respective bits 0–7 are set as a function of the high or low state of the indicated signals or "bits" ISENSE, SML, SMH, ESENSE, REV, NOISEH, NOISEL, and OVRNG output by the DETLOGIC 120.

Bit 0 of the register 122 is set "high" in response to the rising edge of an ISENSE. The high transition operates as a real time interrupt to the digital timer/controller 40 which responds by starting and applying the SMIWIN and ELSWIN signals to the read only status register 122. Bit 0 is then set "low" when the SMIWIN and ELSWIN signals are received.

Bit 1 and bit 2 of the register 122 respectively represent the SML status and the SMH status. These bits may only be set during the time between the occurrence of an ISENSE interrupt and the end of the SMI window. The SMIWIN signal itself cannot be used to directly latch the states of the bit stages when the margin comparator SMH and SML signals occur. The latency of the digital controller/timer 40 (whose interrupt initiates the SMIWIN and ELSWIN timers on a non-refractory ISENSE) could delay the start of the SMI window up to one slow clock (7.8 mS) after the actual ISENSE as shown in FIGS. 10–12. For this reason, bit stages 1 and 2 contain a first pair of flip-flops that respond to the SNIL and SMH bit outputs of DETLOGIC 120 that can occur during the SMIWIN. The state of these flip-flops is then latched out into further, parallel, flip-flops on the falling edge of SMIWIN to achieve the desired margin sampling window. These bits are read out to digital controller/timer circuit 40 as interrupts following termination of the ELSWIN signal as described below with reference to FIGS. 10–12.

Bit stage 3 of the read only status register 122 is a simple level sensitive flip-flop which is set when ESENSE goes high and remains set until the register stages are read out at the end of the ELS window.

Bit stage 4 of the register 122 responds to the reversion or REV signal level of DETLOGIC 120 which is dependent on the most recent event. If the most recent event was an ISENSE, then this bit indicates whether or not the duration of the non-refractory ISENSE event exceeded the ELS (Exceedingly Long Sense) window. This is done by reading out the state of bit stage 4 at the SMI interrupt at the falling edge of the ELSWIN signal applied by digital controller/timer circuit 40 to read only status register 122.

On the other hand, if the most recent event was a PACE, then the REV bit is latched before the pace TRIG signal and the setting of the REV state high as shown in FIG. 4.

The latched REV bit indicates the reversion status of the sense amplifier just prior to the delivery of the PACE pulse as a means of implying that the digital controller/timer circuit 40 is in the reversion pacing mode.

Bit stages 5 and 6 of the read only status register 122 are set in response to the noise floor exceeded low (NOISEL) or high (NOISEH) signals, respectively. Bit stage 7 is set in accordance with the common mode OVRNG signal state. These bits are simply level sensitive flip-flops that are set high when the appropriate OVRNG or NOISEL and NOISEH signal goes high and remain set until they are read out at the end of the ELSWIN as described below with respect to FIGS. 10–12.

OVERVIEW of AutoSensing ALGORITHM

In accordance with the present invention, the "AutoSensing" algorithm adjusts the atrial and/or ventricular sense amplifier "sensing threshold $I_{TH}$ in relation to the peak of the normal P-wave or R-wave signal while avoiding making inappropriate adjustments under a variety of circumstances described below. In order to make the adjustment we measure the "sensing margin" of the peak IVIGIN signal above the current sensing threshold $I_{TH}$ with some precision. As described above, the ANF 114 independently operates to effectively instantaneously adapt the current sensing threshold $I_{TH}$ in the presence of continuous noise levels but does not play a part in the actual Auto Sensing adjustment operation described below because the peak amplitude of the resulting IVIGIN is not affected by ANF 114.

Figure 8:
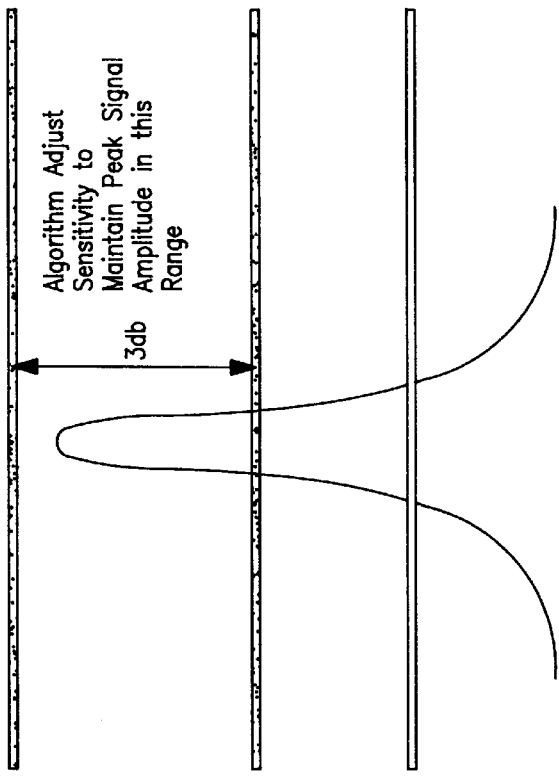
FIG. 8 is a graph of the relationship between are adjustable current sensing threshold ($I_{TH}$) and a Margin High (MH) threshold and a Margin Low (ML) threshold employed in the circuit of FIGS. 2 and 3.
Figure 9:
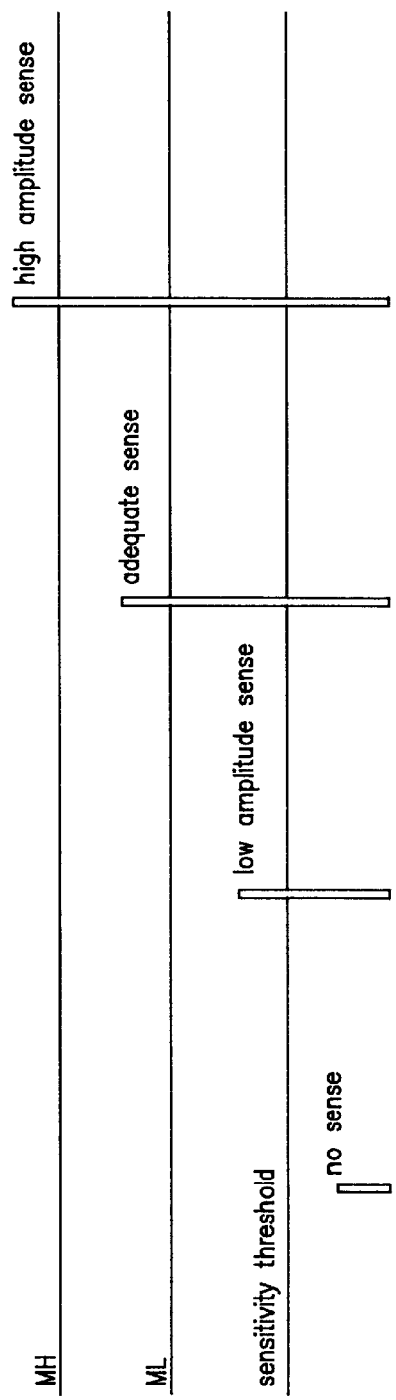
FIG. 9 is a graph of the results of the comparison of the sense event to the current sensing threshold $I_{TH}$, the MH threshold, ML threshold, and the resulting classifications thereof in the circuit of FIGS. 2 and 3.

The three different adjustable threshold levels referred to above with reference to FIG. 3 are established as shown in FIGS. 8 and 9 such that the signal peak is windowed to prevent oscillatory behavior or "dithering". These levels include the current sensing threshold $I_{TH}$ (analog current signal amplitude level that must be exceeded to indicate an ISENSE), the ML threshold level (analog current signal amplitude level greater than the sensing threshold that must be exceeded to maintain the AS margin), and the MH threshold level (analog current signal amplitude level greater than the ML threshold that must be not be exceeded to maintain the desired AS margin).

Assuming that the Autosensing sensitivity adjusting algorithm of the present invention is programmed "ON", the PDS or base sensing threshold $I_{THb}$ level prevailing earlier is thereafter adjusted to a current sensing threshold $I_{TH}$. The current sensing threshold $I_{TH}$ is subsequently continuously updated in a manner described below to maintain the sensed peak signal amplitude of the P-wave or R-wave (the IVIGIN signal in FIG. 3) between the MH and ML thresholds, that is, within the "margin window", as a means of maintaining the AS margin. For simplicity of description, it will be assumed in the following description and claims that a reference to the current sensing threshold $I_{TH}$ includes the starting PDS or pre-set base sensing threshold $I_{THb}$, unless otherwise indicated.

The MH and ML threshold values are defined as programmed multiples of the current sensing threshold $I_{TH}$ as indicated in FIG. 8 by the possible sets of multiplier pairs. The margin window therefore varies as a function of the current sensing threshold $I_{TH}$ and also varies as a function of the programmed multiplier pair. A default multiplier pair of 2.8 and 4.0 for the ML and MH unipolar thresholds, respectively, is provided(with 4.0 and 5.6 used for bipolar), and may or may not be re-programmed by the physician to (an)other programmable multiplier pair(s).

This implies that, if the algorithm centers the peak of the signal amplitude in this margin window, there will be an effective sensing margin of 3.4× which causes the sensing to be tolerant to sudden drops in signal amplitude of up to 71%. The programmable sense margin multiplier function can be used to define a "higher" or "lower" margin window with respect to the current sensing threshold $I_{TH}$. For purposes of the following description, the multiplier pairs are assumed to be fixed at the default values 2.8 and 4.0.

With the margin window so defined, minor amounts of normal EGM peak signal amplitude variation in the IVIGIN signal accompanying exercise, respiration, posture changes, drug therapies, tissue growth about the electrode, or the like, but still falling within the sensing margin range defined by the margin window will be tolerated without requiring an adjustment in current sensing threshold $I_{TH}$. Additional precautions are undertaken in accordance with the invention to avoid tracking high amplitude signals other than these desired normal P-waves or R-waves in adjusting the current sensing threshold $I_{TH}$ as described below.

Turning to FIG. 9, it depicts the classification of sense events in relation to the current sensing threshold $I_{TH}$, and the MH and ML threshold levels. During the sampling of margins, the EGM signals are simultaneously compared to the three threshold levels as described above with respect to FIG. 3, and the comparisons indicate whether the signal peaks exceed or fall below each level. The EGM signal levels or peaks that do not exceed the sensing threshold $I_{TH}$ will not be sensed as ISENSE events.

A sense event peak amplitude that does not exceed the ML level is classified as an SML (low amplitude sense) and is represented by the SML bit 1 in the read only status registers 122. A sense event peak amplitude that exceeds the MH level is classified as an SMH (high amplitude sense) and is represented by the SMH bit 2 in the read only status registers 122. A sense event peak amplitude that exceeds the ML level but does not exceed the MH level is classified as an AS (adequate sense) from the SML and SMH bits.

The object of the AutoSensing algorithm is to adjust the current sensing threshold $I_{TH}$ to keep the amplitude of the majority of sense event signal peaks between the ML and MH threshold levels while avoiding adjustment under a variety of conditions where adjustment is deemed undesirable. The implementation of the AutoSensing algorithm in the method and apparatus of the present invention takes into account a number of complicating factors that we have recognized that weigh against a simple upward adjustment of the current sensing threshold $I_{TH}$ in response to one (or more) high amplitude sense event SMH or a downward adjustment of the current sensing threshold $I_{TH}$ in response to one (or more) low amplitude sense event SML bits. These complications include the presence of EMI or noise imposed on the EGM signal, arrhythmia episodes that exhibit excessively wide R-waves or P-waves, e.g. PVCs or PACs of ectopic origin as described above, and prolonged periods of undersensing, referred to herein as "Long Term Few Senses" (LTFS) periods. Moreover, we have recognized that it is inappropriate to make any adjustment in response to refractory ISENSE events and to ISENSE events that result in triggered pacing, particularly, ventricular safety pacing, where such pacing modes are implemented in the IPG 30.

In the first instance, in the presence of continuous noise, the sense amplifier circuit 100 operates in the reversion mode described above and sets the particular NOISE and REV bits in read only status registers 122. If the noise level or other input signal level is excessively great, the OVRNG bit is set. The AutoSensing algorithm of the present invention takes into account the effects of noise setting the appropriate bits by sampling these bits at the end of the ELS window and using them as described below to declare and respond to an invalid sense.

In the second case, certain individuals are subject to episodes of large amplitude (i.e., much greater than normal amplitude), and widened ectopic beats, e.g. PVC's or PAC's that may occur sporadically or continuously for a long period of time. If the current sensing threshold $I_{TH}$ were to track and adapt to these events, and if normal amplitude intrinsic ISENSE events were then to abruptly return, there is a possibility that the latter would not be sensed due to the resulting high current sensing threshold level. In the preferred embodiment, PVCs are determined within the microcomputer 34 from the succession of VISENSE events without an intervening A-PACE or AISENSE event. The AutoSensing algorithm of the present invention takes into account such PVC events and episodes that can be determined to exist at the end of the ELS window.

The AutoSensing algorithm is also designed to operate safely over LTFS (Long Time with few senses) periods where there is no sensing or sporadic sensing (i.e., the device is pacing most of the time) in the absence of a reversion condition. For example, in rate responsive single chamber or dual chamber pacemaker pulse generators, the pacing lower rate may be established by an algorithm that takes into account the level of patient exercise or other physiological need for cardiac output as indicated by the output of a physiologic sensor. The sensor established lower rate may be higher than the intrinsic rate that might otherwise prevail. Consequently, and P-waves or R-waves may not occur within the escape interval established by the sensor derived lower rate for a long period of time.

Alternatively, the sense amplifier sensitivity may be adjusted so low that undersensing is occurring or so high that the sense amplifier is in constant reversion from sensing the noise floor. And, of course, the sense amplifier may be in reversion and still incapable of sensing intrinsic events due to excessive noise amplitude completely masking the intrinsic events. Finally, there are situations where there is just simply no intrinsic EGM activity to detect for a period of time.

In the rate responsive pacing instance, because P-wave and R-wave signal amplitudes have been reported to decline during periods of exercise, it is appropriate to not change (at least not to reduce) sensitivity during such LTFS periods of rate response driven pacing. In the instance, when the sensitivity has been adjusted into the noise floor it would be an appropriate response to try to reduce the sensitivity. Similarly, when the sensitivity has been adjusted too low and undersensing may occur, it would be an appropriate response to increase the sensitivity to regain sensing. Finally, in excessive noise situations the best response may well be to freeze the current sensing threshold $I_{TH}$ and wait out the noise.

Another consideration taken into account in the Autosensing algorithm of the present invention involves the rate at which the current sensing threshold $I_{TH}$ changes. The rate of change is fast enough to allow tracking of intrinsic signal amplitude changes, e.g., amplitude changes with exercise, drugs, transient atrial fibrillation/flutter episodes, but is slow enough to avoid tracking short term non-cardiac noise signals (e.g., myopotentials, cautery, defibrillation, etc.).

Moreover, the response time to make an amplitude change is faster to increase the sensitivity (i.e., to lower the sensing threshold $I_{TH}$), but slower to decrease the sensitivity (i.e., to increase the sensing threshold $I_{TH}$) in order to avoid instances of undersensing. Consider for example the Valsalva maneuver performed by the patient under a physician's supervision as a particular situation where undersensing could result. Initially, the EGM signal amplitude increases with the start of the maneuver. However, at the termination of the maneuver, the signal amplitude abruptly drops and temporarily undershoots the pre-maneuver amplitude for a few beats. If the algorithm were to respond too quickly to the initial short term augmentation of the amplitude brought about by the maneuver, the result could be that the device undersenses the low amplitude post-maneuver beats.

Timing Considerations

In view of these considerations, several provisions are made in the present invention to minimize the adverse influences on adjusting the current sensing threshold $I_{TH}$. First, certain sense events are deemed ineligible and excluded from consideration in the "sampling of the margins" (i.e., the comparison of the IVIGIN current signal amplitude to the MH and ML threshold values). In effect, the outcome of the sampling of margins is disregarded for refractory AISENSE or VISENSE events, that is events exceeding the current sensing threshold $I_{TH}$ and occurring during a refractory interval from a preceding ISENSE or PACE event. Note in this regard, that the appropriate refractory intervals are timed out by digital controller/timer circuit 40 on triggering of each V-PACE and A-PACE and on the AISENSE and VISENSE signals, but they do not affect the operations of the sense amplifier circuit 100 of FIGS. 2 and 3. The timing comparison to determine if an AISENSE or a VISENSE event is a refractory or a non-refractory sense event is effected in microcomputer 34.

Similarly, when a VISENSE immediately follows an A-PACE event and leads to delivery of a ventricular safety pacing pulse (a VS-PACE) 110 mS later, the resulting SMH or SML bits are excluded from consideration in adjusting the current sensing threshold $I_{TH}$. In IPG's having the ventricular safety pace feature, such a VISENSE, although technically non-refractory, is presumed to be an erroneous sense event due to lead polarization. It is excluded from consideration in the Autosensing algorithm, because it is undesirable to adapt the current sensing threshold $I_{TH}$ to the lead polarization which could have caused the VISENSE to have been erroneously detected. The exclusion of these ineligible sensing margins is also effected in microcomputer 34.

The SMI (and ELS if used) timing windows are established following an eligible VISENSE or AISENSE event to minimize the effects of noise and PVCs or PACs. Limiting the margin sampling time reduces the probability that a noise signal will erroneously trip the MHComp and MLComp comparators. The duration of the sense event is measured to insure that the signal does not exceed the sensing threshold $I_{TH}$ for the full ELS window. If the duration does exceed the ELS window, then the SML and SMH bits are not used by the AutoSensing algorithm.

Figure 10:
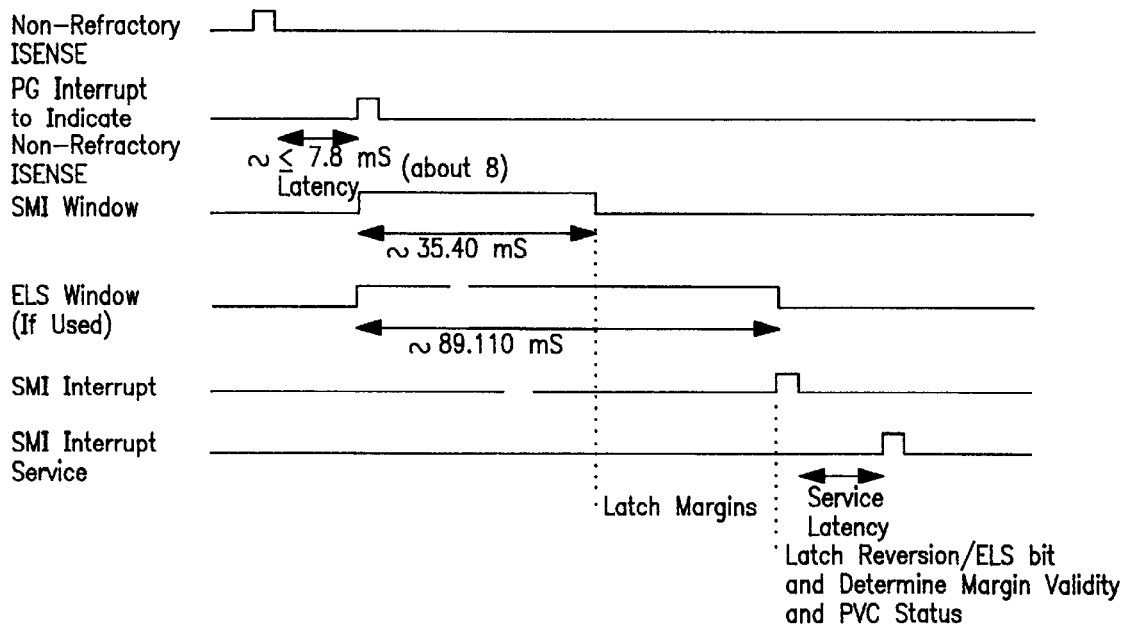
FIGS. 10–12 are timing diagrams illustrating timing windows established following an eligible sense event to minimize the effects of noise and PVCs or PACs on the adjustment of the current sensing threshold $I_{TH}$.
Figure 11:
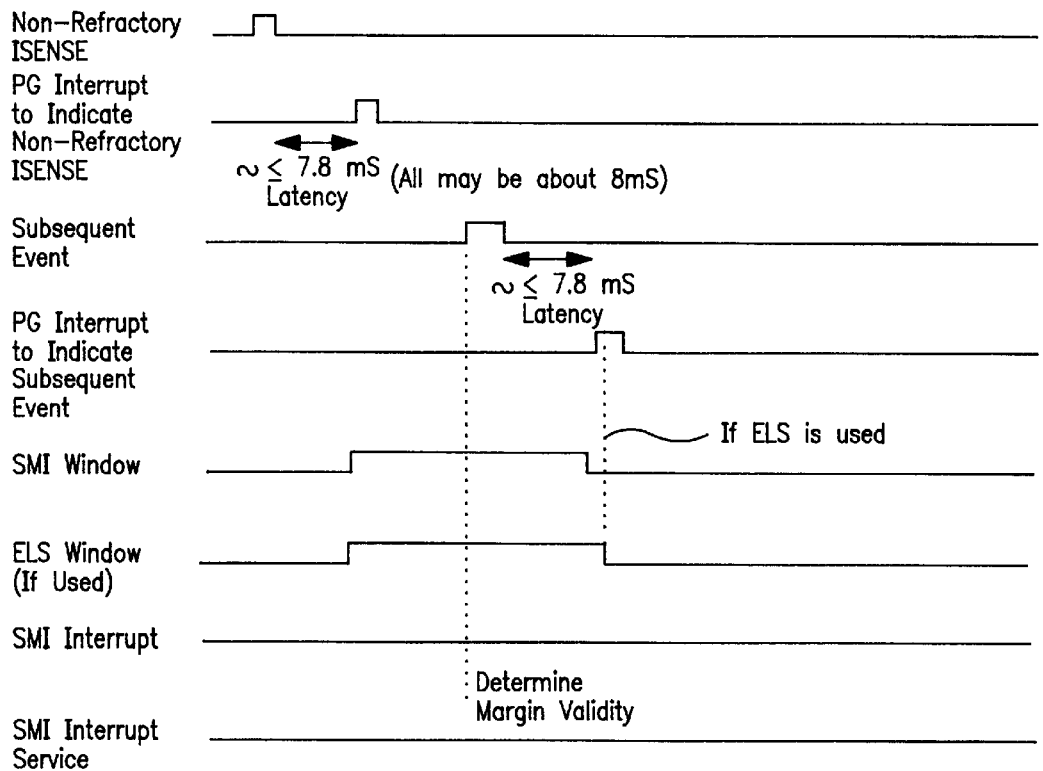
Figure 12:
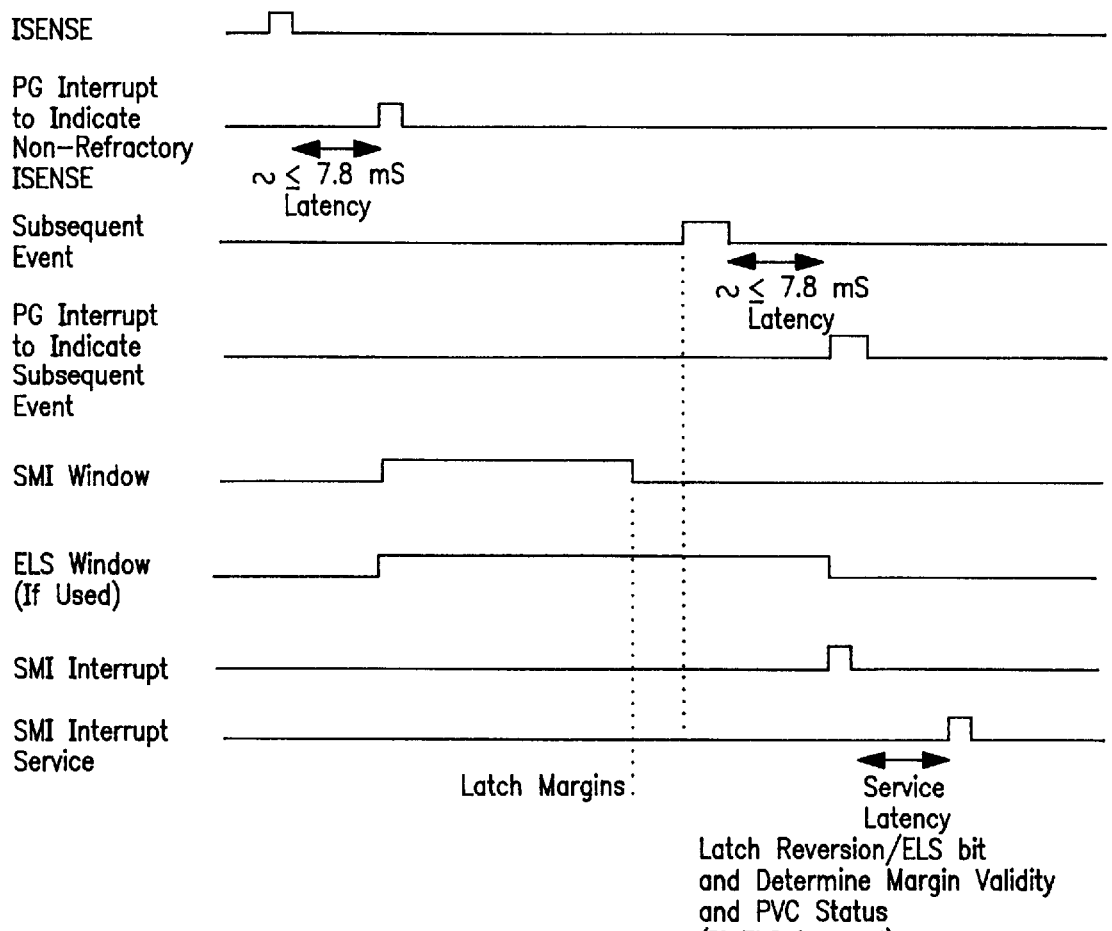

As shown in FIGS. 10–12, the SMI time window duration is programmable between 35.1–62.4 mS in four steps, namely 35.1–38 mS, 42.9–46.8 mS, 50.7–54.6 mS, and 58.5–62.4 mS, and the ELS time window duration is programmable between 89.7–144.3 mS in four steps, namely 89.7–97.5 mS, 105.3–113.1 mS, 120.9–128.7 mS, and 136.5–144.3 mS. The SMI and ELS window duration's vary by about 3.9 mS and 7.8 ms depending on which of the two phases of the 7.8 ms clock period that the window timers start on from an ISENSE interrupt following the setting of the ISENSE bit 0 in the read only status register 122A, 122V. The SMI and ELS time windows are programmable from among these sets of window duration's to permit some degree of flexibility.

In the preferred embodiment, only a single set of SMI and ELS window timers are provided in digital controller/timer 40 and function as either an atrial or ventricular ELS and SMI window timer depending on the last ISENSE event. Consequently, the SMI and ELS window timers are reset by a subsequent PACE or ISENSE event associated with either the atrial or ventricular channel. It should also be noted that an atrial and/or ventricular refractory period is also started from the receipt of the AISENSE or VISENSE, respectively, in separate refractory timers in digital timer/controller 40. The minimum programmable refractory period preferably exceeds the maximum programmable ELS time window.

The SMI window duration is based on the time required to propagate the peak of the cardiac signal through the sense amplifier circuit. The ISENSE event may be triggered during the rise time of the IVIGIN signal, and is immediately set in ISENSE bit 0. The SMI window duration needs to be long enough to catch the sense event peak in order to make the SMI and SML margin comparisons, but short enough to accommodate short sensed or paced AV delays and to exclude other noise signals. A 42.9–46.8 msec SMI window duration is a preferable default.

The choice of the ELS window duration is based on the amount of time required to propagate a signal through the sense amplifier and to allow enough time for the filter network associated with the TRANSAMP stage 110 to settle out. During this time, the reversion condition may be set and reset many times due to the ringing of the IVIGIN signal amplitude. The 105.3 mS duration is preferred because it is equal to about three time constants of the bandpass filter (associated with TRANSAMP stage 110) time constant, which should be a reasonable amount of time for the filter to ring out and settle. The 105.3 mS ELS window duration is also preferred to protect against the CENELEC burst noise test (100 mS long burst of 2 mV amplitude 16 Hz sine wave). Ideally, the Autosensing algorithm should recognize this noise source and not adapt the current sensing threshold $I_{TH}$ to it.

The SMI and ELS windows are timed out by SMI and ELS window timers in digital controller/timer circuit 40 and are triggered simultaneously on a non-refractory ISENSE event interrupt. When a non-refractory ISENSE event is processed in the sense amplifier circuit 100, there is about at least one clock cycle delay until the ISENSE bit 0 of the read only status register 122 is set and the ISENSE interrupt to the digital controller/timer circuit 40 occurs and the timers start simultaneously timing out the SMI and ELS windows, as shown in FIGS. 10–12.

As shown in FIG. 3, the SMIWIN and ELSWIN signals are applied to the read only status register 122. During the SMI window, the IVIGIN signal is compared to the ML and MH threshold levels in DAC 118 as described above. At any time during the SMI window, the SML and SMH margin comparison may go positive or high, and the result set in the bit 1 and 2 stages of the read only status register 122. When the SMI window timer times out under normal circumstances depicted in the timing diagram of FIG. 10, the termination of the SMIWIN signal latches the states of the bit 1 and bit 2 stages so that they cannot be changed by any subsequent fluctuations of the IVIGIN signal amplitude during the ELS window. In this manner, sampling of the margins begins on the ISENSE interrupt, and the SML and SMH margins are latched on the falling edge of the SMI window.

When the ELS window times out (if we are using it), the state at that moment of the REV bit in stage 4 of read only status register 122 is read out in response to the SMI interrupt. If at that moment the sense amplifier circuit 100 continues to be reverted, the ISENSE event is attributed to a noise signal (i.e., identified as unreliable), and the sampled margins are not included in the sensitivity adjusting algorithm.

The time out of the ELS window generates a SMI interrupt which is delayed by a service latency period of up to one clock cycle. The SMI interrupt service reads out the bit stages 1–7 of the read only status register 122 for processing by the microcomputer 34 and/or the digital controller/timer circuit 40. The read out stages may include the OVRNG, NOISEL, NOISEH, REV, ESENSE, SMH and SML bit states. If in an embodiment that does not use ELS, then REV, Noise H and E sense signals may not be needed.

Following the initial ISENSE event, a number of subsequent events may occur that are taken into account including an ISENSE event interrupt that is processed in the same sense amplifier or is processed in the other sense amplifier or a pace TRIG event interrupt in either chamber. In the former case, the ISENSE is latched in bit stage 0 for the appropriate atrial or ventricular read only status registers 122A or 122V, and transmitted as an ISENSE interrupt to the digital controller/timer circuit 40 after the slow clock latency delay. For all pacing modes in which the sensing assurance function is programmed to operate, the available programmable refractory periods all exceed the ELS window and therefore preclude an ISENSE event from the sense amplifier in the same channel from being characterized as a non-refractory ISENSE. However, in the dual chamber pacing modes, it is conceivable that a non-refractory ISENSE interrupt may be generated the other sense amplifier read only register stage while the SMI or the ELS window is/are timing out. These subsequent events are taken into account as follows.

In the timing diagram of FIG. 11, the subsequent event interrupt falls within the SMI window commenced by the initial non-refractory sense event. The subsequent event occurring within the SMI window causes the SMI and ELS window timers in the digital controller/timer circuit 40 to stop after a slow clock latency period. The SMH and/or SML state is not latched in the respective stage(s) of read only status register 122 at the end of the SMI window.

The reason for this is that if the subsequent, refractory event occurs in the same chamber during the SMI window, that its occurrence could corrupt the measurement of the margins made on the initial ISENSE event. For this reason, these margin measurements are not included in the sensitivity adjusting algorithm (i.e., the initial non-refractory ISENSE event is identified as unreliable).

It should be noted that while a subsequent ISENSE event detected in one of the sense amplifiers may reset the SMI window being timed out in relation to an earlier ISENSE event in the same chamber, it starts the SMI and ELS windows in the other chamber.

The remaining scenario is illustrated in the timing diagram of FIG. 12 which shows a subsequent event occurring after the SMI window times out, but within the ELS time window. As described above, the occurrence of an initial non-refractory ISENSE starts the window timers and latching of the SMH and/or SML bits at the end of the SMIWIN signal. The subsequent event occurring within the ELS time window causes the ELS time window to be terminated, and the SMI interrupt to be generated.

The treatment of this situation is then exactly the same as in the first scenario of FIG. 10. That is, if none of the REV bit 4, the NOISEH bit 5, NOISEL bit 6 or the OVRNG bit 7 are set high, the SMH and/or SML bits may be used to update the sensitivity following the Autosensing algorithm. (Of course in an embodiment that does not use REV or Noise H signals, these bit 4 and 5 signals can be ignored.) Otherwise, the sampled margin measurements are identified as unreliable and not used.

The following is a special case for VISENSE after AISENSE.

It should be apparent from the previous discussion with reference to FIG. 10 that the possibility exists in a dual chamber IPG that a VISENSE event can occur during the atrial SMI time window following an AISENSE event. When the intrinsic A-V delay is so short that the VISENSE event occurs during the atrial SMI window, there is no means to obtain a reliable atrial margin measurement. Consequently, if this occurs chronically, automatic sensitivity adjustment of the atrial sense amplifier sensitivity is lost.

If the VISENSE event following the AISENSE event by the intrinsic A-V delay falls within the atrial ELS window as illustrated in FIG. 12, it is presumed that the VISENSE event terminated the atrial ELS time window, and the REV bit is ignored. (It should be noted again that in one embodiment preferred, we do not use the REV bit or the ELS time window for REVERSION checking.) The advantage of this response is that it preserves automatic sensitivity adjustment despite intrinsic A-V delays as short as the SMI window. The disadvantage, of course, is that the noise immunity afforded by the ELS time window is lost.

AutoSensing Algorithm

Turning now to a specific implementation of the AutoSensing algorithm of the present invention, it is preferably stored in memory in the micro-controller 34 of FIG. 1. The algorithm initializes the sense amplifiers 38A and 38V of the dual chamber IPG with a nominal or base atrial sensing threshold $I_{THab}$ of preferably 0.5 mV for the atrial sense amplifier 38A in both unipolar and bipolar lead configurations (except 0.25 mV for the VDD mode) and a nominal or base ventricular sensing threshold $I_{THvb}$ of preferably 2.8 mV for the ventricular sense amplifier 38V in both unipolar and bipolar lead configurations. The extreme lower and upper sensitivity limits of the ventricular sense amplifier are preferably 2.0 mV and 5.6 mV, respectively, in both the unipolar and bipolar lead configurations. The extreme lower and upper sensitivity limits of the atrial sense amplifier are preferably 0.5 mV and 1.4 mV, respectively, in the atrial unipolar lead configuration and preferably 0.5 mV and 0.7 mV, respectively, in the bipolar lead configuration, except for the VDD bipolar lead configuration, where the limits are preferably 0.18 mV and 0.35 mV. The atrial and ventricular base sensing thresholds $I_{THab}$ and $I_{THvb}$ may be programmed to the PDS within these ranges. In the following description, a current sensing threshold $I_{TH}$ will be referred to as exemplary of the adjustment of the current atrial or ventricular sensing thresholds including the base sensing thresholds $I_{THab}$ and $I_{THvb}$.

The AutoSensing algorithm establishes four counters or accumulators per sense amplifier 38A and 38V within microcomputer 34, or may use hardware registers set up especially for the purpose of maintaining counts of events used in adjusting the current sensing threshold $I_{TH}$ for the sense amplifier. These are called the SMIACC, PEA, RPA, and LTA.

The general organization of their relationship is as follows.

There are two independent mechanisms which can cause adjustment of sensitivity, gain or $I_{TH}$. The first mechanism is the primary mechanism and adjusts sensitivity to achieve the desired sensing margin with respect to sensed events. The second mechanism is a mechanism related to special case handling that tries to adjust sensitivity back to a reasonable (historically) value, the LTA value, if sensing appears to be lost either due to undersensing or noise reversion.

The first mechanism is accomplished by the SMIACC overflow or under flow operating to adjust the $I_{TH}$. This occurs as described in detail elsewhere when the weightings added to SMIACC by hi or lo valid sensed events indicate a need to move toward less or more sensitive gain (i.e., toward a higher or lower threshold, respectively. Since the weightings given to other events (paces, PVCs, invalid events) drive the SMIACC value toward the initial value (thus away from under/over flow) adjustment to the sensitivity of the sense amp (due to SMIACC over/under flow) can only occur on a sensed event.

The second mechanism is through the overflow of the PEA (Paced Event Accumulator). Since a value of a preferably a smaller number (like 4) is added to PEA for each pace and a larger number (like 16) is subtracted for each sense, PEA can only overflow during periods of little sensing and much pacing. The PEA indicator signal can only act to adjust the sensitivity value $I_{TH}$, after the value indicated by the RPA shows that a majority of recent paced events have been in the sense amplifier's "noise reversion" condition. In other words, when the PEA overflows, the present value of the RPA is consulted to determine whether a majority of recent paced events have occurred during a sense amplifier 'noise reversion' condition. Based on this data, the $I_{TH}$ will be adjusted higher or lower but only if it is toward the long term average sensitivity (LTA). No adjustment will occur if a) $I_{TH}$=LTA, b)sensitivity is less than the LTA indicated sensitivity and RPA indicates a noise reversion condition, or c) sensitivity is more-sensitive than the sensitivity indicated by the LTA and the RPA indicates no reversion condition exists.

In particular, the count of the "SMI Accumulator" (SMIACC) is used to adjust the current sensing threshold $I_{TH}$. The count is adjusted in response to valid, non-refractory ISENSE events and the SMH and SML bits latched in read only status registers 122. The "LTA Sense Counter" (Counting every 16 valid senses to update the LTA register value one time) maintains a count of eligible ISENSE events and is used to determine when to update the LTA as described below. The "Paced Event Accumulator" (PEA) maintains a history of PACE events vs. ISENSE events, and its count is used to establish the LTFS state and setting of the current sensing threshold $I_{TH}$ to the LTA. In certain ventricular pacing only modes, such as the VDD mode, the PEA is disabled for the atrial chamber. The "Reversion Pace Accumulator" (RPA) provides a history of reversion PACE events vs. non-reversion PACE events and is also used in the LTFS determination algorithm.

Figure 13:
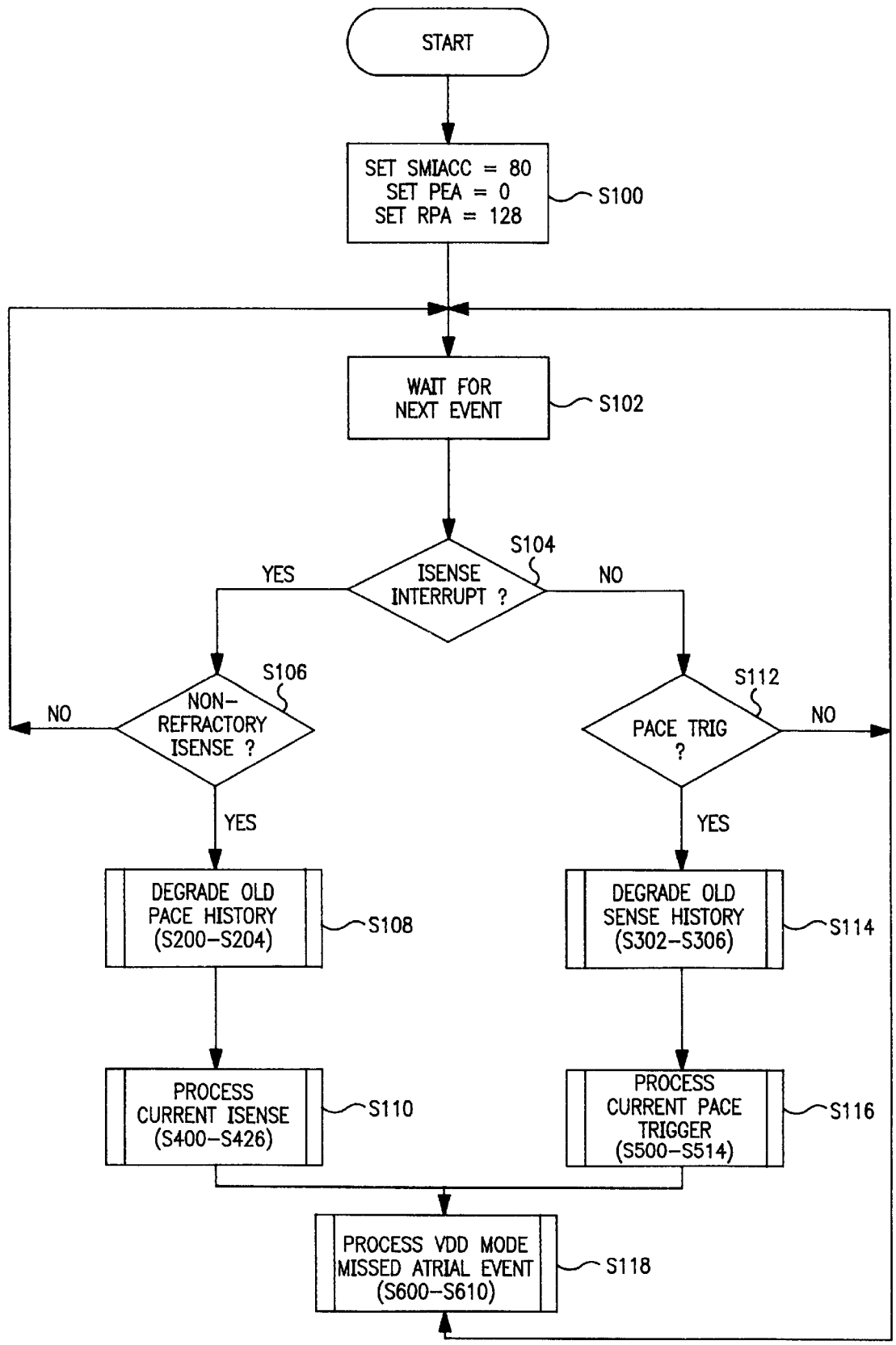
FIG. 13 is a top level flow chart of the AutoSensing algorithm.

FIG. 13 depicts the top level operating algorithm of the AutoSensing function from a start or restart condition. FIGS. 14–25 depict subsidiary algorithms implementing the AutoSensing function and explanatory diagrams and charts for the subsidiary functions and operations.

The AutoSensing algorithm is initialized at POR (Power On Reset; a condition due to an extraordinary device event such as a power failure) and may also be programmed operable or inoperable by a programmed-in command or rendered inoperable in certain pacemaker operating modes. For example, the AutoSensing algorithm is inoperable prior to implant detection or when the IPG is in a temporary mode operation, a magnet-mode operation, or during a pacing threshold search or if the IPG is programmed to a sensing-only mode, a pacing triggered mode, or a non-sensing mode for the chamber in question. These conditions are monitored under a general operating algorithm of the IPG stored in the microcomputer 34. It should also be noted that the LTA is restarted to recompute the LTA sensing threshold value at POR, on programming of the emergency VVI special command, when the sensing polarity is changed by a lead integrity operation, or upon programming of the atrial or ventricular AutoSensing restart special command. Again, the LTA restart function is initiated by an algorithm stored in microcomputer 34 and is not pertinent to the present invention. Further details relating to the starting of the LTA function and the use of the LTA sensing threshold are described below.

Figure 21:
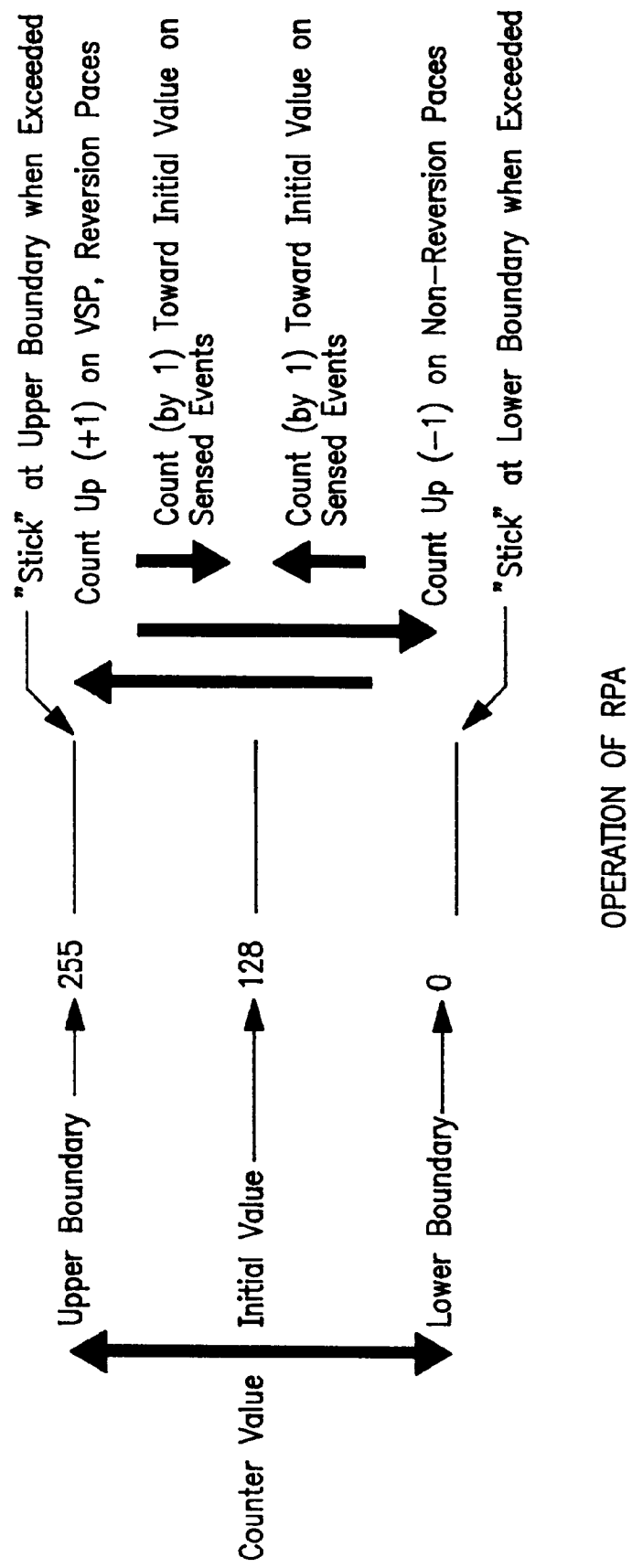
FIG. 21 is a graph illustrating the RPA count adjustment.
Figures 22, 23:
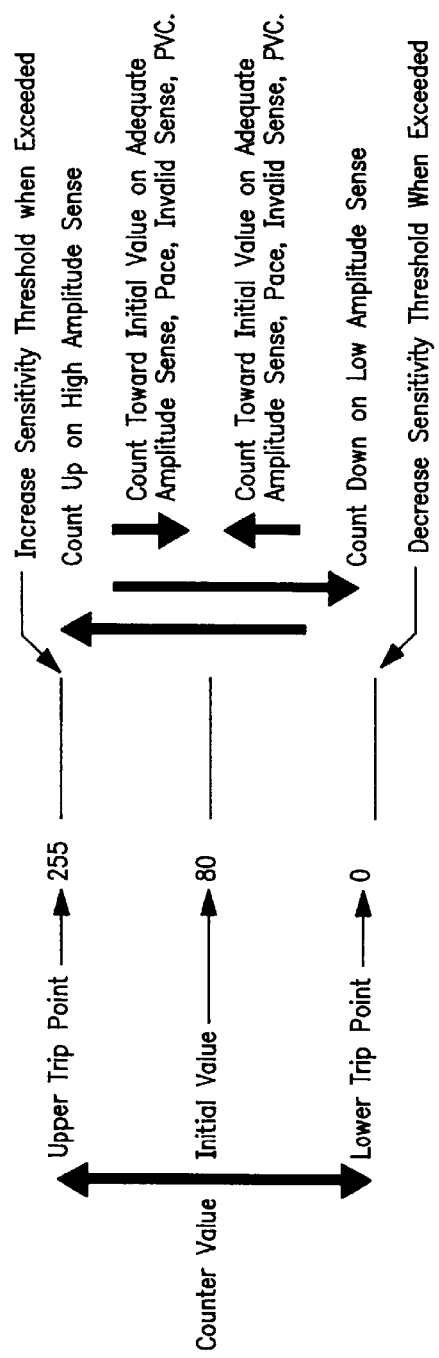
FIG. 22 is a graph illustrating the SMIACC count adjustment.
FIG. 23 is a graph of SMIACC adjustment weights.
Figure 24:
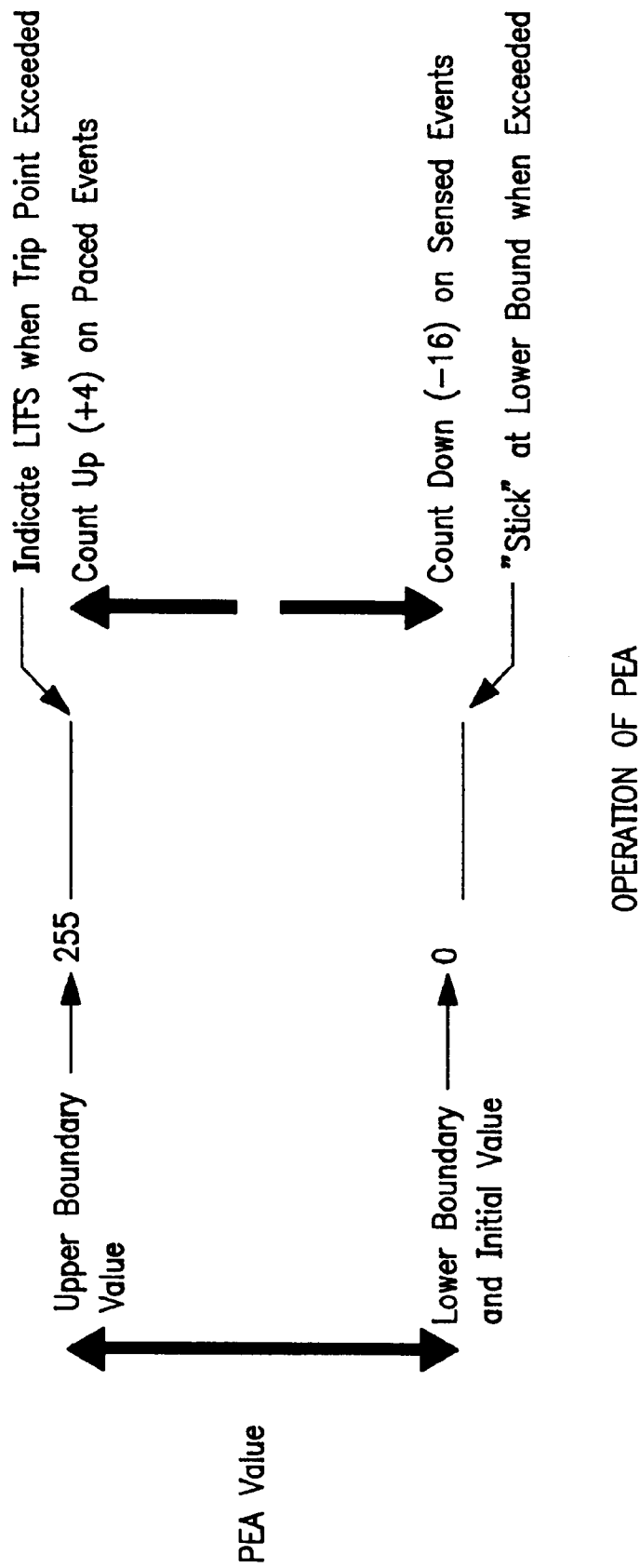
FIG. 24 is a graph of PEA count adjustment.
Figure 25A:
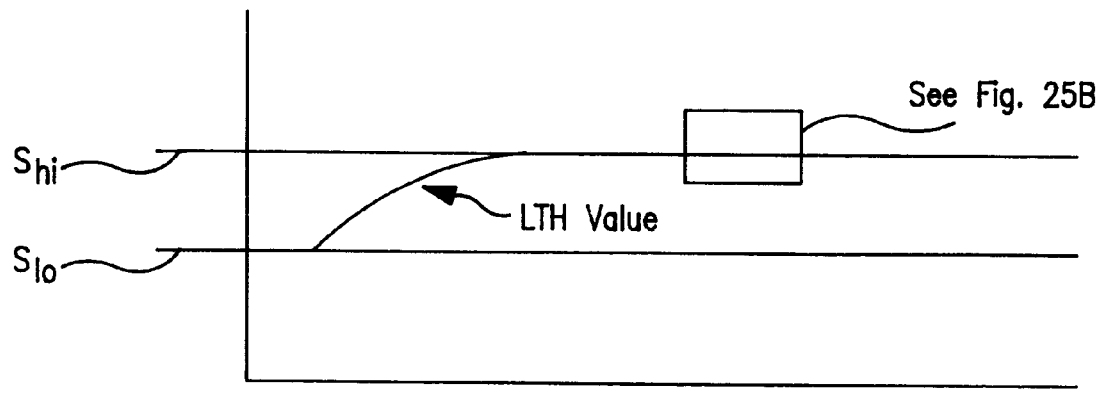
FIGS. 25a and 25b are graphs of the LTA value related to sensitivity settings, 25b being a blow up of a small section of 25a as indicated.
Figure 25B:
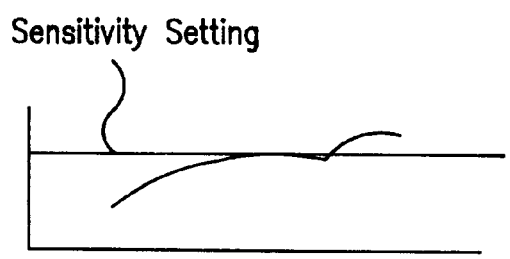

In FIG. 13, at step S100, an algorithm count restart of the sense amplifier in question is accomplished by discarding the SMIACC count, the LTFS pace/sense history, and the LTFS reversion pace history. These histories are discarded by the setting the SMIACC to 80, the PEA to zero, and the RPA to 128. These initial counter values or counts are also depicted in FIGS. 21, 22 and 24.

At step S102, the algorithm awaits the next event. As described extensively above, the next event may be an ISENSE event (which is immediately transmitted to the digital controller/timer 40 upon its detection by the atrial or ventricular sense amplifier 38A or 38V) or it may be a pace TRIG generated by the digital controller/timer 40. The ISENSE event and pace TRIG event are distinguished in decision blocks S104 and S112.

If an ISENSE event is detected, the algorithm checks in step S106 to ensure that it has not occurred in the refractory period of a preceding ISENSE event for the same channel, i.e, is not a refractory ISENSE event. If it is determined to be a refractory ISENSE event, then the algorithm loops back to wait for the next event at step S102. If a non-refractory ISENSE event is detected, the algorithm moves to degrade the "old pace history" in step S108 and to process the current ISENSE event in step S110.

Figure 14:
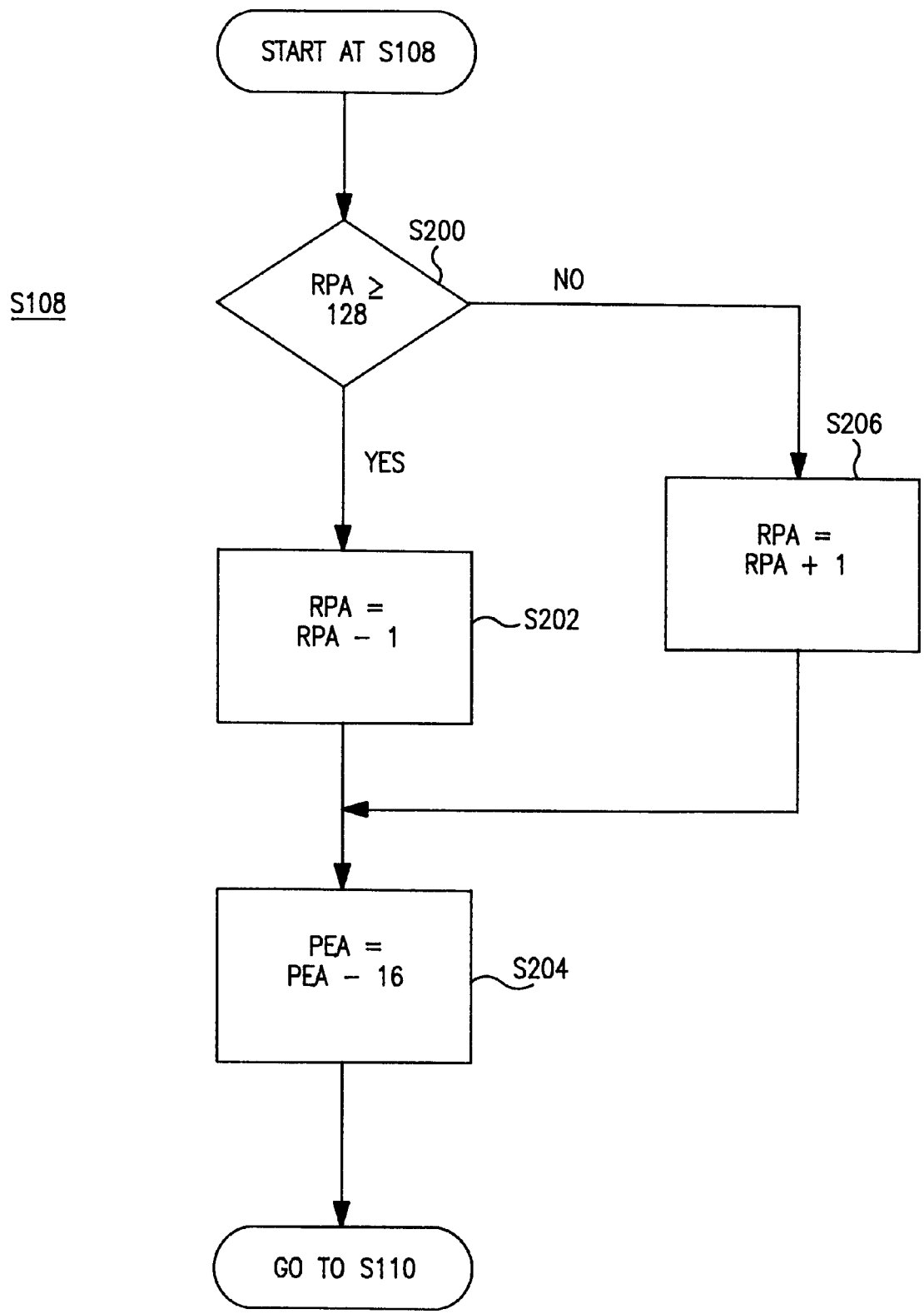
FIG. 14 is a detailed flow chart of step S108 of FIG. 13.

Step S108 effects an adjustment of the counts of the RPA and the PEA as shown in greater detail in the steps S200–S204 of FIG. 14. At step S200 of FIG. 14, the current count of the RPA is examined. If the current RPA count is > or =128, then it is adjusted by −1 in step S202. But, if the count is <128, then the RPA is adjusted by +1 in step S206. In either case, the PEA count is then adjusted by −16 in step S204 in response to the non-refractory ISENSE event.

The RPA count records information about the frequency of reversion pace events vis-a-vis non-refractory ISENSE events. Non-refractory ISENSE events tend to restore or maintain the RPA count at its initial value of 128 as also depicted in FIG. 21. The RPA count is also adjusted by +1 following a pace due to noise reversion (i.e., when the REV bit in read only status registers 122 is present) and is adjusted by −1 following a non-reversion pace TRIG event regardless of whether or not the current RPA count is >128 or <128 as shown in FIGS. 21. These latter aspects of the RPA function are described in greater detail below.

As shown in FIG. 24, the PEA count is adjusted by +4 following every paced event in the same chamber (regardless of the reversion or non-reversion status of the pace TRIG) and is adjusted by −16 following every non-refractory ISENSE event in the same chamber (regardless of whether or not the ISENSE event is determined to be valid/invalid or PVC/non-PVC). The lower boundary and initial value of 0 is thereby maintained as long as non-refractory ISENSE events continue. If for any reason asynchronous or reversion mode pacing prevails sufficiently long enough, the upper boundary value of 255 will be exceeded, indicating a LTFS condition and resulting in the LTFS operation described below in reference to FIGS. 19 and 20.

Figure 15:
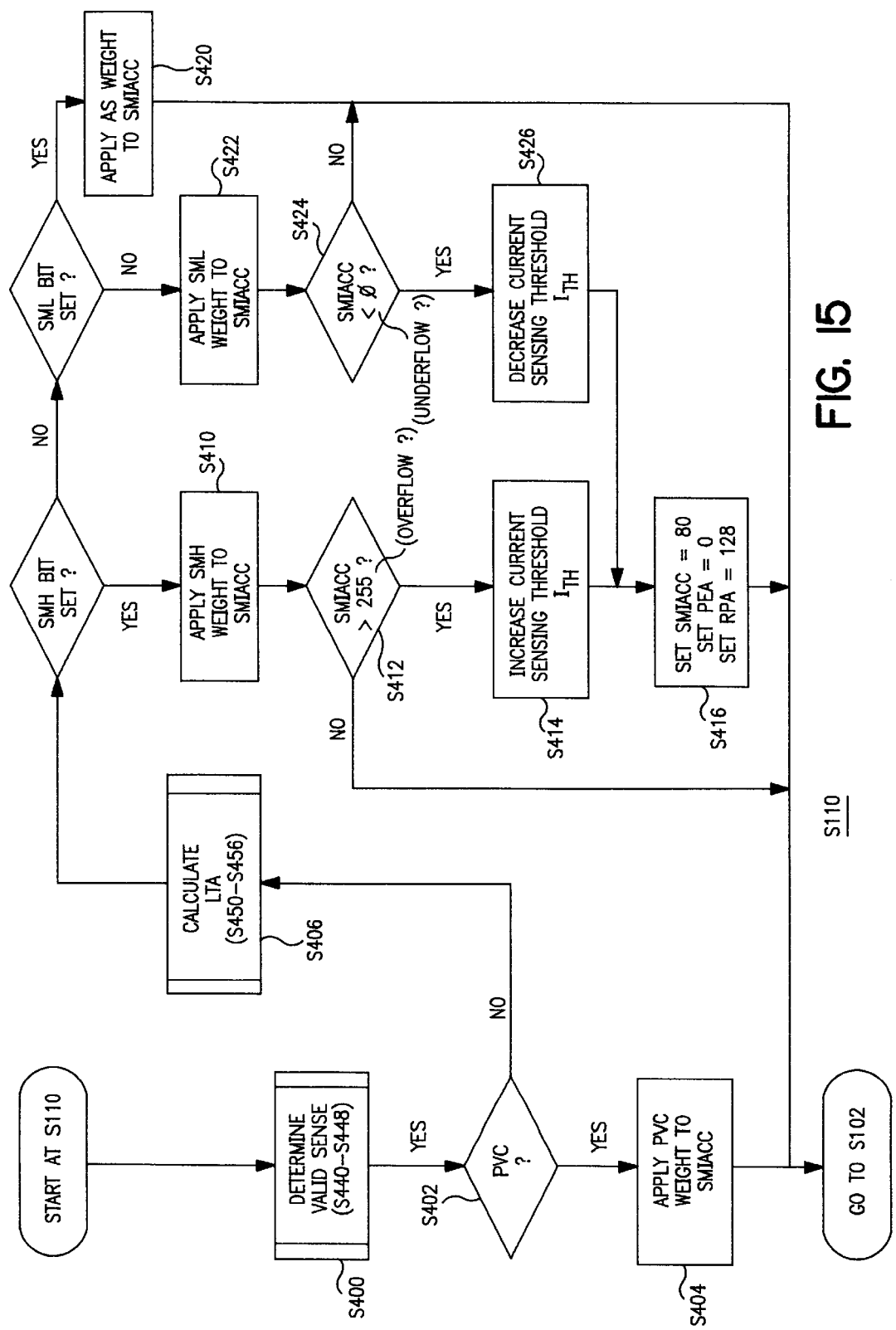
FIG. 15 is a detailed flow chart of step S110 of FIG. 13.
Figure 16:
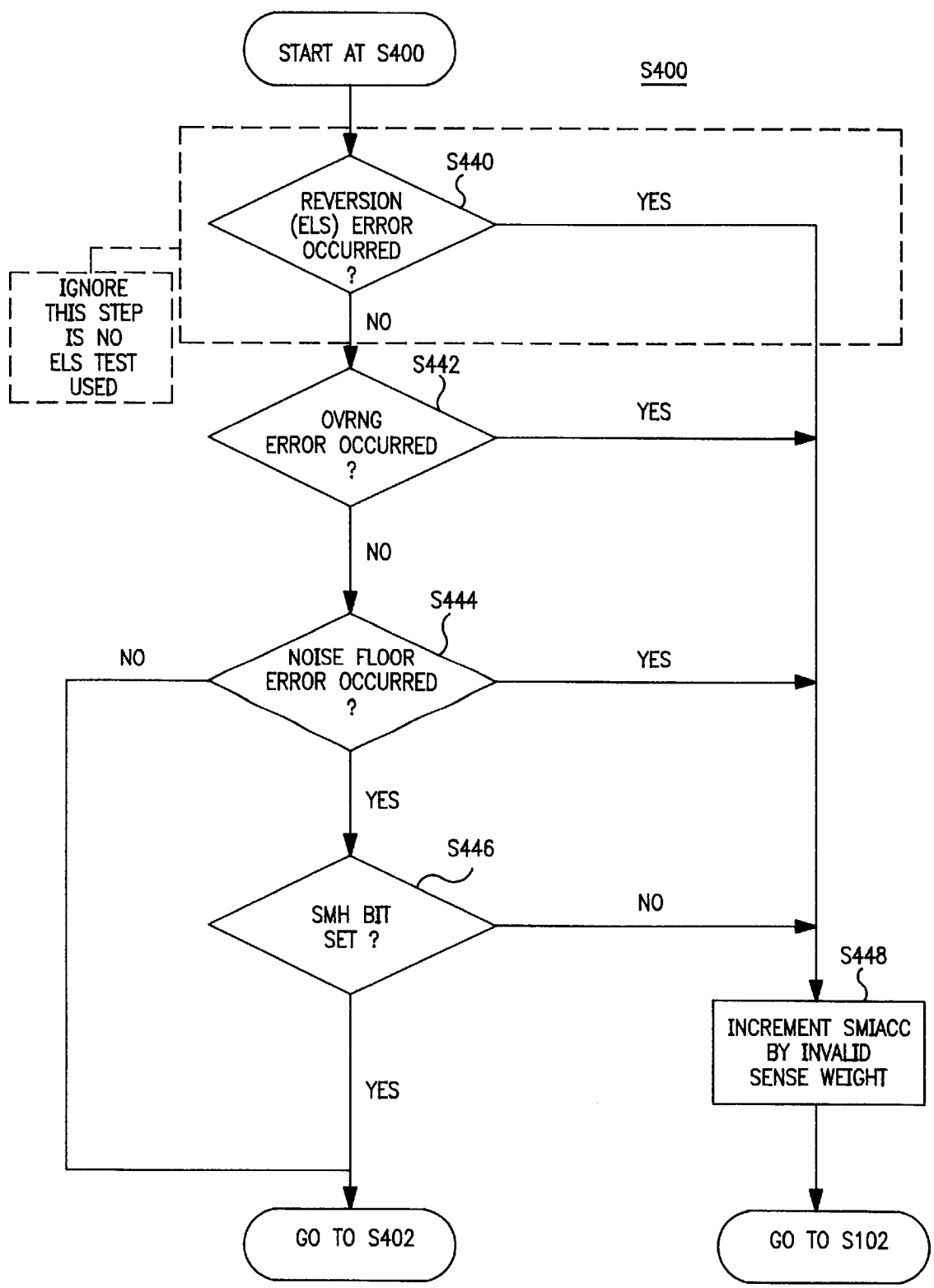
FIG. 16 is a detailed flow chart of step S400 of FIG. 15.

After adjustment of the RPA and PEA counters, the current non-refractory ISENSE is processed in step S110 as shown in FIG. 15. At the first step S400, certain non-refractory ISENSE events are characterized as valid or invalid. An invalid ISENSE event is an ISENSE event that occurs while an error bit, including the REV bit, the NOISEL bit or the OVRNG bit are present in read only status register 122. If REV bit, read responsive to an SMI interrupt when the ELS window times out shows the sense amp (106) in reversion status, then the sense event ISENSE at that time is deemed noise and step S448 is performed. Otherwise the program moves on to step 442. At steps S442 and S444, the states of the OVRNG bit 7 and the NOISEL bit 6 are checked to determine if they indicate the error condition. If the results of steps S440–S444 indicate the error condition, then the SMIACC (Sense Margin Indicator Accumulator) is incremented by the invalid sense weight in step S448 and the algorithm loops back to step S102 of FIG. 13 to await the next ISENSE event.

If no error conditions are indicated in steps S440–S444, then the algorithm advances to step S402 of FIG. 15.

Assuming that an invalid ISENSE event is determined in step S400, the invalid ISENSE weight that is applied to the SMIACC count is −8 when the present SMIACC count is > or =80 and is +8 when the present SMIACC count is <80, as shown in FIGS. 22 and 23. Therefore, the adjusting of the SMIACC count in response to an invalid ISENSE event tends to return the count to the initial value of 80.

Returning to FIG. 15, and assuming for the moment that the ISENSE event is determined to be valid in step S400, the algorithm determines whether or not the valid, non-refractory ISENSE event constitutes a premature ventricular contraction (PVC) in step S402. The overall operating algorithm of the microcomputer 34 maintains a status register of atrial and ventricular ISENSE events and pace TRIG events from which the sequence of the most recent events may be continuously determined. A PVC is determined in step S402 from the sequence of the current ventricular ISENSE event with respect to the immediately preceding ISENSE or TRIG event. If the current ventricular VISENSE event is not immediately preceded by either an atrial AISENSE event or an A-TRIG event, then it is presumed that the current VISENSE event is a PVC, and the SMIACC is adjusted by the PVC weight in step S404. As shown in FIG. 21, the PVC weight is −1 if the present SMIACC count is > or =80 and +1 if the present SMIACC count is <80. In this manner, runs of successive PVCs tend to drive the SMIACC count back to the initial value of 80, so that the current sensing threshold $I_{TH}$ is not adjusted.

It should be noted that steps S402 and S404 are only employed in the AutoSensing algorithm processing the ventricular sense amplifier sensitivity and are not present in the AutoSensing algorithm for processing atrial ISENSE events from the atrial sense amplifier. In the atrial channel Autosensing algorithm, when a valid AISENSE event is determined in step S400, the algorithm proceeds to calculate the LTA in step S406 and the remaining steps of FIG. 15.

FIG. 17—S406

Figure 17:
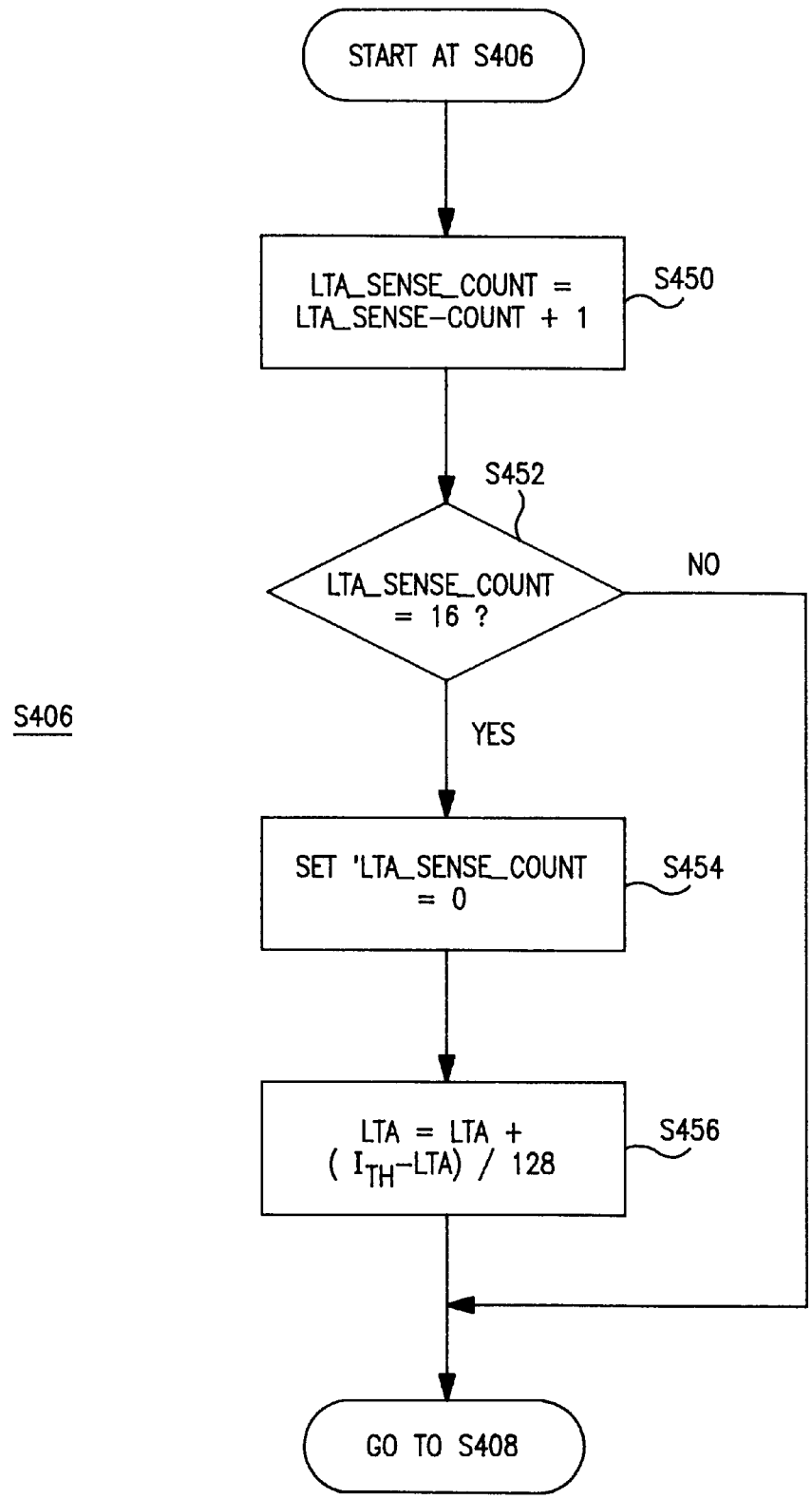
FIG. 17 is a detailed flow chart of step S406 of FIG. 15.

Returning to step S406 of FIG. 15, the calculation of the LTA is set forth in steps S450–S456 of FIG. 17. In step S450 of FIG. 17, the count of an LTA counter LTASENSE_COUNT is incremented.

In step S452, the LTA_SENSE_COUNT is compared to 16. When the count exceeds 16, the LTA_SENSE_COUNT is reset to 0 in step S454. Then, in step S456, the LTA is calculated by following the process described in FIG. 17 to increase or decrease a Long Term Average (LTA) value register (which may be managed by the microcomputer and stored in memory). In other words, for each sense amplifier in the IPG, the preferred embodiment maintains and adjusts the LTA sensing threshold value following every sixteenth eligible ISENSE event as counted in a LTASENSE_COUNT counter (which preferably counts by "16s" to 256). For example, each time an eligible ISENSE event occurs, a value of 16 can be added to LTASENSE_COUNT. The overflow of the LTASENSE_COUNT counter is the indicator to update the LTA sensing threshold value).

The LTA sensing threshold value is calculated and maintained in 12-bit precision based on the following formula (in settings times 256):

$$DELTA = I_{TH} - \text{previous LTA}$$

$$LTA = \text{previous LTA} + DELTA/128, \text{ if ABS(DELTA)}/128$$
$$\quad = \text{previous LTA} + SGN(DELTA), \text{ if ABS(DELTA)}/128$$

where:

$$SGN(DELTA) = 1 \text{ if DELTA} > 0$$
$$= 0 \text{ if DELTA} = 0$$
$$= -1 \text{ if DELTA} < 0.$$

$$ABS(DELTA) = DELTA$$

The 4-bit LTA is derived from the 12-bit LTA by rounding the lower 8 bits. The divisor of 128 in the above formula indicates that the LTA will be based on the last 128 (*16= 2048) valid ISENSE events. This long time constant is chosen such that the LTA adapts very slowly to sensitivity changes and is not likely to become "stuck" at extreme sensitivity settings, thereby, preventing the algorithm from regaining sensing. Furthermore, special checking was added to the calculation to insure that the truncation error incurred when the numerator in the right hand side of the above equation is <128 does not prevent the LTA from achieving a value equal to the current sensitivity setting. In other words, referring to FIGS. 25a and 25b, as the LTA value approaches the sensitivity setting Shi, the truncation error doesn't prevent LTA from achieving Shi.

The rationale behind this operating method of deriving the LTA is that once the AutoSensing algorithm starts to operate and if the AutoSensing returns to the PDS a Physician Determined Sensitivity level, during periods of little sensing, the sensing performance will ultimately be no worse than it would have been if the nominal sensing threshold were maintained. The only time the sensing performance could be worse is the short period of time where the sensitivity is drifting back toward the PDS. The LTA would be preferable, however, due to the fact that the algorithm would not necessarily have to re-adapt the sensitivity to regain adequate margin after a period of little sensing. This could help avoid instances of undersensing when the current signal amplitude has, over a period of time, dropped to a level that is much lower than the PDS sensing threshold.

The initial value of either the LTA or the PDS defines the nominal sensitivity. The LTA's initial value is set by the PDA if the physician uses one. Returning to FIG. 15, after adjustment of the LTA in step S406, the adjustment of the SMIACC (Sense Margin Indicator Accumulator) by the weights shown in FIGS. 22 and 23 takes place depending on the current count of the SMIACC and the classification of the signal peak of the IVIGIN signal. As stated above, the SMIACC count is initially set to 80. If it is determined in step S408 that the SMH bit 1 is not set, then the status of the SML bit 2 is checked in step S418. If the SML bit 2 is set and the SMH bit 1 is not set, then it is presumed that the IVIGIN signal peak that triggered the ISENSE event (Icomp) falls within the margin window of FIGS. 8 and 9, and the ISENSE event is characterized as an adequate sense (AS). In step S420, the SMIACC count is adjusted by the AS weight shown in FIG. 23. In this case, the AS weight is −8 if the present SMIACC count is > or =80 or +8 if the present SMIACC count is <80. In this manner, the SMIACC count is driven toward the initial value of 80 as long as the AS bit is set on each valid, non-refractory ISENSE event.

Returning to step S408, if the SMH bit 2 is set to indicate that IVIGIN exceeds the margin high threshold MH, then the SMIACC count is adjusted by the appropriate SMH weight in step S410. Referring again to FIGS. 22 and 23, the SMH weight depends upon whether or not the present count of the SMIACC is <80 or > or =80. In the former case, the SMIACC count is increased by +8, and, in the latter case, the SMIACC count is increased by +5. This disparity provides for an acceleration in the SMIACC count below the initial value of 80 so that sensitivity can decrease faster than it can increase.

Then, the SMIACC count is compared to a maximum limit or upper trip point count of 255 in step S412. If the upper trip point is exceeded, the current sensing threshold $I_{TH}$ is increased by one sensitivity scale level in step S414. The SMIACC, the PEA, and the RPA counts are then reset to the initial values in step S416. The processing of the current ISENSE event is then ended, and the AutoSensing algorithm loops back to wait for the next event in step S102 of FIG. 13. Similarly, if the SMIACC count remains below 255 in step S412, the processing of the current ISENSE event is completed, and the algorithm loops back to wait for the next event in step S102.

If it is determined that the SML bit 1 and the SMH bit 2 are not set in steps S418 and S408, then it is presumed that the IVIGIN signal peak has exceeded the current sensing threshold $I_{TH}$, thereby triggering the ISENSE event, but is a low amplitude sense as shown in FIG. 9. In that case, the SMIACC count is adjusted by the SML weight shown in FIGS. 22 and 23 in step S422. If the present SMIACC count is > or =80, then the SMIACC count is decremented by −8. If the present SMIACC count is <80, then the SMIACC count is decremented by −5. In this manner, the SMIACC count is weighted toward the initial value.

In step S424, the SMIACC count is compared to 0 to determine if the minimum limit count or lower trip point for decreasing the current sensing threshold $I_{TH}$ has been reached. If it has not been reached, then the processing of the current ISENSE event is completed in step S110, and the AutoSensing algorithm loops back to wait for the next event in step S102 of FIG. 13. If the lower trip point count of 0 for the SMIACC is reached, then the current sensing threshold $I_{TH}$ is decreased in step S426 by one sensing threshold increment. The initial SMIACC, PEA, and RPA counts are again loaded in step S416. The processing of the current ISENSE event is completed in step S110, and the algorithm loops back to wait for the next event in step S102 of FIG. 13.

PACE PULSES—FIGS. 18–20

Returning to FIG. 13, if the next event is not an ISENSE interrupt in step S104, then pace TRIG flag is checked in step S112. If, of course, neither an ISENSE interrupt nor a pace TRIG flag are present, the AutoSensing algorithm remains waiting for the next event in step S102. Assuming that a pace TRIG flag is provided to the microcomputer 34 in step S112, then the "old sense history" is degraded in step S114. The current pace TRIG is processed in step S116, and the algorithm loops back to wait for the next event in step S102. Steps S114 and S116 are depicted in greater detail in FIGS. 18 and 19, respectively.

Figure 18:
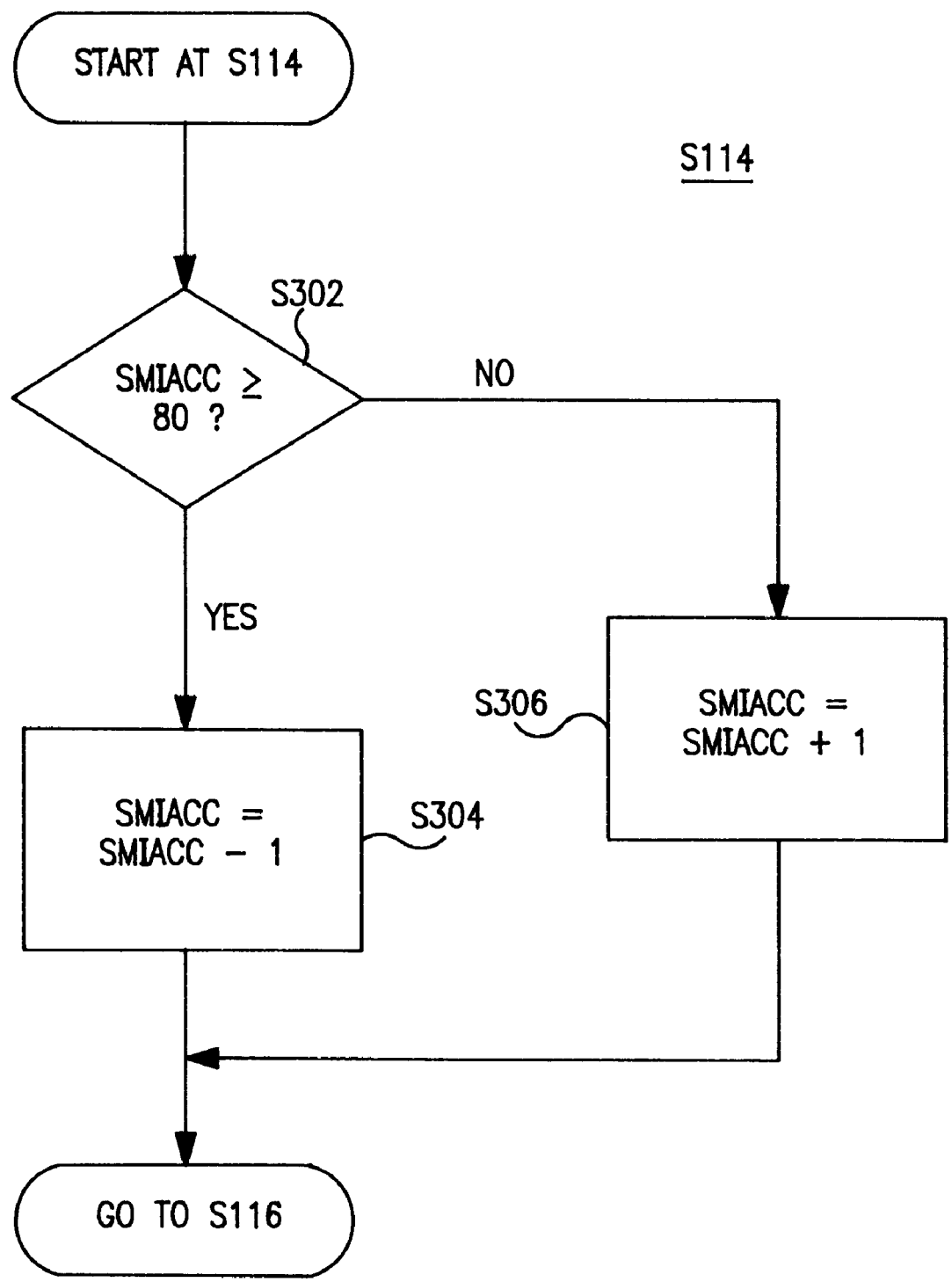
FIG. 18 is a detailed flow chart of step S114 of FIG. 13.

In FIG. 18, the SMIACC count is compared to the initial value of 80 in step S302. If the count is > or =80, then the SMIACC count is adjusted by −1 in step S304. Similarly, if the count is <80 as determined in step S302, then the SMIACC count is adjusted by +1 in step S306. In either case, when the SMIACC count is adjusted, the degrading of the old sense history is completed in step S116 of FIG. 13. The adjusting of the SMIACC count by −1 or +1 is also shown in FIGS. 22 and 23.

Figure 19:
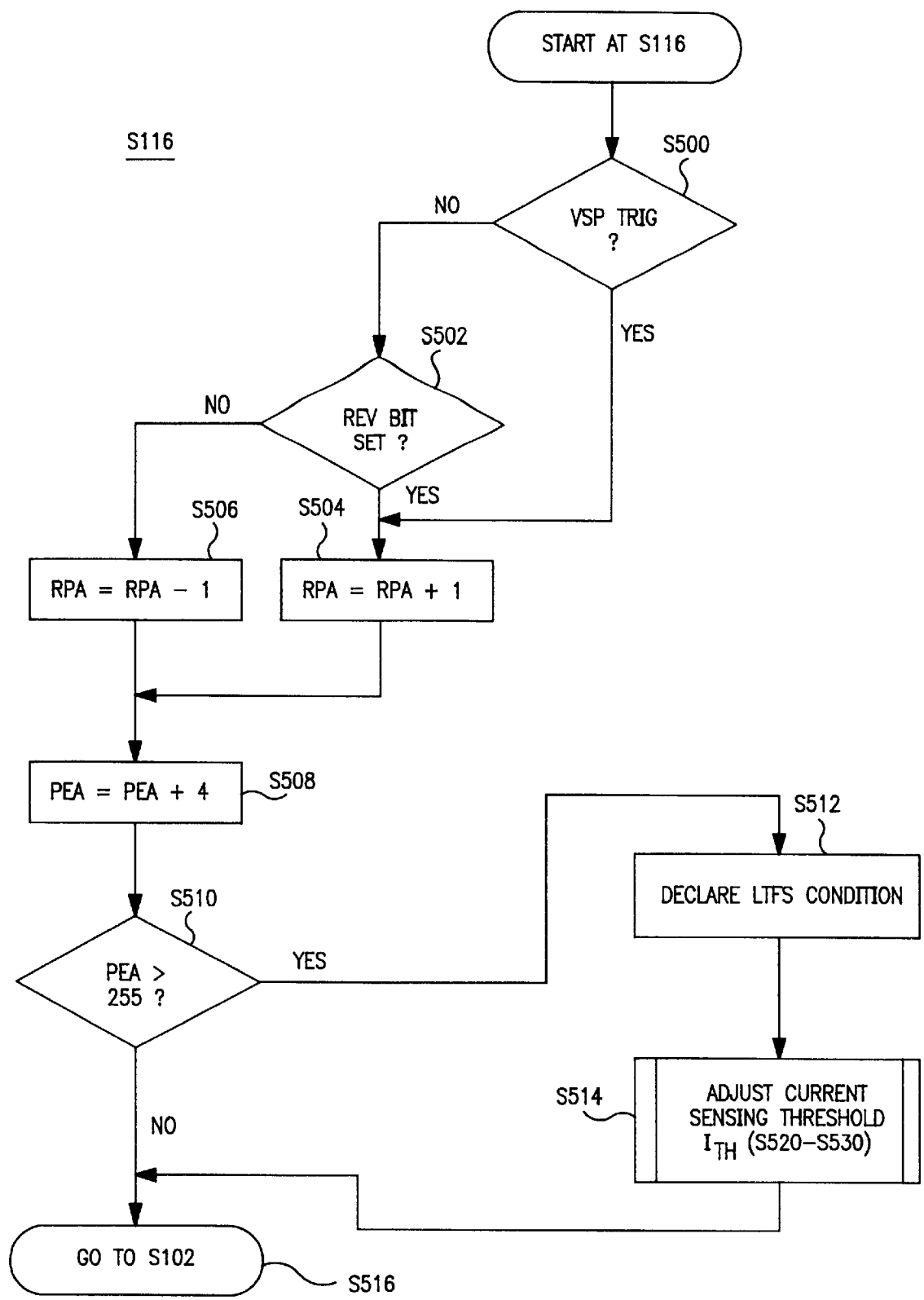
FIG. 19 is a detailed flow chart of step S116 of FIG. 13.

The processing of the current pace TRIG of step S118 commences at step S500 in FIG. 19, where it is determined whether or not the pace TRIG event constitutes a ventricular safety pace (VSP) V-TRIG event. As described above, the VSP feature is present in many IPGs of the type described and (Ventricular Safety Pace following an Apace)triggers a VSP V-TRIG at the end of a VSP delay (typically 110 ms) after noise is detected in a noise sensing window following an Apace.

The VSP V-TRIG events are treated the same as reversion pace trigger events regardless of the reversion status determined by the REV bit set in the read only status register 122. In this regard, if the V-TRIG is not a VSP V-TRIG event, then the status of the REV bit for the ventricular channel is checked in step S502. If either a VSP V-TRIG event is present or if the REV bit is set, then the RPA is adjusted by +1 in step S504 as also shown in FIG. 21. If the REV bit is not set as determined in step S502, then the RPA count is adjusted by −1 in step S506 as also shown in FIG. 21. In this manner, the RPA count is incremented on VSP V-TRIG and reversion V-TRIG events and is decremented on other V-TRIG events.

In respect to the atrial channel, the Autosensing algorithm does not consider the VSP V-TRIG flag of step S500. But it does consider the status of the REV bit 4 in the atrial sense amplifier read only register 122 in step S502.

In both the atrial and ventricular channel operation of the Autosensing algorithm, the RPA count is employed in determining whether or not an LTFS condition or a noise-induced reversion condition exists in a manner described in greater detail below.

After the RPA count is adjusted in steps S506 or S504, the PEA count is adjusted by +4 in step S508. As shown in FIG. 24, the PEA count is adjusted by +4 on a pace TRIG event and adjusted by −16 on each non-refractory ISENSE event. In order to identify periods of little sensing, it is necessary to make a statement about what levels of sensing are acceptable. Looking at the medical literature, we can see that blocks of 4:1 are possible. (an AV condition blocked 4 Atrial events to 1 Ventricular event in a 4:1 block).

Thus, the AutoSensing algorithm should not identify such situations as periods of little sensing. Therefore, in the preferred embodiment a 5:1 block or 20% sensing is chosen as the cutoff below which the period of little sensing response is not invoked. Hence, blocks of 6:1 or greater will be required before they are identified as low percentage sense event situations.

Figure 20:
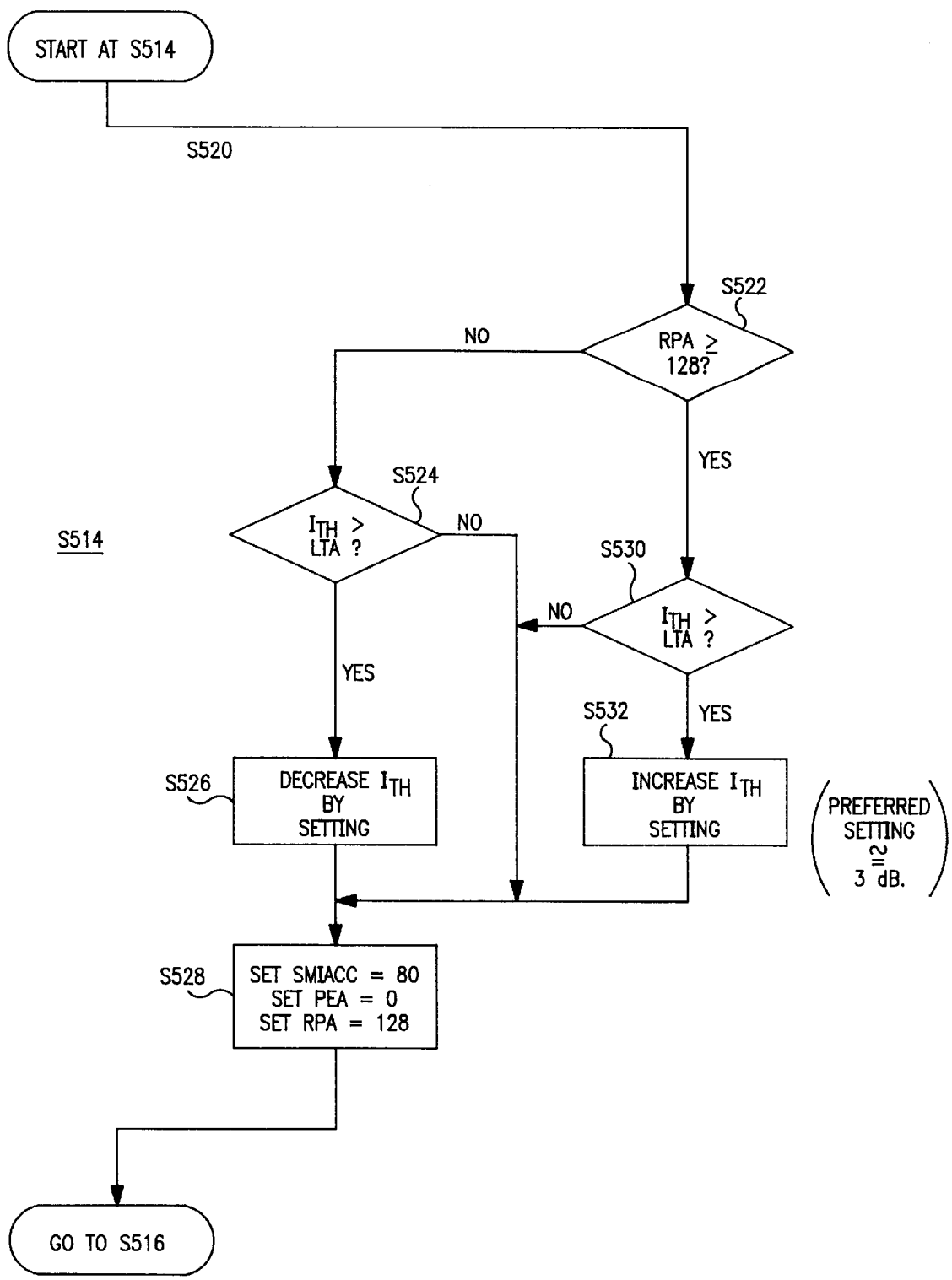
FIG. 20 is a detailed flow chart of step S514 of FIG. 19.

In step S510, the PEA count is compared to its upper boundary value of 255. If the PEA does not exceed 255, then the algorithm loops back to step S102 to await the next ISENSE event interrupt or pace TRIG interrupt. If the PEA count exceeds 255, then a LTFS condition is declared in step S512, and the adjustment of the current sensing threshold $I_{TH}$ is undertaken in step S514.
FIG. 20

In the adjustment of the current sensing threshold $I_{TH}$ in step S514, shown in detail in steps S520–S530 of FIG. 20, it is necessary to determine whether or not the LTFS condition is due to a reversion pacing mode or is simply due to the absence of intrinsic EGM signal peaks exceeding the current sensing threshold $I_{TH}$. The latter condition may be due to a number of factors, including: (1) the simple absence of an intrinsic heart rhythm; (2) the adjustment of a pacing escape interval based on a physiologic sensor or other rate control parameter that is shorter than the underlying intrinsic escape interval of the patient's heart; (3) the particular pacing mode that the IPG is programmed to operate in; (4) the adjustment of the current sensing threshold $I_{TH}$ above the amplitude of the intrinsic EGM signal peak due to over-sensing of large amplitude noise events or because the PDS or nominal base sensing threshold $I_{THb}$ was not set aggressively enough; (5) a sudden drop in the intrinsic signal amplitude to a level below the current sensing threshold $I_{TH}$ (e.g., due to the onset of fibrillation or flutter, lead dislodgment, etc.), or for other reasons.

Central to the AutoSensing algorithm response in the LTFS situation is the concept of returning to a "safe" sensitivity. When periods of little sensing occur, the algorithm starts adjusting the current sensing threshold $I_{TH}$ on a "drift" back towards the LTA sensing threshold setting in hopes of regaining lost sensing. Since by the process defined in FIG. 17 earlier, the LTA sensitivity is a slow-responding filtered value of the sensing threshold at which events have been sensed in the recent past, it is assumed to be a safe value to return to in the event the IPG detects a condition of little sensing (LTFS). When the condition of little sensing is initially indicated by the PEA in step 510, the RPA must be checked at step S522 before the LTA can be adjusted for an LTFS condition. Then the value of the LTA is compared to the current sensing threshold $I_{TH}$, and if found to be more sensitive than LTA (step 530), the current sensing threshold is adjusted by one setting less sensitive in step S532. This will result in a behavior which can recover from noise reversion conditions in the conditions where the sensing threshold $I_{TH}$ was more sensitive than the LTA.

Figure 26:
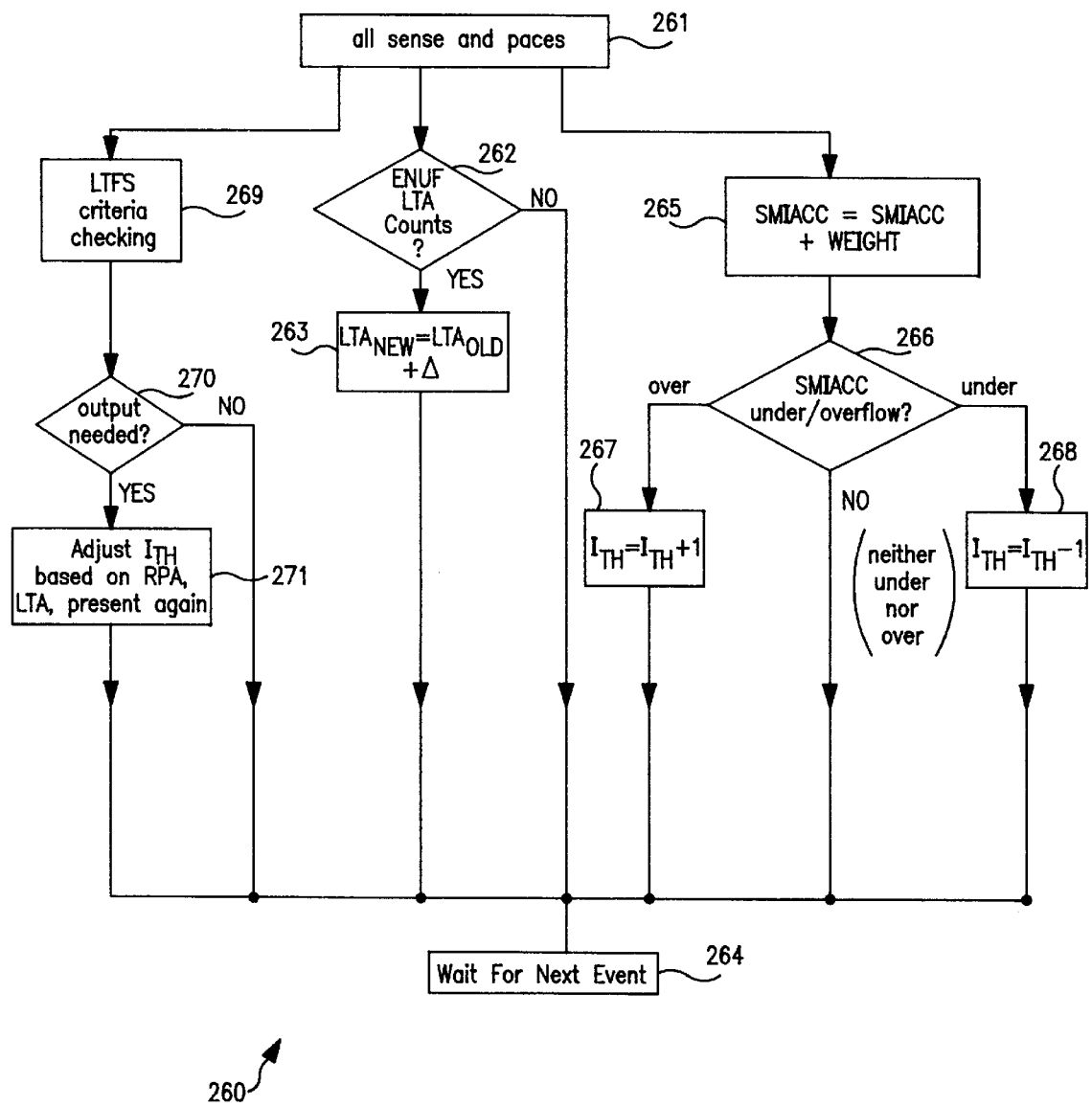
FIG. 26 is a register manipulation oriented flow chart that traces the steps required for adjustment of the sensing threshold in a preferred embodiment of this invention.

If instead step S522 found the RPA<128, the current sensing threshold is compared to the LTA value in step S524. If the $I_{TH}$ is found more sensitive than LTA, the current sensing threshold is adjusted by one setting less sensitive in step S526. This behavior allows the sensitivity to regain sensing if it had been adjusted to be less sensitive than the LTA value, and less sensitive tan the peak of the intrinsic signal, to avoid situations, for example of stuck values due to possible temporary noise oversensing. FIG. 26 Shows what the curve of the LTA value looks like over time vis-à-vis Shi and Slo valves. The insert 25a shows the expected behavior as LTA approaches Shi in accord with this invention.

RECAP SUMMARY

To describe succinctly, a concept that is central to the sensitivity adjusting algorithm is that only good reliable margin measurements will be considered in the adjustment of gain calculation. The description above is of the preferred forms of hardware and software to accomplish this.

As one featured function, a valid margin measurement is assumed to have taken place only on non-refractory events if the common mode or absolute amplitude overrange of the amplifier is not exceeded, if an excessive noise floor condition does not exist (i.e., the peak noise signal does not exceed the current sensitivity setting), if the ELS condition is not violated (i.e., the sense event did not persist for a period of time that would be longer than expected), a subsequent event does not fall within the SMI window, and if the ventricular sense does not occur immediately following an atrial paced event. (Sub combinations of these elements of proof of reliability can be used).

To adjust the gain then, four registers, accumulators or counters are maintained by the algorithmic processes or programs that are used for each sense amp. Thus a duplicate set should be maintained for each additional sense amplifier. If there are more than one, say, a separate one for the atrial and the ventricular sensing, or in the case where atrial and ventricular sensing might be multiplexed to one sense amplifier, a set should be maintained for each input electrode.

The general function of these counters is described visually in FIGS. 21–25. In accord with the rules for maintaining each counter a value representing the counter may be maintained, such as the LTA value, which can only be updated when a counter LTASENSE_COUNT, has been incremented 16 times, for example. The registers operate together as follows.

The LTA counter is a counter for which every 16 reliable sensed events it gets updated by the formula:

LTA (i.e., the sensitivity setting or gain value)=LTAold (i.e., the old sense gain value)+($I_{TH}$current−LTAold)/128

The above formula allows LTA value to only slowly moderate the LTA toward the Shi as in the curve shown in FIG. 25. Reliable sensed event criteria for the LTA is any sense in a non-refractory period which is not determined to have been noise or out of amplitude range as described in detail above.

General Process Description

FIG. 26 is a flow chart in which the cooperative action of these registers is outlined as a process 260 each time beginning with a sense at 261 a representation of which is forwarded to the LTFS program 269, if it's a paced event, to the LTA program step 262 if it's a 'reliable' sense event, and to the SMIACC program step 271, if it's a sense event in accord with the SMIACC criteria previously described. A decision point is reached each time a count is added to the registers governed by decision steps 269, 262, and 266. If there is no output needed from steps 270 or 262 or 266 the following step is 264, to do nothing but wait for the next sense and return to step 261 when it occurs.).

Determination of the percentage of sense events will be accomplished by maintaining a PEA (Paced Event Accumulator). The PEA will be initialized at its lower boundary of "gamma" (a lower boundary value) and will have an upper boundary of "lambda" (an upper boundary valve). The initial and minimum value of the PEA counter will be zero (This corresponds to the discussion of the FIG. 24). The PEA will be adjusted by a certain positive weighting on every paced event and adjusted by a negative weighting on every non-refractory sense event (all reliable and unreliable margin measurements are counted, regardless of whether they are PVC (premature ventricular contractions) or non-PVC). When decremented below the lower boundary, the value of the counter will "stick" at or near its lower boundary of gamma. Once the value of the PEA exceeds its upper boundary an indication of "Long Time Few Senses (LTFS)" would be found and a signal indicating this could be generated and used. In this manner, the LTFS will be determined from a rolling window on only the most recent events. The status of the PEA should be checked after each additive operation is performed on it.

When a period of LTFS is encountered, the response of the algorithm is likely to be an adjustment of the current sensitivity to what is believed to be a more appropriate setting. The details of this adjustment are dependent on several factors. These include whether the current sensing threshold is above or below the baseline sensitivity and whether the device is delivering a high percentage of noise invoked reversion paces. The RPA (Reversion Pace Accumulator) is used to accomplish the latter (FIG. 21). It's value is only checked when an LTFS situation is encountered. To calculate the RPA, the algorithm maintains a definition of what is an unacceptably high level of reversion pacing for this gain setting. Our preferred definition is that if more than 50 % of recent paces are reversion paces, then a reversion pacing situation exists. The definition is done in this manner because we want to know what is happening that has led to the present LTFS situation but not what may have happened a long time ago.

Like the PEA, the RPA also classifies each event, assign a weighting to that event, and adds it to the RPA. However, unlike the PEA, the RPA does not trigger the recognition of any event when its exceeds its upper or lower boundary.

The events which will be included in figuring the running sum of the RPA will be non-reversion paces, reversion paces, and non-refractory sense events (of any kind.). The occurrence of the non-refractory sense events will be used as an indication that older reversion data should be removed from the RPA. The RPA will be initialized at a value of "epsilon" and will have an upper boundary of "lambda" and a boundary of "gamma." When reversion paces occur, a weighting will be added to this RPA counter until the upper boundary is exceeded and the counter's value "sticks" at or near that upper boundary. Similarly, when non-reversion paces occur, a weighting equal to the reversion pace weighting will be subtracted from the counter until the lower boundary is exceeded and the counters value "sticks" at or near that lower boundary. Sense events will cause the RPA to be adjusted with a weighting equal to the paced event weighting towards "epsilon" as a means of flushing older reversion status from the accumulator. Once an LTFS indication is had from the PEA, the RPA will be examined and if its value is greater than "epsilon", a confirmation of the LTFS situation by noting that there is a reversion pacing situation then a signal can be generated and the LTA gain appropriately changed in accord with FIG. 26. After this LTFS confirmation, the value of the RPA is reinitialized and the process restarted. If there is not a significant number of reversion paces, the value of the counter will simply stay at gamma. If there is a very low percentage of pacing occurring the value of the RPA will oscillate around an initial epsilon.

By following the above discussion it can be seen that the sensitivity(gain) can be adjusted away from or towards the baseline sensitivity in a condition of LTFS, only if the PEA and the RPA both indicate that it is warranted. Both the PEA and RPA would be reinitialized and the process restarted after an LTFS decision is made.

Operation of the RPA and PEA depends on weightings. The number and weighting of the non-refractory sense events, respectively, S and MP, the number and weighting of the paced events, respectively, P and NP, and a trip value, LP may be used. The value of the PEA when an LTFS situation occurs can then be expressed as NP(P)−MP(S)≧LP. This expression can be manipulated to provide:

$$\frac{S}{P} \leq \frac{NP}{MP}\left(1 - \frac{LP}{NP(P)}\right);$$

(where "L" is an alternative name for lambda). The percentage of total events that are paced events can be expressed as $$\% \text{ Paced events} = \frac{P}{S+P} = \frac{1}{1+(S/P)}$$

From the above expressions we can infer that the ratio of NP/MP controls the final percentage of events that will indicate an LTFS situation (i.e., as P gets very large) whereas the ratio LP/NP controls the response time before an LTFS situation is identified. The weighting of the paced and sense events is chosen to be ratio of 1-to-4 to accommodate a 5:1 block. A 5:1 block would be pacing 80% of the time and this percentage would always be less than the LTFS asymptote of 80% pacing. A 6:1 block is then required before it will be recognized as a LTFS situation. The minimum number of paces the algorithm must look at before it can determine an LTFS situation is LP/NP. (The device must be pacing 100% of the time for this to be indicated). The ratio LP/NP is chosen to be 64 to roughly correspond to a one minute interval at a rate of 60 BPM. Hence, the device must be pacing for about one minute at a rate of 60 BPM for an LTFS situation to be identified. If we scale the parameters to allow NP=4, MP=16, gamma=0, and LP=255, it will be easy for firmware to check for an LTFS situation as the PEA will simply overflow (that is, be larger than 255) when the trip value is reached.

Turning to the RPA we have to decide what the number of recent paces sampled to determine reversion pacing will be, what weighting will be used in the counter scheme, and what the upper and lower boundaries of the counter will be. In order to facilitate the implementation for firmware we will pick the boundaries to be at gamma=0 and lambda=255. Then, based on an overflow or overflow situation, the firmware can reset the counter and producing the required sticking behavior. The choice of the sample size for determining reversion will be based on the fact that the fastest the PEA will satisfy the LTFS criteria is 64 consecutive paces. Thus, 64 paces becomes the sample size and it follows that epsilon should then be 127 and the event weighting should be 2. Thus, when LTFS occurs, reversion pacing is indicated if the value of the RPA is greater than 127.

Sense Margin Indicator Accumulator Functioning

This algorithm generally classifies events, assigns a weighting to each event, and adds that weighting to the value in the SMIACC. When the value of the SMIACC crosses a numerical boundary, its over or underflow is a signal to make an appropriate adjustment to the sensing threshold or gain. By allowing classification of the events which will be included in the running sum, not only be reliable margin measurements, but unreliable measurements and paced events can be included as well. The occurrence of the latter events will be used as an indication that older margin measurement data should be removed from the SMIACC. Thus it does not depend on a specific number of events to occur in order to determine that sense amp gain should be adjusted.

The SMIACC will be initialized at a value of epsilonS and will have an upper trip point of lambdas and a lower trip point of gammaS. When margin high measurements are made a weighting will be added to the counter until the upper trip point is exceeded and the sensitivity is reduced by one setting. On the other hand, when margin low measurements are made, a weighting will be subtracted from the counter until the lower trip point is exceeded and the sensitivity is increased by one setting. Acceptable margin measurements, unreliable margin measurements, and paced events will cause the SMIACC to be adjusted with specific weightings towards epsilonS as a means of flushing older margin measurements from the accumulator. The weighting assigned to a particular event will differ depending on whether the current value of the SMIACC is greater than or less than its initial value epsilons. FIG. 26 shows the overall operation in a simplified process model form.

Once a sensitivity adjustment decision is made the SMI-ACC is reinitialized to epsilonS and then restarts. On the other hand, when there is any absence of a particular trend in the sensitivity, the value of the counter will simply oscillate around epsilonS. The response time of the algorithm is determined by the event weights and the number that occur and the difference between the upper and lower trip points and the initial setting of the event accumulator (SMIACC). In this manner, the algorithm permits different response times for increasing and decreasing sensitivities, eliminates sampling windows by keeping a running sum of events, works in conjunction with pacing, maintains an historical perspective on the margin measurements, and permits PVC'S to be treated differently than other sense events. These advantages are realized with relatively little increase in computational overhead.

There are really eight different events that must be considered when determining the relative weighting of events in the SMIACC. These are a reliable non-PVC sense with high (we call such high sense values $S_{NH}$ instances with a weighting of $M_{HN}$), acceptable (called $S_{NA}$ instances with a weighting of $M_{NA}$), or low margins ($S_{NL}$ instances with a weighting of $M_{NA}$), a reliable PVC sense with high (called $S_{PH}$ instances with a weighting of $M_{PH}$), acceptable ($S_{NA}$ instances with a weighting of $M_{PA}$), or low margins ($S_{PL}$ instances with a weighting of $M_{PL}$), an unreliable sense (called Su instances with a weighting of Mu), and a paced event (P instances with a weighting of $N_E$). Note that the weighting of similar events does not necessarily have to be the same when the value of the counter is above or below epsilonS. The value of the SMIACC when a sensitivity increase is indicated can then be expressed as follows (, as appropriately subscripted to enhance this explanation).

$$-M_{NH}S_{NH}-M_{NA}S_{NA}+M_{NL}S_{NL}-M_{PA}S_{PA}+M_US_U-N_EP \geq \text{epsilonS}-\text{gamnmaS}$$

(This is the sum of all occurrences of all the named events in this paragraph just above.) This expression can be simplified as $$-M_HS_H-M_AS_A+M_LS_L-M_{PA}S_{PA}+M_US_U-N_EP \geq T_{EL}$$

where $M_H=M_{NH}=M_{PH}$, $M_A=M_{NA}=M_{PA}$, $M_L=M_{NL}=M_{PL}$, $S_H=S_{NH}+S_{PH}$, $S_A=S_{NA}+S_{PA}$, $S_L=S_{NL}+S_{PL}$, and $T_{EL}=$ epsilonS−gammaS. Using the fact that the total number of sense events is related to each individual class of sense event as $S=S_H+S_A+S_L+S_U$, we can substitute for $S_H$ in the above expression to yield $$S_L \geq \frac{M_H}{M_L+M_H}\left(1-\frac{M_H-M_A}{M_H}\frac{S_A}{S}-\frac{M_H-M_U}{M_H}\frac{S_U}{S}+\frac{N_EP}{M_HS}+\frac{T_{EL}}{M_HS}\right)$$

By choosing to set $M_H=M_A=M_U$ it is possible to eliminate the terms pertaining to the fractions of acceptable margin and unreliable events. Thus, $$S_L \geq \frac{M_H}{M_L + M_H}\left(1 + \frac{N_E P}{M_H S M_H} + \frac{T_{EL}}{S}\right)$$

This expression indicates what fraction of the sense events must be low margin events for a given total number of senses and a given fraction of paced events for the sensitivity to be increased. Consider the situation where there is 100% sensing and no pacing (i.e., the middle term in the brackets is eliminated). Then as we look at a larger and larger number of sense events (i.e., as S gets very large), the percentage of margin low events required for a sensitivity change will asymptotically approach $M_H/(M_L+M_H)$. In order to insure that the algorithm tracks the largest amplitude event we would like this asymptotic value to be greater than 50%. (In the preferred embodiment the corresponding threshold is 61.5% (i.e., 8/13). Any asymptote close to this value would probably be reasonable.)

The response time of the algorithm (again with no pacing) is determined by the ratio $T_{EL}/M_H$. As this ratio increases the response time of the algorithm will be slower because a higher percentage of margin low events will be required to cause the sensitivity change. The converse is also true. The preferred algorithm had a fixed response time (in the absence of any pacing) of 16 events for an increase in sensitivity (response time would vary significantly with the introduction of pacing). The response time of the present algorithm will vary with the number of sense events examined (as well as with the number of paces). The value of $T_{EL}/M_H$ is a compromise to between the response time and the minimum number of 100% low margin senses that will initiate a sensitivity increase.

As the ratio of paced-to-sense events the fraction of margin low events required for a move becomes greater than one. This implies that, for high percentage paced situations, we will never increase the sensitivity. The weighting of the paced events should be preferably chosen such that a sensitivity change will occur for a 5:1 block, but not for a 6:1 block as per our definition of LTFS in the previous section.

Based on all these criteria the choice of MH=MA=MU=8, ML=5, NE=1, epsilonS=79, gammaS=0, and $T_{EL}$=80 ($T_{EL}$/MH=10) will be preferred. These weightings provide us with an asymptotic sense margin low requirement of 61.5%, a sensitivity change response at 5:1 block but not at 6:1 block. Also, with this choice of weightings, it follows that the firmware(operated preferably as described with reference to the relevant flow chart FIGs.) simply needs to identify a counter underflow as the means of indicating a need for an increase in sensitivity.

The preceding discussion has dealt with the ratio of events and time constant for an increase in sensitivity. Analogous equations and discussion pertain to a decision to decrease sensitivity. The main difference being that a sensitivity decrease is signaled by SMIACC counter overflow(i.e. >lambdaS), whereas underflow (less than gamma) signaled a need to increase sensitivity. One other notable difference is the fact that the response time in the preferred algorithm is 36 events (i.e., roughly twice as long as what it was in the increasing situation).

General process description.

FIG. 26 is a flow chart in which the cooperative action of these registers is outlined as a process 260 each time beginning with a sense at 261 a representation of which is forwarded to the LTFS program 269, if it's a paced event, to the LTA program step 262 if it's a 'reliable' sense event, and to the SMIACC program step 271, if it's a sense event in accord with the SMIACC criteria previously described. A decision point is reached each time a count is added to the registers governed by decision steps 269, 262 and. If there is no output needed from steps 270 or 262 or 266 the following step is 264, to do nothing but wait for the next sense and return to step 261 when it occurs. Thus the complexity of operation of the several registers to accomplish the inventive adjustment to the input sense amplifier gain is expressed in a simple form in this high level flow chart of FIG. 26. Special case of the Atrial sense amp gain control for VDD pacing.

Figure 13A:
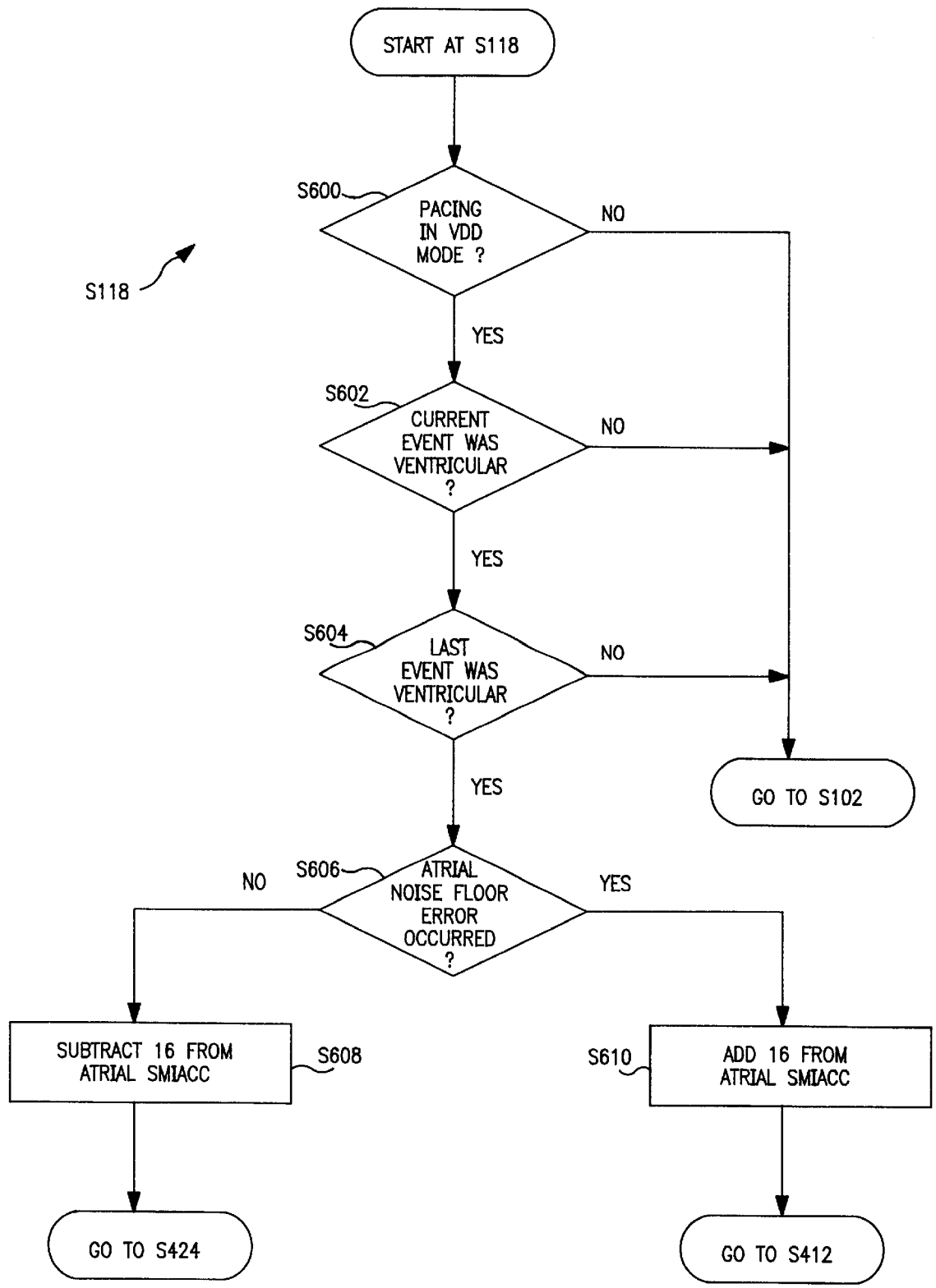
FIG. 13a is a detailed flow chart of step S118 of FIG. 13.

It should also be noted, with reference to FIG. 13a, since there will never be pacing in this mode in the atrium when an implanted pacemaker or IPG is set in VDD mode, that some other mechanism should substitute for LTFS for the atrial amplifier gain adjustment(i.e., step 269 in FIG. 26). Step 118 is detailed in this figure starting with step 600 (which can be ignored if the pacer is permanently in this mode but not otherwise), which will refer back to FIG. 13's next step if the pacer is not in VDD mode. If the only events found in the last two events are ventricular (determined by steps S602, and S604), we check to see if a noise floor error condition occurred(that is, the atrial sense amplifier was in noise reversion status during the checking of these two last events). If there is no such error we subtract a relatively large value from the atrial SMIACC (because the other condition for not finding an atrial event between two ventricular events would most commonly be undersensing) or add the same large value if such an error occurred (to get above the noise floor when the SMIACC overflows to push the threshold higher). The preferred value is 16. Then the program returns to the steps which check for under and over flow of the SMIACC.

Accordingly a system has been fully described and summarized that automatically modifies the gain on the input sense amplifier circuit for an implantable medical device in order to find the optimum setting for the patient in ordinary circumstances as well as to modify that gain as needed. While many modifications may be made to the teachings herein, they are only limited by the claims that follow.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

These terms capitalized generally represent names given for signals but some are common terms and some are common only to the pacing field. Their meaning is summarized in the below list in the order of appearance in the text above. (Signal names can be line names or vice-versa).

| | |
|---|---|
| $I_{TH}$ | adjustable current sensing threshold |
| LTA | Long Term Average |
| DDDR | (a known pacing term) |
| MH | Margin High |
| ML | Margin Low |
| EGM | (Electro-Gram) |
| PDS | physcian determined setting |
| IPG | Implantable Pulse Generator |
| V-Pace | ventricular pacing |
| V-TRIG | ventricular triger |
| A-PACE | Atrial Pace or Atrial Pacing |
| POR | Power-on-Re-set |
| ADC | Analog to digital converter (common term.) |
| P-waves | (a known electro cardiogram term) |
| ISENSE | Intrinsic Sense |

-continued

| | |
|---|---|
| VISENSE | Ventricular Intrinsic Sense |
| AISENSE | Atrial Intrinsic Sense |
| P,R and T | (common designator for parts of electrocardiogram) |
| RAM/ROM | (common term for memory types) |
| A-TRIG | Atrial Trigge (signal name) |
| V-TRIG | Ventricular Trigger (signal name) |
| V-A | Ventricular-Atrial (meaning Ventricular to Atrial as in an interval) |
| A-V | Atrial Ventricular |
| ARP | Atrial Refractory Period |
| V-PACE | Ventricular Pace |
| PVARP | Atrial Refractory Period |
| VRP | Ventricular Refractory Period |
| URL | upper rate limit |
| DIFFAMP | differential amplifier (name of one) |
| CDHW | capture (evoked response) detection circuit (short for Capture Detection Hardware) |
| TRANSAMP | transimpedance amplifier |
| ABSVAL | a rectifying circuit (short for absolute value) |
| ANF | Analog Noise Filter |
| CLKGEN | clock generator |
| DAK | digital amplitude comparators |
| DETLOGIC | detection logic |
| NOISEL | noise floor exceeded low |
| NOISEH | noise floor exceeded high |
| OVRNG | over-range (bit name) |
| SMI | Sense Margin Indicator |
| SML | Sense Margin Low (bit name) |
| SMH | Sense Margin High (bit name) |
| ELS | Excessively Long Sense |
| REV | Reversion status indicated by this bit |
| ELSEVNT | Excessively Long Sense Window Event (bit name or signal name) |
| SACR | Sensing Assurance Control Register |
| TIMING | lines that cordinate timing in FIG. 1 |
| RING | terminal name |
| TIP | terminal name |
| INREF | (Input Reference Voltage) |
| DIFFAMP | terminal name |
| "VR" | reference voltage |
| UR | Unipolar Ring |
| UT | Unipolar Tip |
| IBLANK | Current Blanking (a signal name) |
| CLRSPSM | (clear the "SP and SM" inputs) 9 a signal name) |
| ENATTEN | Enable Attenuator (a signal name) |
| NCDSFW | (non Capture Detect Slew Filter Window) |
| IBLANK | (a signal name) used to open switches 145, 149 on a V or ATRIG and reclose them after. |
| RECHARGE | (a pacemaker operation) |
| AVDD | (signal name for a voltage service) |
| DAC | (Digital to Analog, a common circuit name) |
| ANFEGM | Analog Filtered EGM (a signal name) |
| LINTEST | Line Test (a signal name) |
| IVIGIN | the sum of IEGM and ANFEGM |
| IEGM | (common term for Intra Cardiac Electro-Grain) |
| VREG | Signal name for a reference voltage |
| Power Down | Our Amplifier Mode |
| ESENSE | Evoked Sense (a signal name) |
| TBLANK | Transamp Blanking (a signal name) |
| XBLANK | Blanking signal to the Transamp of the other chamber (cross-blanking) |
| AXBLANK | Atrial cross Blanking (a signal name) |
| VXBLANK | Ventricular cross Blanking (a signal name) |
| ATBLANK | Atrial T Blanking (a signal name) |
| VTBLANK | Ventricular T Blanking (a signal name) |
| AFBLANK | Atrial Filter Blanking (a signal name) |
| VFBLANK | Ventricular Filter Blanking (a signal name) |
| CLKGEN | Name of Clock Circuit |
| EMI | (Common term for ElectroMotive Interference) |
| PACETRIG | Pacing pulse Trigger (meaning it could be Atrial or Ventricular) |
| PLATCH | Pace Latching (a signal name) |
| FBLANK | Filter Blanking (either Atrial or Ventricular) |
| IVNOISEH | Noise floor high threshold signal name (Input entricular) |
| Noise H | Multiple of $T_{TH}$ representing the high noise threshold |
| Noise L | Multiple of $T_{TH}$ representing the low noise threshold |
| ML comp & MH Comp. | Outputs form register 124 |
| INOISE H | Input Noise High (signal name) generated by DAC 118 |

-continued

| | |
|---|---|
| INOISEL | Input Noise Low (signal name) generated by DAC 118 |
| ICOMP | a signal name, one of generatable by DAC 118 when IVIGN exceeds one of those three holds |
| $I_{THb}$ | Current Sensing Threshold Baseline |
| MH | Margin High (a threshold level value) |
| ML | Margin low (a threshold level value) |
| (CDW) | Capture Detection Window (a timing window) |
| Ecomp | evoked response comparator output |
| NDIGTEST | (a signal name) |
| NFLCOMP | noise floor (a comparator in DAC 118) |
| ELSWIN | ELS Window short for Excessively long Sense Window |
| STARTQT | Start Quiet Time (a signal name) |
| AMASK | Atrial Masking (a signal name) |
| VMASK | Ventricular Masking |
| AREV | Atrial Reversion |
| VREV | Ventricular Reversion |
| QT | Quiet Timer |
| SMH | (Sense Margin Hi) |
| SML | (Sense Margin Low) |
| SMIWIN | SMI window (Sense Margin Indicator) |
| MASK | (a signal name) (can be Atrial or Ventricular too) |
| AS | adequate sense (a signal or value name) |
| LTFS | Long Term Few Senses |
| PEA | Paced Event Accumulator |
| RPA | Reversion Pace Accumulator |
| LTA | Long Term Average (An accumulator Name) |
| SMI Accumlator | (SMIACC) |
| POR | Power On Reset (state an IPG assumes after a reset condition) |
| SMIACC | (Sense Margin Indicator Accumulator) |
| PDS | Physician Determined Sensitivity level |
| VSP | (Ventricular Safety Pace following an A pace) |
| LTASENSE-COUNT | (an Accumulator Name) |
| VSP | Ventricular Safety Pace |
| S | Number of non refractory events (in RPA or PEA) |
| MP | Weight of S |
| P | Number of paced events (in RPA or PEA) |
| NP | Weight of P |
| LP | Trip Value |
| BPM | Beats per minute |
| "gamma" | (a lower boundary valve) |
| "lambda" | (an upper boundary valve) |
| PVC | premature ventricular contractions (a common Cardiology Term) |
| epsilon S | SMIACC's invitation value |
| lambda S | SMIACC's upper trip point |
| gamma S | SMIACC's lower trip point |
| $S_{NH}, S_{NA}, S_{nb}, S_{PH}, S_{PA}, S_{BL}, S_u$ | Kinds of Senses (pages 70,71) |
| $M_{NH}, M_{NA}, M_{NL}, M_{PH}, M_{PA}, M_{PL}, M_u$ | Kinds of Weightings |
| P | again, the variable indicating a paced event, or a number of paced events |
| $N_E$ | Weighting for paces |

What we claim is:

1. A method for automatically adjusting a present gain/threshold parameter value of an input sense amplifier for use in an implantable medical device which operates said input sense amplifier to receive and, responsive to electrical activity of sufficient intensity that can be called sufficient senses, determine senses of event specific pulses of electrical activity native to a body into which said device is designed for implantation, and from said sufficient senses said amplifier produces a sense amplifier output, said method comprising:

determining adjustments to be made to said input sense amplifier present gain/threshold parameter value based on current values of at least two indicator means for monitoring sense amplifier output, determining a condition and producing a signal output, keeping track of said current values for said at least two indicator means, a first of said at least two being a Long Time Few Sense (LTFS) indicator means for monitoring sense amplifier output, determining a condition relating to LTFS, and producing a signal output from said LTFS condition determination and a second of said at least two being a Long Term Average (LTA) indicator means for monitoring sense amplifier output, determining a condition relating to LTA, and producing a signal output from said LTA condition determination, said keeping track steps comprising:
tracking said at least two indicator means from each input sense amplifier output by,
operating said LTFS indicator means to (a) monitor said input sense amplifier output to determine whether said LTFS indicator means has received an insufficient number of senses in a tracked period immediately preceding any given sense amplifier output and (b) if said LTFS indicator means has determined a condition of having received such insufficient number of senses, generating an LTFS output signal representative of said condition,
operating said LTA indicator means, to monitor said input sense amplifier for a valid sense output signal, and to count and maintain an LTA count of said valid sense output signals, wherein when a sufficient number of said valid senses has been counted said LTA count is deemed sufficient and, then resetting the LTA count and adjusting an LTA signal value based on comparing a last LTA signal value to said present sense amplifier gain/threshold parameter value, but only adjusting said LTA signal value if there is an LTFS output signal present when said LTA count is deemed sufficient.

2. The method of claim 1 wherein the implantable medical device monitors reversion status and generates a signal on determination of reversion status, the step of operating said LTFS indicator means additionally to perform the step of determining whether there is a reversion status indicated by checking for said signal of determination of reversion status before generating said LTFS output, but only performing the step of generating said LTFS output signal on a determination that such a condition of reversion status exists.

3. The method of claim 2 wherein the implantable medical device monitors paced and sensed events and wherein in operating said LTFS indicator means before said LTFS indicator means generates an LTFS signal, manipulating a value stored in a Paced Event Accumulator (a PEA value) by adding to said PEA value a first incremental value for each paced event, and subtracting a second incremental value larger than said first incremental value for each sensed event to said stored PEA value, wherein said stored value moves further on a sensed than a paced event, but only when said stored PEA value reaches a preset value, does said method generate an LTFS signal.

4. The method of claim 3 wherein the implantable medical device monitors noise reversion status and generates a noise reversion status indicated signal on determination of reversion status, and wherein before said LTFS indicator means generates an LTFS signal, checking for said noise reversion status signal, but only after performing this step of checking, issuing an LTFS signal if there is said noise reversion status indicated signal.

5. The method of claim 4 wherein if there is a condition of noise reversion said LTA indicator means will adjust the present gain/threshold parameter value to increase sensitivity, but only if the LTA value is higher than the present gain/threshold parameter value, and if there is no condition of noise reversion said LTA indicator means will adjust the value of the present gain/threshold parameter value to decrease sensitivity but only if the LTA value is lower than the present gain/threshold parameter value.

6. The method of claim 1 wherein the implantable medical device comprises an Implantable Pulse Generator operating in VDD pacing status and wherein said VDD status comprises sensing of ventricular and atrial events, wherein the step of operating said LTFS indicator means additionally performs the step of determining whether there have been two ventricular events sensed with no intervening atrial sense, but said LTFS indicator means only generates said LTFS output signal on the determination that there has been two ventricular events sensed with no intervening atrial sense.

7. The method of any of claims 1–5 wherein a third one of said at least two indicator means, said third one being a Sense Margin Indicator Accumulator (SMIACC) indicator means for holding an adjustable SMIACC value in a SMIACC memory register means for holding said adjustable SMIACC value which performs steps of monitoring and adjusting said input amplifier output and
if one of said sense amplifier outputs is above a predetermined but adjustable margin value, said third one adjusts said SMIACC value stored in said SMIACC register memory means in a first direction, and wherein these steps of monitoring and adjusting comprise,
if said one of said outputs is below a lower second predetermined level, then adjusting said SMIACC value stored in said register memory means in a second and opposite direction, and
operating said SMIACC indicator means to monitor said SMIACC value wherein;
when said SMIACC value is below a predetermined low value producing an output signal representative of underflow from said third indicator means and,
when said SMIACC value is above a predetermined high value above said register level value, then producing an output signal indicative of overflow, and
at such time as an output value representing underflow or overflow is produced by said SMIACC indicator means, adjusting the input sense amplifier gain/threshold parameter value, upward or downward on the basis of whether there was an underflow or overflow value produced by said third indicator.

8. The method of any of claims 1–5 wherein a third one of said at least two indicator means, said third one being a Sense Margin Indicator Accumulator (SMIACC) indicator means for holding an adjustable SMIACC value in a SMIACC memory register means for holding said adjustable SMIACC value which performs steps of monitoring and adjusting said input amplifier output and
if one of said sense amplifier outputs is above a predetermined but adjustable margin value, said third one adjusts said SMIACC value stored in said SMIACC register memory means in a first direction, and wherein the steps of monitoring comprise,
if said one of said outputs is below a lower second predetermined level, then adjusting said SMIACC value stored in said register means in a second and opposite direction, and
operating said third one to monitor said SMIACC value wherein;
when said SMIACC value is below a predetermined low value producing an output signal representative of underflow from said third one and, when said SMIACC value is above a predetermined high value above said register level value, then producing an output signal indicative of overflow, and at such time as an output value representing underflow or overflow is produced by said third one, adjusting the input sense amplifier gain/threshold parameter value, upward or downward on the basis of whether there was an underflow or overflow value produced by said third indicator, and wherein in operating said third one to monitor said SMIACC value, performing a step of determining a range of amplitude for each sense and assigning a weight value for each input amplifier output based on said range, then adding a first predetermined change increment value to said SMIACC value for each input amplifier output above a midrange of values, and subtracting a second predetermined change increment value from said SMIACC value for each input amplifier output in the midrange of values but above a center of said midrange, and subtracting a third predetermined change increment value from said SMIACC value for each input amplifier output that is below said midrange of values, and adding a fourth predetermined change increment value to said SMIACC value for each input amplifier output that is within said midrange but below a center of said midrange.

9. The method of any of claims 1–5 wherein a third one of said at least two indicator means, said third one being a Sense Margin Indicator Accumulator (SMIACC) indicator means for holding an adjustable SMIACC value in a SMIACC memory register means for holding said adjustable SMIACC value which performs steps of monitoring and adjusting said input amplifier output and if one of said sense amplifier outputs is above a predetermined but adjustable margin value, said third one adjusts said SMIACC value stored in said SMIACC register memory means in a first direction, and wherein the steps of monitoring comprise, if said one of said outputs is below a lower second predetermined level, then adjusting said SMIACC value stored in said register means in a second and opposite direction, and operating said third one to monitor said SMIACC value wherein;

when said SMIACC value is below a predetermined low value producing an output signal representative of underflow from said third one and, when said SMIACC value is above a predetermined high value above said register level value, then producing an output signal indicative of overflow, and at such time as an output value representing underflow or overflow is produced by said third one, adjusting the input sense amplifier gain/threshold parameter value, upward or downward on the basis of whether there was an underflow or overflow value produced by said third indicator, and wherein in operating said third one to monitor said SMIACC value, performing a step of determining a range of amplitude for each sense and assigning a weight value for each input amplifier output based on said range, then adding a first predetermined change increment value to said SMIACC value for each input amplifier output above a midrange of values, and subtracting a second predetermined change increment value from said SMIACC value for each input amplifier output in the midrange of values but above a center of said midrange, and subtracting a third predetermined change increment value from said SMIACC value for each input amplifier output that is below said midrange of values, and adding a fourth predetermined change increment value to said SMIACC value for each input amplifier output that is within said midrange but below a center of said midrange, and also wherein a step of determining whether a each input amplifier output is of too long a duration before adding or subtracting any of said increment values to said SMIACC value, and if said sense is of too long duration aborting the step of determining a range of amplitude for each sense.

10. The method of any of claims 1–5 wherein a third one of said at least two indicator means, said third one being a Sense Margin Indicator Accumulator (SMIACC) indicator means for holding an adjustable SMIACC value in a SMIACC memory register means for holding said adjustable SMIACC value which performs steps of monitoring and adjusting said input amplifier output and if one of said sense amplifier outputs is above a predetermined but adjustable margin value, said third one adjusts said SMIACC value stored in said SMIACC register memory means in a first direction, and wherein the steps of monitoring comprise, if said one of said outputs is below a lower second predetermined level, then adjusting said SMIACC value stored in said register means in a second and opposite direction, and operating said third one to monitor said SMIACC value wherein;

when said SMIACC value is below a predetermined low value producing an output signal representative of underflow from said third one and, when said SMIACC value is above a predetermined high value above said register level value, then producing an output signal indicative of overflow, and at such time as an output value representing underflow or overflow is produced by said third one, adjusting the input sense amplifier gain/threshold parameter value, upward or downward on the basis of whether there was an underflow or overflow value produced by said third indicator, and wherein in operating said third one to monitor said SMIACC value, performing a step of determining a range of amplitude for each sense and assigning a weight value for each input amplifier output based on said range, then adding a first predetermined change increment value to said SMIACC value for each input amplifier output above a midrange of values, and subtracting a second predetermined change increment value from said SMIACC value for each input amplifier output in the midrange of values but above a center of said midrange, and subtracting a third predetermined change increment value from said SMIACC value for each input amplifier output that is below said midrange of values, and adding a fourth predetermined change increment value to said SMIACC value for each input amplifier output that is within said midrange but below a center of said midrange, and wherein a step of determining valid input amplifier output for use by said LTA indicator means precedes any addition to said LTA count, wherein said step of determining valid input amplifier output for use by said LTA indicator means comprises determining that an input amplifier output is not a Premature Ventricular Contraction (PVC).

11. The method of any of claims 1–5 wherein a third one of said at least two indicator means, said third one being a Sense Margin Indicator Accumulator (SMIACC) indicator means for holding an adjustable SMIACC value in a SMIACC memory register means for holding said adjustable SMIACC value which performs steps of monitoring and adjusting said input amplifier output and if one of said sense amplifier outputs is above a predetermined but adjustable margin value, said third one adjusts said SMIACC value stored in said SMIACC register memory means in a first direction, and wherein the steps of monitoring comprise, if said one of said outputs is below a lower second predetermined level, then adjusting said SMIACC value stored in said register means in a second and opposite direction, and operating said third one to monitor said SMIACC value wherein;

when said SMIACC value is below a predetermined low value producing an output signal representative of underflow from said third one and, when said SMIACC value is above a predetermined high value above said register level value, then producing an output signal indicative of overflow, and at such time as an output value representing underflow or overflow is produced by said third one, adjusting the input sense amplifier gain/threshold parameter value, upward or downward on the basis of whether there was an underflow or overflow value produced by said third indicator, and wherein in operating said third one to monitor said SMIACC value, performing a step of determining a range of amplitude for each sense and assigning a weight value for each input amplifier output based on said range, then adding a first predetermined change increment value to said SMIACC value for each input amplifier output above a midrange of values, and subtracting a second predetermined change increment value from said SMIACC value for each input amplifier output in the midrange of values but above a center of said midrange, and subtracting a third predetermined change increment value from said SMIACC value for each input amplifier output that is below said midrange of values, and adding a fourth predetermined change increment value to said SMIACC value for each input amplifier output that is within said midrange but below a center of said midrange, and wherein a step of determining valid input amplifier output for use by said LTA indicator means precedes any addition to said LTA count, wherein said step of determining valid input amplifier output for use by said LTA indicator means comprises determining that an input amplifier output is not outside of a hardware overrange.

12. An implantable medical device comprising an input sense amplifier circuit with an automatic adjustment circuit for automatically adjusting a present gain/threshold parameter value of said input sense amplifier wherein said medical device operates said input sense amplifier to receive and evaluate senses of event specific pulses of electrical activity native to a body into which said device is adapted for implantation and to provide an output sense signal representative of said pulses of electrical activity as output subject to said present gain/threshold parameter value if there is sufficient electrical activity, said automatic adjustment circuit comprising:

a recordkeeping circuit for keeping track of at least two indicator values, a first one of said two indicator values being a Long Time Few Sense (LTFS) indicator, and the other of said two indicator values being a Long Term Average (LTA) indicator, and wherein said indicator values are required for adjustments to be made to said gain/threshold parameter value, said recordkeeping circuit comprising;

a plurality of indicator tracking circuits, comprising at least a LTFS indicator tracking circuit and a LTA tracking circuit, each tracking circuit for tracking one of said at least two indicator values based on each input sense amplifier output, wherein, said LTFS indicator tracking circuit is connected to receive output signals from said input sense amplifier circuit and comprises monitor circuit means for monitoring said input sense amplifier output to determine whether said LTFS indicator tracking circuit has received a number predetermined to be an insufficient number of output signals from said input sense amplifier circuit within a predetermined tracked period immediately preceding any given sense output signal from said input sense amplifier, said LTFS indicator tracking circuit further comprising first indicator output signal means for generating an LTFS output signal when said LTFS indicator tracking circuit has monitored a condition of having received said predetermined to be insufficient number of output sense signals from said input sense amplifier circuit within said predetermined tracking period, said LTA tracking circuit for monitoring said input sense amplifier output for valid sense output signals, comprising LTA signal value memory means for maintaining an LTA signal value, counter means for maintaining a count of said valid sense output signals, count sufficiency determining means for determining when said count becomes sufficient, and an LTA control circuit means for resetting the count and adjusting said LTA signal value and comprising a comparison circuit, wherein said adjusting of said LTA signal value employs said comparison circuit to compare a last LTA signal value to a current sense amplifier present gain/threshold parameter value if there is said LTFS signal present when said count becomes sufficient.

13. The implantable medical device of claim 12 wherein said LTFS tracking indicator circuit additionally comprises reversion status determination circuit means for determining whether there is a reversion status indicated before said LTFS tracking indicator circuit can generate said LTFS output, and a blocking circuit that only allows said LTFS output to be generated on a determination that a reversion status condition exists.

14. The implantable medical device of claim 12 comprising mode status circuitry for configuring said implantable medical device to be operable in a set of pacing status modes, and when said implantable medical device is operating in one such mode called VDD pacing status, and further comprising device circuitry for interpreting said input sense amplifier output signals for distinguishing ventricular from atrial senses in said output signals, wherein said amplifier output is connected to device circuitry and wherein said device circuitry has an output signal indicating such distinction and wherein said distinction indicating output is provided to said LTFS indicator tracking circuit which LTFS indicator tracking circuit additionally comprises timing and interpretive means for receiving said distinction indicating output, and for determining whether there have been two ventricular senses with no intervening atrial sense, and wherein said LTFS indicator tracking circuit can only generate said LTFS output signal on the determination that there have been two ventricular events without an intervening atrial event.

15. The implantable medical device of claim 13 further comprising monitoring circuitry for monitoring electrical events and pace/sense circuitry for generating a pace/sense signal indication of whether an electrical event monitored by said monitoring circuitry was paced or sensed and for providing signals indicative thereof to said LTFS indicator tracking circuit, and wherein said LTFS indicator tracking circuit further comprises a counting and storage circuit means for maintaining and storing a Paced Event Accumulator value by adding a pace value for each paced event, and subtracting a sense value for each sensed event to said stored PEA value stored in said counting and storage circuit means, wherein said stored value is changed more on a sensed than on a paced event, and wherein said LTFS indicator tracking circuit cannot produce said LTFS output signal until said stored PEA value reaches a preset value.

16. The implantable medical device of claim 15 further having a reversion circuit for determining a condition of noise reversion and producing a signal representative of such noise reversion condition and said LTFS tracking indicator circuit further comprising checking circuit means for checking for said noise reversion signal before generating said LTFS signal.

17. The implantable medical device of claim 16 wherein said LTA tracking circuit further comprises adjustment circuit means for
a) adjusting the value of the sense amplifier present gain/threshold parameter value to increase sensitivity, but only if said LTA signal value is higher than said gain/threshold parameter value, and
b) adjusting the value of the sense amplifier present gain/threshold parameter value to decrease sensitivity if there is no condition of noise reversion but only if the LTA value is lower than the present gain/threshold parameter value.

18. The implantable medical device of any of claims 12–17 further comprising a third tracking indicator circuit means of said plurality of indicator tracking circuits being a Sense Margin Indicator Accumulator (SMIACC) circuit, connected to receive said input sense amplifier output sense signals and to monitor them, and to adjust said input amplifier gain/threshold parameter value, said SMIACC circuit comprising;
within range determining circuit means for determining into which category, above, below and within an output sense signal should fit, relative to a predetermined adjustable amplitude range, and said range determining circuit means for producing a margin indicator signal representing a value indicative of this relation of said amplifier output signal to said range, and
a SMIACC register circuit means for storing a cumulative SMIACC value of all said margin indicator values wherein said SMIACC register circuit means has a predetermined upper value and a predetermined lower value and adjusts said cumulative SMIACC value in a first direction if said one of said sense amplifier outputs is below said range, then adjusting said cumulative SMIACC value in a second and opposite direction if said output signal is above said range, and
an indicator circuit means for interpreting said cumulative SMIACC value and if said cumulative SMIACC value achieves a predetermined upper limit value, producing a SMIACC overflow signal, and if said SMIACC value falls to a predetermined lower limit value, then producing a SMIACC underflow signal.

19. The implantable medical device of any of claims 12–17 further comprising a third tracking indicator circuit means of said plurality of indicator tracking circuits being a Sense Margin Indicator Accumulator (SMIACC) circuit, connected to receive said input sense amplifier output sense signals and to monitor them, and to adjust said input amplifier gain/threshold parameter value, said SMIACC circuit comprising;
within range determining circuit means for determining into which category, above, below and within an output sense signal should fit, relative to a predetermined adjustable amplitude range, and said range determining circuit means for producing a margin indicator signal representing a value indicative of this relation of said amplifier output signal to said range, and
a SMIACC register circuit means for storing a cumulative SMIACC value of all said margin indicator values wherein said SMIACC register circuit means has a predetermined upper value and a predetermined lower value and adjusts said cumulative SMIACC value in a first direction if said one of said sense amplifier outputs is below said range, then adjusting said cumulative SMIACC value in a second and opposite direction if said output signal is above said range, and
an indicator circuit means for interpreting said cumulative SMIACC value and if said cumulative SMIACC value achieves a predetermined upper limit value, producing a SMIACC overflow signal, and if said SMIACC value falls to a predetermined lower limit value, then producing a SMIACC underflow signal and further comprising
a weighting circuit means for providing weighting values wherein when said output from said sense amplifier is within said range, but above a selected point in said range, said weighting circuit means provides a first weighting value and adds said first weighting value to said cumulative SMIACC value and provides and adds to said cumulative SMIACC value a second weighting value when said output from said sense amplifier is above and outside said range, and provides and adds to said cumulative SMIACC value a third weighting value when said output from said sense amplifier is within said range, and below said selected point in said range and provides and adds to said cumulative SMIACC value a fourth weighting value is outside and below said range.

20. The implantable medical device of any of claims 12–17 further comprising a third tracking indicator circuit means of said plurality of indicator tracking circuits being a Sense Margin Indicator Accumulator (SMIACC) circuit, connected to receive said input sense amplifier output sense signals and to monitor them, and to adjust said input amplifier gain/threshold parameter value, said SMIACC circuit comprising;
within range determining circuit means for determining into which category, above, below and within an output sense signal should fit, relative to a predetermined adjustable amplitude range, and said range determining circuit means for producing a margin indicator signal representing a value indicative of this relation of said amplifier output signal to said range, and a SMIACC register circuit means for storing a cumulative SMIACC value of all said margin indicator values wherein said SMIACC register circuit means has a predetermined upper value and a predetermined lower value and adjusts said cumulative SMIACC value in a first direction if said one of said sense amplifier outputs is below said range, then adjusting said cumulative SMIACC value in a second and opposite direction if said output signal is above said range, and an indicator circuit means for interpreting said cumulative SMIACC value and if said cumulative SMIACC value achieves a predetermined upper limit value, producing a SMIACC overflow signal, and if said SMIACC value falls to a predetermined lower limit value, then producing a SMIACC underflow signal and further comprising a weighting circuit means for providing weighting values wherein when said output from said sense amplifier is within said range, but above a selected point in said range, said weighting circuit means provides a first weighting value and adds said first weighting value to said cumulative SMIACC value and provides and adds to said cumulative SMIACC value a second weighting value when said output from said sense amplifier is above and outside said range, and provides and adds to said cumulative SMIACC value a third weighting value when said output from said sense amplifier is within said range, and below said selected point in said range and provides and adds to said cumulative SMIACC value a fourth weighting value is outside and below said range and still further comprising means for determining a too long sense for determining whether a sense is of too long a duration before accepting any sense output for said manipulating said cumulative SMIACC value.

21. The implantable medical device of any of claims 12–17 further comprising a third tracking indicator circuit means of said plurality of indicator tracking circuits being a Sense Margin Indicator Accumulator (SMIACC) circuit, connected to receive said input sense amplifier output sense signals and to monitor them, and to adjust said input amplifier gain/threshold parameter value, said SMIACC circuit comprising;

within range determining circuit means for determining into which category, above, below and within an output sense signal should fit, relative to a predetermined adjustable amplitude range, and said range determining circuit means for producing a margin indicator signal representing a value indicative of this relation of said amplifier output signal to said range, and a SMIACC register circuit means for storing a cumulative SMIACC value of all said margin indicator values wherein said SMIACC register circuit means has a predetermined upper value and a predetermined lower value and adjusts said cumulative SMIACC value in a first direction if said one of said sense amplifier outputs is below said range, then adjusting said cumulative SMIACC value in a second and opposite direction if said output signal is above said range, and an indicator circuit means for interpreting said cumulative SMIACC value and if said cumulative SMIACC value achieves a predetermined upper limit value, producing a SMIACC overflow signal, and if said SMIACC value falls to a predetermined lower limit value, then producing a SMIACC underflow signal and further comprising a weighting circuit means for providing weighting values wherein when said output from said sense amplifier is within said range, but above a selected point in said range, said weighting circuit means provides a first weighting value and adds said first weighting value to said cumulative SMIACC value and provides and adds to said cumulative SMIACC value a second weighting value when said output from said sense amplifier is above and outside said range, and provides and adds to said cumulative SMIACC value a third weighting value when said output from said sense amplifier is within said range, and below said selected point in said range and provides and adds to said cumulative SMIACC value a fourth weighting value is outside and below said range and still further comprising means for determining a too long sense for determining whether a sense is of too long a duration before accepting any sense output for said manipulating said cumulative SMIACC value valid sense determining means for determining valid senses and to exclude invalid senses from use by LTA tracking circuit for addition to said LTA count wherein a step of determining valid senses for use by said LTA precedes any addition to said LTA count, wherein said step comprises determining that a sense is not outside of a hardware overrange.

* * * * *